(12) United States Patent (10) Patent No.: US 8,404,856 B2
Tucker et al. (45) Date of Patent: Mar. 26, 2013

(54) NON-NUCLEOSIDE REVERSE TRANSCRIPTASE INHIBITORS

(75) Inventors: Thomas J. Tucker, North Wales, PA (US); Robert Tynebor, Hatfield, PA (US); John T. Sisko, Lansdale, PA (US); Neville Anthony, Chalfont, PA (US); Robert Gomez, Perkasie, PA (US); Samson M. Jolly, Collegeville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 240 days.

(21) Appl. No.: 12/742,159

(22) PCT Filed: Nov. 14, 2008

(86) PCT No.: PCT/US2008/012774
§ 371 (c)(1),
(2), (4) Date: May 10, 2010

(87) PCT Pub. No.: WO2009/067166
PCT Pub. Date: May 28, 2009

(65) Prior Publication Data
US 2010/0256181 A1 Oct. 7, 2010

Related U.S. Application Data

(60) Provisional application No. 61/003,769, filed on Nov. 20, 2007.

(51) Int. Cl.
*C07D 403/00* (2006.01)
*C07D 401/00* (2006.01)
(52) U.S. Cl. ..................... 546/296; 548/360.5
(58) Field of Classification Search .................. 546/296; 548/360.5, 361.1, 377.1
See application file for complete search history.

(56) References Cited

U.S. PATENT DOCUMENTS

| 7,067,540 B2 | 6/2006 | Devadas et al. |
| 7,166,738 B2 | 1/2007 | Dunn et al. |
| 7,189,718 B2 | 3/2007 | Dunn et al. |
| 2004/0006114 A1 | 1/2004 | Coleman et al. |

(Continued)

FOREIGN PATENT DOCUMENTS

| EP | 0 481 802 A1 | 4/1992 |
| WO | 99/55676 A1 | 11/1999 |

(Continued)

OTHER PUBLICATIONS

Clemo et al. "The Lupin Alkaloids. Part XV. Some Derivatives of the 4-Oxo-3-2'-pyridylpyridocoline System", Journal of the Chemical Society, 1954, 2693-2701.

*Primary Examiner* — Paul Zarek
(74) *Attorney, Agent, or Firm* — Sheldon Heber; Raynard Yuro

(57) ABSTRACT

Heteroaromatic compounds of Formula (I) are HIV reverse transcriptase inhibitors, wherein ring A is: (ii-a), (ii-b), (ii-c), (ii-d), or (ii-e); and wherein n, L, M, U, X, Y, Z, $R^E$, $R^F$, $R^1$, $R^{2A}$, $R^{2B}$, $R^{2C}$, $R^3$, $R^8$, $R^9$ and $R^{10}$ are defined herein. The compounds of Formula I and their pharmaceutically acceptable salts and prodrugs are useful in the inhibition of HIV reverse transcriptase, the prophylaxis and treatment of infection by HIV and in the prophylaxis, delay in the onset or progression, and treatment of AIDS. The compounds and their salts and prodrugs can be employed as ingredients in pharmaceutical compositions, optionally in combination with other antivirals, immunomodulators, antibiotics or vaccines.

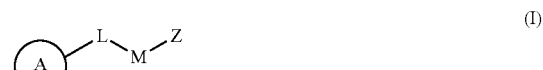

(I)

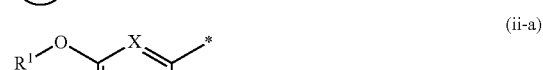

(ii-a)

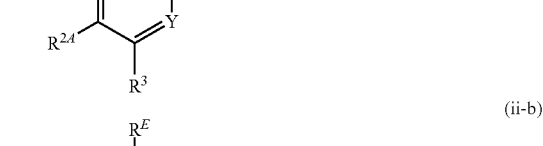

(ii-b)

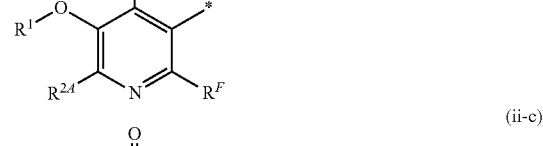

(ii-c)

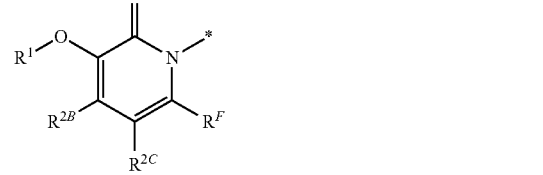

(ii-d)

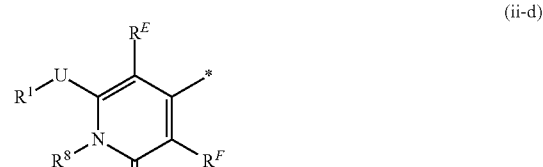

(ii-e)

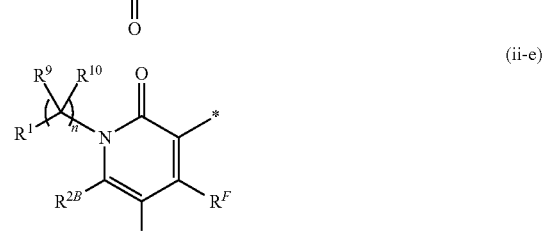

6 Claims, No Drawings

U.S. PATENT DOCUMENTS

| | | |
|---|---|---|
| 2007/0021442 A1 | 1/2007 | Saggar et al. |
| 2007/0088053 A1 | 4/2007 | Mirzadegan et al. |
| 2008/0194545 A1* | 8/2008 | Li et al. .................. 514/218 |
| 2008/0275097 A1 | 11/2008 | Anthony et al. |

FOREIGN PATENT DOCUMENTS

| | | |
|---|---|---|
| WO | 00/68201 A1 | 11/2000 |
| WO | 01/34578 A1 | 5/2001 |
| WO | 02/22602 A2 | 3/2002 |
| WO | 03/047577 A2 | 6/2003 |
| WO | 2004/069812 A1 | 8/2004 |
| WO | 2004/085406 A1 | 10/2004 |
| WO | 2005/102989 A1 | 11/2005 |
| WO | 2006/067587 A2 | 6/2006 |
| WO | 2007/015809 A2 | 2/2007 |
| WO | 2007/015812 A2 | 2/2007 |
| WO | 2007/045572 A1 | 4/2007 |

* cited by examiner

NON-NUCLEOSIDE REVERSE TRANSCRIPTASE INHIBITORS

CROSS-REFERENCE TO RELATED APPLICATIONS

This application is the National Stage of International Application No. PCT/US2008/012774, filed on Nov. 14, 2008, which claims the benefit of U.S. Provisional Application No. 61/003,769, filed Nov. 20, 2007, the disclosure of which is incorporated by reference herein in its entirety.

FIELD OF THE INVENTION

The present invention is directed to certain aryloxy-, cycloalkyloxy-, and heterocyclyloxy-pyridines and pyrimidines and related compounds and their use for the inhibition of HIV reverse transcriptase, the prophylaxis of HIV infection and HIV replication, the treatment of HIV infection and HIV replication, the prophylaxis of AIDS, the treatment of AIDS, and the delay in the onset and/or progression of AIDS.

BACKGROUND OF THE INVENTION

The retrovirus designated human immunodeficiency virus (HIV), particularly the strains known as HIV type-1 (HIV-1) and type-2 (HIV-2) viruses, have been etiologically linked to the immunosuppressive disease known as acquired immunodeficiency syndrome (AIDS). HIV seropositive individuals are initially asymptomatic but typically develop AIDS related complex (ARC) followed by AIDS. Affected individuals exhibit severe immunosuppression which makes them highly susceptible to debilitating and ultimately fatal opportunistic infections. Replication of HIV by a host cell requires integration of the viral genome into the host cell's DNA. Since HIV is a retrovirus, the HIV replication cycle requires transcription of the viral RNA genome into DNA via an enzyme known as reverse transcriptase (RT).

Reverse transcriptase has three known enzymatic functions: The enzyme acts as an RNA-dependent DNA polymerase, as a ribonuclease, and as a DNA-dependent DNA polymerase. In its role as an RNA-dependent DNA polymerase, RT transcribes a single-stranded DNA copy of the viral RNA. As a ribonuclease, RT destroys the original viral RNA and frees the DNA just produced from the original RNA. And as a DNA-dependent DNA polymerase, RT makes a second, complementary DNA strand using the first DNA strand as a template. The two strands form double-stranded DNA, which is integrated into the host cell's genome by the integrase enzyme.

It is known that compounds that inhibit enzymatic functions of HIV RT will inhibit HIV replication in infected cells. These compounds are useful in the prophylaxis or treatment of HIV infection in humans. Among the compounds approved for use in treating HIV infection and AIDS are the RT inhibitors 3'-azido-3'-deoxythymidine (AZT), 2',3'-dideoxyinosine (ddI), 2',3'-dideoxycytidine (ddC), d4T, 3TC, nevirapine, delavirdine, efavirenz and abacavir.

While each of the foregoing drugs is effective in treating HIV infection and AIDS, there remains a need to develop additional HIV antiviral drugs including additional RT inhibitors. A particular problem is the development of mutant HIV strains that are resistant to the known inhibitors. The use of RT inhibitors to treat AIDS often leads to viruses that are less sensitive to the inhibitors. This resistance is typically the result of mutations that occur in the reverse transcriptase segment of the pol gene. The continued use of antiviral compounds to prevent HIV infection will inevitably result in the emergence of new resistant strains of HIV. Accordingly, there is a particular need for new RT inhibitors that are effective against mutant HIV strains.

The following references are of interest as background:

Clemo et al., J. Chem. Soc. 1954, pp. 2693-2702 discloses certain derivatives of the 4-oxo-3-(2-pyridyl)pyridocoline system and in particular discloses 6-methyl-6'-phenoxy-2,2'-methylenedipyridine.

WO 2001/034578 discloses certain substituted azoles (including, for example, certain imidazoles and benzimidazoles) having anti-*Helicobacter pylori* activity. In particular, WO '578 discloses 1-[(3-methyl-4-phenoxy-2-pyridinyl)methyl]-1H-benzimidazole (see Compound 91 on page 40).

WO 2004/085406 and corresponding U.S. Pat. No. 7,189,718 disclose certain benzyl pyridazinones as reverse transcriptase inhibitors.

WO 2005/102989 and corresponding U.S. Pat. No. 7,166,738 disclose certain N-phenyl 2-phenylacetamides to be non-nucleoside reverse transcriptase inhibitors.

WO 2006/067587 discloses certain biaryl ether derivatives to be modulators of the reverse transcriptase enzyme.

US 2007/0021442 and WO 2007/015812 disclose certain substituted aromatic compounds. The compounds are HIV reverse transcriptase inhibitors suitable, for example, for the treatment of infection by HIV.

WO 2007/045572 and WO 2007/045573 disclose certain 2-(2-phenoxyphenyl) N-phenyl acetamides as non-nucleoside reverse transcriptase inhibitors.

WO 2008/076225 discloses certain indazoles, benzotriazoles and related bicyclic compounds as HIV reverse transcriptase inhibitors.

SUMMARY OF THE INVENTION

The present invention is directed to certain aryloxy-, cycloalkyloxy-, and heterocyclyloxy-pyridines and pyrimidines and related compounds and their use in the inhibition of HIV reverse transcriptase, the prophylaxis of infection by HIV, the treatment of infection by HIV, and the prophylaxis, treatment, and delay in the onset or progression of AIDS and/or ARC. More particularly, the present invention includes compounds of Formula I and pharmaceutically acceptable salts thereof:

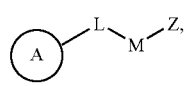
(I)

wherein:

ring A is:

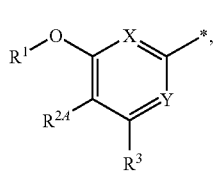
(ii-a)

-continued

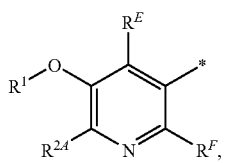
(ii-b)

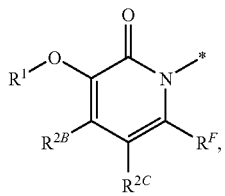
(ii-c)

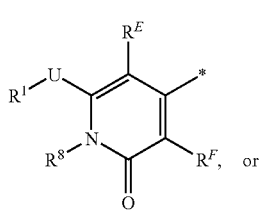
(ii-d)

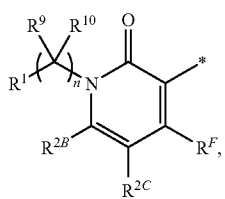
(ii-e)

wherein the asterisk (*) denotes the point of attachment of ring A to L;

$R^1$ is AryA, CycA, or HetA;

CycA is a carbocyclyl which is a $C_{3-8}$ cycloalkyl, a $C_{5-8}$ cycloalkenyl, or a $C_{7-12}$ bicyclic, saturated or unsaturated, non-aromatic ring system wherein one ring is fused to or bridged with the other ring; wherein the carbocyclyl is optionally substituted with a total of from 1 to 6 substituents, wherein:
(i) from zero to 6 substituents are each independently:
  (1) halogen,
  (2) CN,
  (3) $C_{1-6}$ alkyl,
  (4) OH,
  (5) O—$C_{1-6}$ alkyl,
  (6) $C_{1-6}$ haloalkyl,
  (7) O—$C_{1-6}$ haloalkyl,
  (8) $C_{1-6}$ alkenyl, or
  (9) $C_{1-6}$ alkenyl substituted with CN, and
(ii) from zero to 2 substituents are each independently:
  (1) CycQ,
  (2) AryQ,
  (3) HetQ,
  (4) HetR,
  (5) J-CycQ,
  (6) J-AryQ,
  (7) J-HetQ,
  (8) J-HetR,
  (9) $C_{1-6}$ alkyl substituted with CycQ, AryQ, HetQ, HetR, J-CycQ, J-AryQ, J-HetQ, or J-HetR,
  (10) $C_{2-6}$ alkenyl substituted with CycQ, AryQ, HetQ, HetR, J-CycQ, J-AryQ, J-HetQ, or J-HetR, or
  (11) $C_{2-6}$ alkynyl substituted with CycQ, AryQ, HetQ, HetR, J-CycQ, J-AryQ, J-HetQ, or J-HetR;

AryA is aryl which is optionally substituted with a total of from 1 to 8 substituents, wherein:
(i) from zero to 8 substituents are each independently:
  (1) $C_{1-6}$ alkyl,
  (2) $C_{1-6}$ haloalkyl,
  (3) $C_{1-6}$ alkyl substituted with from 1 to 3 substituents each of which is independently OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
  (4) $C_{2-6}$ alkenyl,
  (5) $C_{2-6}$ alkenyl substituted with from 1 to 3 substituents each of which is independently OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
  (6) $C_{2-6}$ alkynyl,
  (7) $C_{2-6}$ alkynyl substituted with from 1 to 3 substituents each of which is independently OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
  (8) O—$C_{1-6}$ alkyl,
  (9) O—$C_{1-6}$ haloalkyl,
  (10) OH,
  (11) halogen,
  (12) CN,
  (13) $NO_2$,
  (14) $N(R^A)R^B$,
  (15) $C(O)N(R^A)R^B$,
  (16) $C(O)R^A$,
  (17) C(O)—$C_{1-6}$ haloalkyl,
  (18) $C(O)OR^A$,
  (19) $OC(O)N(R^A)R^B$,
  (20) $SR^A$,
  (21) $S(O)R^A$,
  (22) $S(O)_2R^A$,
  (23) $S(O)_2N(R^A)R^B$,
  (24) $N(R^A)S(O)_2R^B$,
  (25) $N(R^A)S(O)_2N(R^A)R^B$,
  (26) $N(R^A)C(O)R^B$,
  (27) $N(R^A)C(O)N(R^A)R^B$,
  (28) $N(R^A)C(O)$—$C(O)N(R^A)R^B$, or
  (29) $N(R^A)CO_2R^B$, and
(ii) from zero to 2 substituents are each independently:
  (1) CycQ,
  (2) AryQ,
  (3) HetQ,
  (4) HetR,
  (5) J-CycQ,
  (6) J-AryQ,
  (7) J-HetQ,
  (8) J-HetR,
  (9) $C_{1-6}$ alkyl substituted with CycQ, AryQ, HetQ, HetR, J-CycQ, J-AryQ, J-HetQ, or J-HetR,
  (10) $C_{2-6}$ alkenyl substituted with CycQ, AryQ, HetQ, HetR, J-CycQ, J-AryQ, J-HetQ, or J-HetR, or
  (11) $C_{2-6}$ alkynyl substituted with CycQ, AryQ, HetQ, HetR, J-CycQ, J-AryQ, J-HetQ, or J-HetR;

HetA is a heterocyclyl which is optionally substituted with a total of from 1 to 8 substituents, wherein:
(i) from zero to 8 substituents are each independently:
(1) $C_{1-6}$ alkyl,
(2) $C_{1-6}$ haloalkyl, which is optionally substituted with O—$C_{1-6}$ alkyl, $C(O)R^A$, $CO_2R^A$, $C(O)N(R^A)R^B$, $SR^A$, $S(O)R^A$, or $SO_2R^A$,
(3) $C_{1-6}$ alkyl substituted with from 1 to 3 substituents each of which is OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(4) $C_{2-6}$ alkenyl,
(5) $C_{2-6}$ alkenyl substituted with from 1 to 3 substituents each of which is independently OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(6) $C_{2-6}$ alkynyl,
(7) $C_{2-6}$ alkynyl substituted with from 1 to 3 substituents each of which is independently OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(8) O—$C_{1-6}$ alkyl,
(9) O—$C_{1-6}$ haloalkyl,
(10) OH,
(11) oxo,
(12) halogen,
(13) CN,
(14) $NO_2$,
(15) $N(R^A)R^B$,
(16) $C(O)N(R^A)R^B$,
(17) $C(O)R^A$,
(18) $C(O)$—$C_{1-6}$ haloalkyl,
(19) $C(O)OR^A$,
(20) $OC(O)N(R^A)R^B$,
(21) $SR^A$,
(22) $S(O)R^A$,
(23) $S(O)_2R^A$,
(24) $S(O)_2N(R^A)R^B$,
(25) $N(R^A)S(O)_2R^B$,
(26) $N(R^A)S(O)_2N(R^A)R^B$,
(27) $N(R^A)C(O)R^B$,
(28) $N(R^A)C(O)N(R^A)R^B$,
(29) $N(R^A)C(O)$—$C(O)N(R^A)R^B$, or
(30) $N(R^A)CO_2R^B$, and
(ii) from zero to 2 substituents are each independently:
(1) CycQ,
(2) AryQ,
(3) HetQ,
(4) HetR,
(5) J-CycQ,
(6) J-AryQ,
(7) J-HetQ,
(8) J-HetR,
(9) $C_{1-6}$ alkyl substituted with CycQ, AryQ, HetQ, HetR, J-CycQ, J-AryQ, J-HetQ, or J-HetR,
(10) $C_{2-6}$ alkenyl substituted with CycQ, AryQ, HetQ, HetR, J-CycQ, J-AryQ, J-HetQ, or J-HetR, or
(11) $C_{2-6}$ alkynyl substituted with CycQ, AryQ, HetQ, HetR, J-CycQ, J-AryQ, J-HetQ, or J-HetR;
each CycQ is independently $C_{3-8}$ cycloalkyl or $C_{5-8}$ cycloalkenyl, wherein the cycloalkyl or cycloalkenyl is optionally substituted with from 1 to 4 substituents, each of which is independently halogen, $C_{1-6}$ alkyl, OH, O—$C_{1-6}$ alkyl, $C_{1-6}$ haloalkyl, or O—$C_{1-6}$ haloalkyl;
each AryQ is independently phenyl or naphthyl, wherein the phenyl or naphthyl is optionally substituted with from 1 to 5 substituents each of which is independently halogen, CN, $NO_2$, $C_{1-6}$ alkyl, $C_{1-6}$ haloalkyl, OH, O—$C_{1-6}$ alkyl, O—$C_{1-6}$ haloalkyl, $N(R^A)R^B$, $C(O)N(R^A)R^B$, $C(O)R^A$, $CO_2R^A$, $SR^A$, $S(O)R^A$, $SO_2R^A$, $SO_2N(R^A)R^B$, or $SO_2N(R^A)C(O)R^B$;
each HetQ is independently a heteroaryl which is optionally substituted with from 1 to 4 substituents each of which is independently halogen, $C_{1-6}$ alkyl, $C_{1-6}$ haloalkyl, OH, O—$C_{1-6}$ alkyl, O—$C_{1-6}$ haloalkyl, $N(R^A)R^B$, $C(O)N(R^A)R^B$, $C(O)R^A$, $CO_2R^A$, $SO_2R^A$, $N(R^A)C(O)N(R^A)R^B$, or $N(R^A)CO_2R^B$;
each HetR is independently a 4-to 7-membered, saturated or unsaturated, non-aromatic heterocyclic ring containing at least one carbon atom and from 1 to 4 heteroatoms independently selected from N, O and S, where each S is optionally oxidized to S(O) or $S(O)_2$, and wherein the saturated or unsaturated heterocyclic ring is optionally substituted with from 1 to 4 substituents each of which is independently halogen, CN, $C_{1-6}$ alkyl, OH, oxo, O—$C_{1-6}$ alkyl, $C_{1-6}$ haloalkyl, O—$C_{1-6}$ haloalkyl, $C(O)N(R^A)R^B$, $C(O)R^A$, $CO_2R^A$, or $SO_2R^A$;
each J is independently:
(i) O,
(ii) S,
(iii) S(O),
(iv) $S(O)_2$,
(v) O—$C_{1-6}$ alkylene,
(vi) S—$C_{1-6}$ alkylene,
(vii) S(O)—$C_{1-6}$ alkylene,
(viii) $S(O)_2$—$C_{1-6}$ alkylene,
(ix) $N(R^A)$, or
(x) $N(R^A)$—$C_{1-6}$ alkylene;
$R^{2A}$, $R^{2B}$, and $R^{2C}$ are each independently:
(1) H,
(2) $C_{1-6}$ alkyl,
(3) $C_{1-6}$ haloalkyl,
(4) $C_{1-6}$ alkyl substituted with from 1 to 3 substituents each of which is independently OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(5) O—$C_{1-6}$ alkyl in which the alkyl is optionally substituted with OH, O—$C_{1-6}$ alkyl, O—$C_{1-6}$ haloalkyl, CN, $N(R^A)R^B$, $C(O)N(R^A)R^B$, $C(O)R^A$, $CO_2R^A$, $SR^A$, $S(O)R^A$, $S(O)_2R^A$, or $S(O)_2N(R^A)R^B$,
(6) O—$C_{1-6}$ haloalkyl,
(7) halogen,
(8) CN,
(9) $NO_2$,
(10) $N(R^A)R^B$,
(11) $C(O)N(R^A)R^B$,
(12) $C(O)R^A$,
(13) $C(O)$—$C_{1-6}$ haloalkyl,
(14) $C(O)OR^A$,
(15) $OC(O)R^A$,
(16) $OC(O)N(R^A)R^B$,

(17) $SR^A$,
(18) $S(O)R^A$,
(19) $S(O)_2R^A$,
(20) $S(O)_2N(R^A)R^B$,
(21) $N(R^A)S(O)_2R^B$,
(22) $N(R^A)S(O)_2N(R^A)R^B$,
(23) $N(R^A)C(O)R^B$,
(24) $N(R^A)C(O)N(R^A)R^B$,
(25) $N(R^A)C(O)—C(O)N(R^A)R^B$,
(26) $N(R^A)CO_2R^B$,
(27) $N(R^C)R^D$,
(28) $C(O)N(R^C)R^D$,
(29) $OC(O)N(R^C)R^D$,
(30) $S(O)_2N(R^C)R^D$,
(31) $N(R^A)S(O)_2N(R^C)R^D$,
(32) $N(R^A)C(O)N(R^C)R^D$,
(33) $N(R^A)C(O)—C(O)N(R^C)R^D$,
(34) $C_{3-8}$ cycloalkyl, or
(35) $O—C_{3-8}$ cycloalkyl;
$R^3$ is OH or independently has the same definition as $R^{2A}$;
X is N or $C(R^E)$;
Y is N or $C(R^F)$, with the proviso that either one of X and Y is N or both X and Y are N;
$R^E$ is H, $C_{1-6}$ alkyl, halogen, CN, or $C_{1-6}$ fluoroalkyl;
$R^F$ is H, $C_{1-6}$ alkyl, halogen, CN, or $C_{1-6}$ fluoroalkyl;
U is:
 (1) O,
 (2) S,
 (3) S(O),
 (4) $S(O)_2$,
 (5) $CH_2$,
 (6) $CH(CH_3)$, or
 (7) $C(CH_3)_2$;
L is:
 (1) a single bond that attaches ring A directly to M,
 (2) O,
 (3) $N(R^A)$,
 (4) S,
 (5) S(O),
 (6) $S(O)_2$,
 (7) $CH_2$,
 (8) $CH(CH_3)$, or
 (9) $C(CH_3)_2$;
M is $CH_2$, $CH(CH_3)$, $C(CH_3)_2$, CH(OH), or $C(O)N(R^A)$;
Z is $G^1$, $G^2$, $G^3$, or $G^4$;
$G^1$ is:

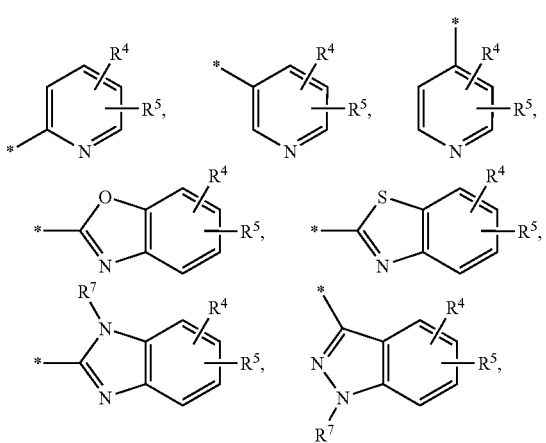

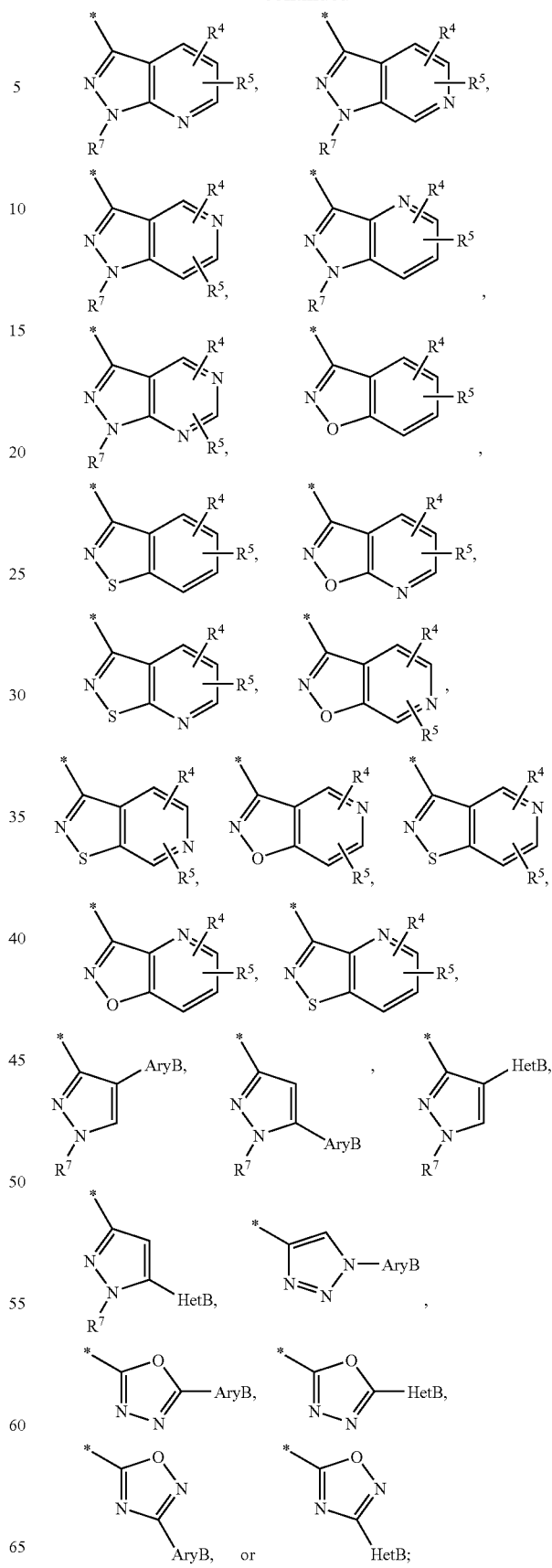

$G^2$ is:

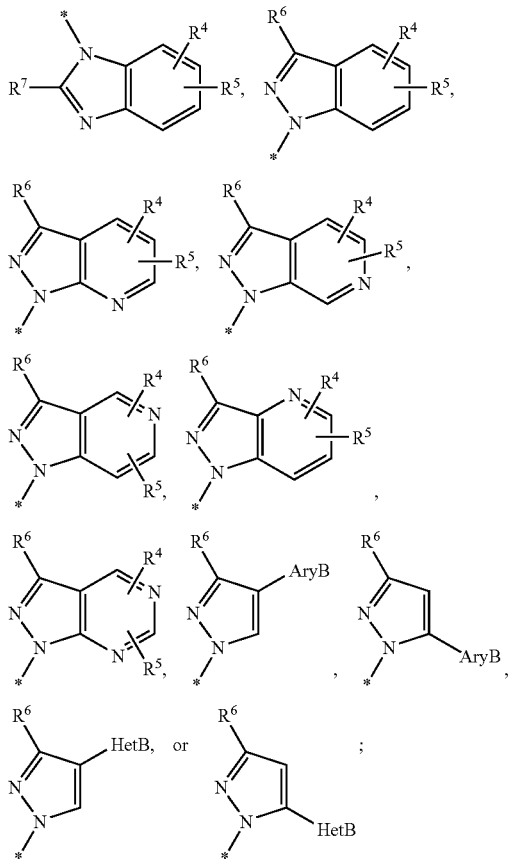

$G^3$ is:

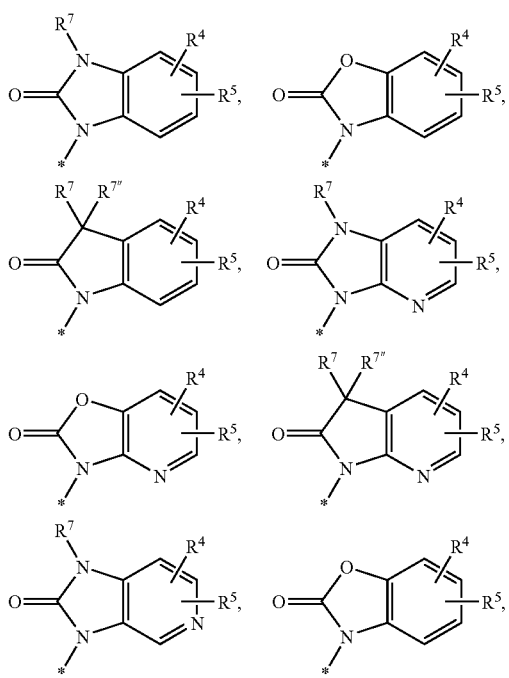

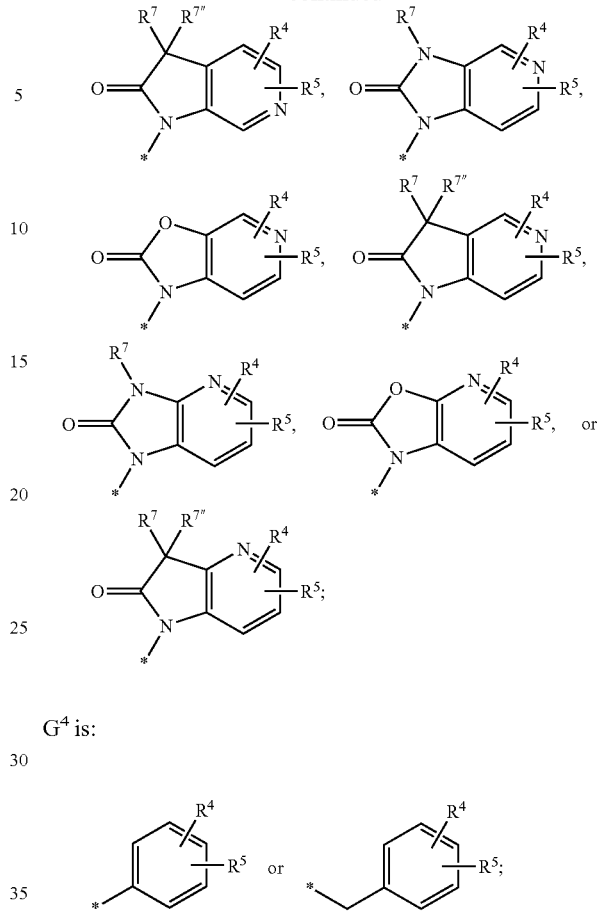

$G^4$ is:

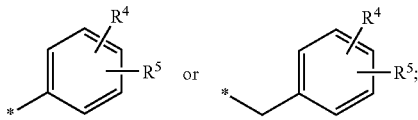

and provided that:
(a) when Z is $G^2$ or $G^3$ and ring A is ii-a or ii-b or ii-d or ii-e, then L is a single bond that attaches ring A directly to M, $CH_2$, $CH(CH_3)$, or $C(CH_3)_2$; and M is $CH_2$, $CH(CH_3)$, $C(CH_3)_2$, or $CH(OH)$;
(b) when Z is $G^2$ or $G^3$ and ring A is ii-c, then L is $CH_2$, $CH(CH_3)$, or $C(CH_3)_2$; and M is $CH_2$, $CH(CH_3)$, $C(CH_3)_2$, or $CH(OH)$;
(c) when Z is $G^1$ and ring A is ii-c, then L is a single bond that attaches ring A directly to M, $CH_2$, $CH(CH_3)$, or $C(CH_3)_2$; and M is $CH_2$, $CH(CH_3)$, $C(CH_3)_2$, or $CH(OH)$; and
(d) when Z is $G^4$, then ring A is ii-c; L is $CH_2$, $CH(CH_3)$, or $C(CH_3)_2$; and M is $C(O)N(R^A)$;

$R^4$ and $R^5$ are each independently:
(1) H,
(2) $C_{1-6}$ alkyl,
(3) $C_{1-6}$ haloalkyl,
(4) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(5) O—$C_{1-6}$ alkyl in which the alkyl is optionally substituted with OH, O—$C_{1-6}$ alkyl, O—$C_{1-6}$ haloalkyl, CN, $N(R^A)R^B$, $C(O)N(R^A)R^B$, $C(O)R^A$, $CO_2R^A$, $SR^A$, $S(O)R^A$, $S(O)_2R^A$, or $S(O)_2N(R^A)R^B$,
(6) O—$C_{1-6}$ haloalkyl,
(7) halogen, (8) CN,
(9) $NO_2$,
(10) $N(R^A)R^B$,
(11) $C(O)N(R^A)R^B$,
(12) $C(O)R^A$,
(13) $C(O)$—$C_{1-6}$ haloalkyl,
(14) $C(O)OR^A$,
(15) $OC(O)R^A$,
(16) $OC(O)N(R^A)R^B$,
(17) $SR^A$,
(18) $S(O)R^A$,
(19) $S(O)_2R^A$,
(20) $S(O)_2N(R^A)R^B$,
(21) $N(R^A)S(O)_2R^B$,
(22) $N(R^A)S(O)_2N(R^A)R^B$,
(23) $N(R^A)C(O)R^B$,
(24) $N(R^A)C(O)N(R^A)R^B$,
(25) $N(R^A)C(O)$—$C(O)N(R^A)R^B$,
(26) $N(R^A)CO_2R^B$,
(27) $N(R^C)R^D$,
(28) $C(O)N(R^C)R^D$,
(29) $OC(O)N(R^C)R^D$,
(30) $S(O)_2N(R^C)R^D$,
(31) $N(R^A)S(O)_2N(R^C)R^D$,
(32) $N(R^A)C(O)N(R^C)R^D$,
(33) $N(R^A)C(O)$—$C(O)N(R^C)R^D$,
(34) $C_{3-8}$ cycloalkyl,
(35) O—$C_{3-8}$ cycloalkyl,
(36) OH, or
(37) imidazolyl;

$R^6$ is H, $C_{1-6}$ alkyl, OH, O—$C_{1-6}$ alkyl, $N(R^A)R^B$, or $N(R^C)R^D$;

$R^7$ and $R^{7''}$ are each independently H or $C_{1-6}$ alkyl;

$R^8$ is H or $C_{1-6}$ alkyl;

each $R^9$ is H or $C_{1-6}$ alkyl;

each $R^{10}$ is H or $C_{1-6}$ alkyl;

n is an integer equal to 1 or 2;

AryB independently has the same definition as AryA;

HetB is a heteroaryl which is optionally substituted with from 1 to 6 substituents each of which is independently:
(1) $C_{1-6}$ alkyl,
(2) $C_{1-6}$ haloalkyl, which is optionally substituted with O—$C_{1-6}$ alkyl, $C(O)R^A$, $CO_2R^A$, $C(O)N(R^A)R^B$, $SR^A$, $S(O)R^A$, or $SO_2R^A$,
(3) $C_{1-6}$ alkyl substituted with from 1 to 3 substituents each of which is OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
(4) O—$C_{1-6}$ alkyl,
(5) O—$C_{1-6}$ haloalkyl,
(6) OH,
(7) halogen,
(8) CN,
(9) $NO_2$,
(10) $N(R^A)R^B$,
(11) $C(O)N(R^A)R^B$,
(12) $C(O)R^A$,
(13) $C(O)$—$C_{1-6}$ haloalkyl,
(14) $C(O)OR^A$,
(15) $OC(O)N(R^A)R^B$,
(16) $SR^A$,
(17) $S(O)R^A$,
(18) $S(O)_2R^A$,
(19) $S(O)_2N(R^A)R^B$,
(20) $N(R^A)S(O)_2R^B$,
(21) $N(R^A)S(O)_2N(R^A)R^B$,
(22) $N(R^A)C(O)R^B$,
(23) $N(R^A)C(O)N(R^A)R^B$,
(24) $N(R^A)C(O)$—$C(O)N(R^A)R^B$, or
(25) $N(R^A)CO_2R^B$,
(26) $N(R^C)R^D$,
(27) $C(O)N(R^C)R^D$,
(28) $OC(O)N(R^C)R^D$,
(29) $S(O)_2N(R^C)R^D$,
(30) $N(R^A)S(O)_2N(R^C)R^D$,
(31) $N(R^A)C(O)N(R^C)R^D$,
(32) $N(R^A)C(O)$—$C(O)N(R^C)R^D$,
(33) $C_{3-8}$ cycloalkyl, or
(34) O—$C_{3-8}$ cycloalkyl;

each aryl is independently (i) phenyl, (ii) a 9- or 10-membered bicyclic, fused carbocyclic ring system in which at least one ring is aromatic, or (iii) an 11- to 14-membered tricyclic, fused carbocyclic ring system in which at least one ring is aromatic;

each heterocyclyl is independently (i) a 4- to 8-membered, saturated or unsaturated monocyclic ring, (ii) a 7- to 12-membered bicyclic ring system, or (iii) a 10- to 18-membered tricyclic ring system, wherein each ring in (ii) or (iii) is independent of, fused to, or bridged with the other ring or rings and each ring is saturated or unsaturated; wherein the monocyclic ring contains from 1 to 4 heteroatoms and a balance of carbon atoms; the bicyclic ring system or tricyclic ring system contains from 1 to 8 heteroatoms and a balance of carbon atoms, wherein one or more of the rings contain one or more of the heteroatoms; wherein the heteroatoms are selected from N, O and S; and wherein any one or more of the nitrogen and sulfur heteroatoms is optionally oxidized, and any one or more of the nitrogen heteroatoms is optionally quaternized;

each heteroaryl is independently (i) a 5- or 6-membered heteroaromatic ring containing from 1 to 4 heteroatoms independently selected from N, O and S, wherein each N is optionally in the form of an oxide, or (ii) a 9- or 10-membered heterobicyclic, fused ring system containing from 1 to 4 heteroatoms independently selected from N, O and S, wherein either one or both of the rings contain one or more of the heteroatoms, at least one ring is aromatic, each N is optionally in the form of an oxide, and each S in a ring which is not aromatic is optionally $S(O)$ or $S(O)_2$;

each $R^A$ is independently H or $C_{1-6}$ alkyl;
each $R^B$ is independently H or $C_{1-6}$ alkyl;
each $R^C$ is independently H or $C_{1-6}$ alkyl;
each $R^D$ is independently H or $C_{1-6}$ alkyl;

or alternatively each pair of $R^C$ and $R^D$ together with the nitrogen to which they are both attached form a 4- to 7-membered saturated or mono-unsaturated ring which optionally contains a heteroatom in addition to the N to which $R^C$ and $R^D$ are attached, wherein the additional heteroatom is selected from N, O, and S; wherein the ring is optionally substituted with 1 or 2 substituents each of which is independently $C_{1-6}$ alkyl, $C(O)R^A$, $C(O)OR^A$, $C(O)N(R^A)R^B$, or $S(O)_2R^A$; and wherein the optional S in the ring is optionally in the form of $S(O)$ or $S(O)_2$;

and provided that:
(A) the compound of Formula I is not 1-[(3-methyl-4-phenoxy-2-pyridinyl)methyl]-1H-benzimidazole, and
(B) the compound of Formula I is not 6-methyl-6'-phenoxy-2,2'-methylenedipyridine.

Embodiments, aspects and features of the present invention are either further described in or will be apparent from the ensuing description, examples and appended claims.

DETAILED DESCRIPTION OF THE INVENTION

The compounds of Formula I above, and pharmaceutically acceptable salts thereof, are HIV reverse transcriptase inhibitors. The compounds are useful for inhibiting HIV reverse transcriptase and for inhibiting HIV replication in vitro and in vivo. More particularly, the compounds of Formula I inhibit the polymerase function of HIV-1 reverse transcriptase. Based upon the testing of representative compounds of the invention in the assays set forth in Example 27 below, it is known that compounds of Formula I inhibit the RNA-dependent DNA polymerase activity of HIV-1 reverse transcriptase. Representative compounds of the present invention also exhibit activity against drug resistant forms of HIV (e.g., mutant strains of HIV-1 in which reverse transcriptase has a mutation at lysine 103→asparagine (K103N) and/or tyrosine 181→cysteine (Y181C)), and thus can exhibit decreased cross-resistance against currently approved antiviral therapies.

A first embodiment of the present invention (alternatively referred to herein as "Embodiment E1") is a compound of Formula I (alternatively and more simply referred to as "Compound I"), or a pharmaceutically acceptable salt thereof; wherein:

CycA is a carbocyclyl which is a $C_{3-8}$ cycloalkyl, a $C_{5-8}$ cycloalkenyl, or a $C_{7-12}$ bicyclic, saturated or unsaturated, non-aromatic ring system wherein one ring is fused to or bridged with the other ring; wherein the carbocyclyl is optionally substituted with a total of from 1 to 6 substituents, wherein:
  (i) from zero to 6 substituents are each independently:
    (1) halogen,
    (2) CN
    (3) $C_{1-6}$ alkyl,
    (4) OH,
    (5) O—$C_{1-6}$ alkyl,
    (6) $C_{1-6}$ haloalkyl, or
    (7) O—$C_{1-6}$ haloalkyl, and
  (ii) from zero to 2 substituents are each independently:
    (1) CycQ,
    (2) AryQ,
    (3) HetQ,
    (4) HetR,
    (5) J-CycQ,
    (6) AryQ,
    (7) J-HetQ,
    (8) HetR,
    (9) $C_{1-6}$ alkyl substituted with CycQ, AryQ, HetQ, HetR, J-CycQ, J-AryQ, HetQ, or HetR,
    (10) $C_{2-6}$ alkenyl substituted with CycQ, AryQ, HetQ, HetR, J-CycQ, J-AryQ, J-HetQ, or HetR, or
    (11) $C_{2-6}$ alkynyl substituted with CycQ, AryQ, HetQ, HetR, J-CycQ, J-AryQ, J-HetQ, or J-HetR;

$R^E$ is H, $C_{1-6}$ alkyl, halogen, or CN;
$R^F$ is H, $C_{1-6}$ alkyl, halogen, or CN;
M is $CH_2$, $CH(CH_3)$, or $C(CH_3)_2$;
Z is $G^1$, $G^2$, or $G^3$; and provided that:
  (a) when Z is $G^2$ or $G^3$ and ring A is ii-a or ii-b or ii-d or ii-e, then L is a single bond that attaches ring A directly to M, $CH_2$, $CH(CH_3)$, or $C(CH_3)_2$, and M is $CH_2$, $CH(CH_3)$, or $C(CH_3)_2$,
  (b) when Z is $G^2$ or $G^3$ and ring A is ii-c, then L is $CH_2$, $CH(CH_3)$, or $C(CH_3)_2$, and M is $CH_2$, $CH(CH_3)$, or $C(CH_3)_2$, and
  (c) when Z is $G^1$ and ring A is ii-c, then L is a single bond that attaches ring A directly to M, $CH_2$, $CH(CH_3)$, or $C(CH_3)_2$, and M is $CH_2$, $CH(CH_3)$, or $C(CH_3)_2$;

$R^4$ and $R^5$ are each independently:
  (1) H,
  (2) $C_{1-6}$ alkyl,
  (3) $C_{1-6}$ haloalkyl,
  (4) $C_{1-6}$ alkyl substituted with OH, O—$C_{1-6}$ alkyl, O—$C_{1-6}$ haloalkyl, CN, $NO_2$, $N(R^A)R^B$, $C(O)N(R^A)R^B$, $C(O)R^A$, $CO_2R^A$, $SR^A$, $S(O)R^A$, $S(O)_2R^A$, $S(O)_2N(R^A)R^B$, $N(R^A)C(O)R^B$, $N(R^A)CO_2R^B$, $N(R^A)S(O)_2R^B$, $N(R^A)S(O)_2N(R^A)R^B$, $OC(O)N(R^A)R^B$, $N(R^A)C(O)N(R^A)R^B$, or $N(R^A)C(O)C(O)N(R^A)R^B$,
  (5) O—$C_{1-6}$ alkyl in which the alkyl is optionally substituted with OH, O—$C_{1-6}$ alkyl, O—$C_{1-6}$ haloalkyl, CN, $N(R^A)R^B$, $C(O)N(R^A)R^B$, $C(O)R^A$, $CO_2R^A$, $SR^A$, $S(O)R^A$, $S(O)_2R^A$, or $S(O)_2N(R^A)R^B$,
  (6) O—$C_{1-6}$ haloalkyl,
  (7) halogen,
  (8) CN,
  (9) $NO_2$,
  (10) $N(R^A)R^B$,
  (11) $C(O)N(R^A)R^B$,
  (12) $C(O)R^A$,
  (13) $C(O)$—$C_{1-6}$ haloalkyl,
  (14) $C(O)OR^A$,
  (15) $OC(O)R^A$,
  (16) $OC(O)N(R^A)R^B$,
  (17) $SR^A$,
  (18) $S(O)R^A$,
  (19) $S(O)_2R^A$,
  (20) $S(O)_2N(R^A)R^B$,
  (21) $N(R^A)S(O)_2R^B$,
  (22) $N(R^A)S(O)_2N(R^A)R^B$,
  (23) $N(R^A)C(O)R^B$,
  (24) $N(R^A)C(O)N(R^A)R^B$,
  (25) $N(R^A)C(O)$—$C(O)N(R^A)R^B$,
  (26) $N(R^A)CO_2R^B$,
  (27) $N(R^C)R^D$,
  (28) $C(O)N(R^C)R^D$,
  (29) $OC(O)N(R^C)R^D$,
  (30) $S(O)_2N(R^C)R^D$,
  (31) $N(R^A)S(O)_2N(R^C)R^D$,
  (32) $N(R^A)C(O)N(R^C)R^D$,
  (33) $N(R^A)C(O)$—$C(O)N(R^C)R^D$,
  (34) $C_{3-8}$ cycloalkyl,
  (35) O—$C_{3-8}$ cycloalkyl, or
  (36) OH;
and all other variables and provisos are as originally defined (i.e., as defined in the Summary of the Invention above).

A second embodiment of the present invention (Embodiment E2) is a compound of Formula I as originally defined or as defined in Embodiment E1, or a pharmaceutically acceptable salt thereof; and provided that:

(A) when ring A is ring ii-a, X is $C(R^E)$, $R^E$ is H or $C_{1-6}$ alkyl, and Y is N, then $G^2$ is not

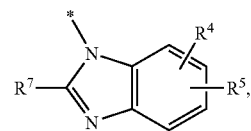

and (B) the compound of Formula I is not 6-methyl-6'-phenoxy-2,2'-methylenedipyridine.

A third embodiment of the present invention (Embodiment E3) is a compound of Formula I as originally defined or as defined in Embodiment E1, or a pharmaceutically acceptable salt thereof; and provided that:

(A) when ring A is ring ii-a, X is C(R$^E$) and Y is N, then G$^2$ is not

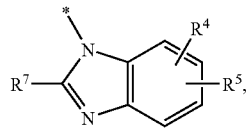

and (B) the compound of Formula I is not 6-methyl-6'-phenoxy-2,2'-methylenedipyridine.

A fourth embodiment of the present invention (Embodiment E4) is a compound of Formula I, or a pharmaceutically acceptable salt thereof; wherein R$^1$ is AryA or HetA; and all other variables are as originally defined or as defined in Embodiment E1 or Embodiment E2 or Embodiment E3.

A fifth embodiment of the present invention (Embodiment E5) is a compound of Formula I, or a pharmaceutically acceptable salt thereof; wherein R$^1$ is AryA; and all other variables are as originally defined or as defined in Embodiment E1 or Embodiment E2 or Embodiment E3.

A sixth embodiment of the present invention (Embodiment E6) is a compound of Formula I, or a pharmaceutically acceptable salt thereof; wherein R$^1$ is AryA which is phenyl or naphthyl, wherein the phenyl or naphthyl is optionally substituted with from 1 to 3 substituents each of which is independently halogen, CN, NO$_2$, C$_{1-4}$ alkyl, C$_{1-4}$ haloalkyl, C$_{2-4}$ alkenyl, C$_{2-4}$ alkenyl substituted with CN, OH, O—C$_{1-4}$ alkyl, O—C$_{1-4}$ haloalkyl, N(R$^A$)R$^B$, C(O)N(R$^A$)R$^B$, C(O)R$^A$, CO$_2$R$^A$, SR$^A$, S(O)R$^A$, SO$_2$R$^A$, SO$_2$N(R$^A$)R$^B$, or SO$_2$N(R$^A$)C(O)R$^B$; wherein any R$^A$ or R$^B$ which is part of a substituent in AryA is H or C$_{1-4}$ alkyl; and all other variables are as originally defined or as defined in Embodiment E1 or Embodiment E2 or Embodiment E3. It is understood that in this embodiment the definition of R$^A$ or R$^B$ in other variables is independent of and not limited to the definition of R$^A$ or R$^B$ in R$^1$; i.e., the definition of any R$^A$ or R$^B$ in another variable (e.g., R$^{2A}$, R$^{2B}$, R$^{2C}$, or R$^3$) remains H or C$_{1-6}$ alkyl.

A seventh embodiment of the present invention (Embodiment E7) is a compound of Formula I, or a pharmaceutically acceptable salt thereof; wherein R$^1$ is AryA wherein AryA is phenyl which is optionally substituted with from 1 to 3 substituents each of which is independently Cl, Br, F, CN, NO$_2$, C$_{1-4}$ alkyl, C$_{1-4}$ fluoroalkyl, CH=CH—CN, OH, O—C$_{1-4}$ alkyl, O—C$_{1-4}$ fluoroalkyl, NH$_2$, N(H)CH$_3$, N(CH$_3$)$_2$, C(O)NH$_2$, C(O)N(H)CH$_3$, C(O)N(CH$_3$)$_2$, C(O)CH$_3$, CO$_2$CH$_3$, CO$_2$CH$_2$CH$_3$, SCH$_3$, S(O)CH$_3$, SO$_2$CH$_3$, SO$_2$NH$_2$, SO$_2$N(H)CH$_3$, or SO$_2$N(CH$_3$)$_2$; and all other variables are as originally defined or as defined in Embodiment E1 or Embodiment E2 or Embodiment E3. In a first sub-embodiment of this embodiment, the phenyl group is optionally substituted with from 1 to 3 substituents each of which is independently Cl, Br, F, CN, NO$_2$, C$_{1-4}$ alkyl, C$_{1-4}$ fluoroalkyl, CH=CH—CN, OH, O—C$_{1-4}$ alkyl, O—C$_{1-4}$ fluoroalkyl, NH$_2$, N(H)CH$_3$, N(CH$_3$)$_2$, C(O)NH$_2$, C(O)N(H)CH$_3$, C(O)N(CH$_3$)$_2$, C(O)CH$_3$, CO$_2$CH$_3$, SCH$_3$, S(O)CH$_3$, SO$_2$CH$_3$, SO$_2$NH$_2$, SO$_2$N(H)CH$_3$, or SO$_2$N(CH$_3$)$_2$.

An eighth embodiment of the present invention (Embodiment E8) is a compound of Formula I, or a pharmaceutically acceptable salt thereof; wherein R$^1$ is AryA wherein AryA is phenyl which is optionally substituted with 1 or 2 substituents each of which is independently Cl, Br, F, CN, CH$_3$, CF$_3$, OCH$_3$, or OCF$_3$; and all other variables are as originally defined or as defined in Embodiment E1 or Embodiment E2 or Embodiment E3.

A ninth embodiment of the present invention (Embodiment E9) is a compound of Formula I, or a pharmaceutically acceptable salt thereof; wherein R$^1$ is AryA wherein AryA is

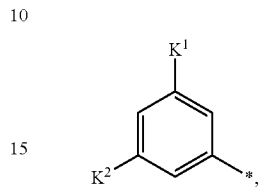

wherein K$^1$ and K$^2$ are each independently Br, Cl, or CN; and all other variables are as originally defined or as defined in Embodiment E1 or Embodiment E2 or Embodiment E3. In a sub-embodiment of this embodiment, AryA is selected from the group consisting of 3-chloro-5-cyanophenyl, 3-bromo-5-chlorophenyl, 3,5-dicyanophenyl, and 3,5-dichlorophenyl.

A tenth embodiment of the present invention (Embodiment E10) is a compound of Formula I, or a pharmaceutically acceptable salt thereof; wherein R$^1$ is AryA wherein AryA is 3-chloro-5-cyanophenyl; and all other variables are as originally defined or as defined in Embodiment E1 or Embodiment E2 or Embodiment E3.

An eleventh embodiment of the present invention (Embodiment E11) is a compound of Formula I, or a pharmaceutically acceptable salt thereof; wherein R$^1$ is HetA; and all other variables are as originally defined or as defined in Embodiment E1 or Embodiment E2 or Embodiment E3.

A twelfth embodiment of the present invention (Embodiment E12) is a compound of Formula I, or a pharmaceutically acceptable salt thereof; wherein R$^1$ is HetA wherein HetA is a heteroaryl as originally defined, wherein the heteroaryl is optionally substituted with a total of from 1 to 8 substituents as defined in HetA as originally defined; and all other variables are as originally defined or as defined in Embodiment E1 or Embodiment E2 or Embodiment E3.

A thirteenth embodiment of the present invention (Embodiment E13) is a compound of Formula I, or a pharmaceutically acceptable salt thereof; wherein R$^1$ is HetA wherein HetA is a 5- or 6-membered heteroaromatic ring containing from 1 to 4 heteroatoms independently selected from N, O and S, wherein each N is optionally in the form of an oxide, wherein the heteroaromatic ring is optionally substituted with from 1 to 3 substituents each of which is independently halogen, CN, NO$_2$, C$_{1-4}$ alkyl, C$_{1-4}$ haloalkyl, C$_{2-4}$ alkenyl, C$_{2-4}$ alkenyl substituted with CN, OH, O—C$_{1-4}$ alkyl, O—C$_{1-4}$ haloalkyl, N(R$^A$)R$^B$, C(O)N(R$^A$)R$^B$, C(O)R$^A$, CO$_2$R$^A$, SR$^A$, S(O)R$^A$, SO$_2$R$^A$, SO$_2$N(R$^A$)R$^B$, or SO$_2$N(R$^A$)C(O)R$^B$; wherein any R$^A$ or R$^B$ which is part of HetA is H or C$_{1-4}$ alkyl; and all other variables are as originally defined or as defined in Embodiment E1 or Embodiment E2 or Embodiment E3.

A fourteenth embodiment of the present invention (Embodiment E14) is a compound of Formula I, or a pharmaceutically acceptable salt thereof; wherein R$^1$ is HetA wherein HetA is a heteroaromatic ring selected from the group consisting of furanyl, thienyl, pyrrolyl, pyrazolyl, imidazolyl, triazolyl, tetrazolyl, oxazolyl, isoxazolyl, thiazolyl, isothiazolyl, oxadiazolyl, thiadiazolyl, pyridyl, pyrimidinyl, pyrazinyl, and pyridazinyl, wherein the heteroaromatic ring is optionally substituted with from 1 to 3 substituents each of which is independently halogen, CN, $NO_2$, $C_{1-4}$ alkyl, $C_{1-4}$ haloalkyl, $C_{2-4}$ alkenyl, $C_{2-4}$ alkenyl substituted with CN, OH, O—$C_{1-4}$ alkyl, O—$C_{1-4}$ haloalkyl, $N(R^A)R^B$, $C(O)N(R^A)R^B$, $C(O)R^A$, $CO_2R^A$, $SR^A$, $S(O)R^A$, $SO_2R^A$, $SO_2N(R^A)R^B$, or $SO_2N(R^A)C(O)R^B$; wherein any $R^A$ or $R^B$ which is part of HetA is H or $C_{1-4}$ alkyl; and all other variables are as originally defined or as defined in Embodiment E1 or Embodiment E2 or Embodiment E3.

A fifteenth embodiment of the present invention (Embodiment E15) is a compound of Formula I, or a pharmaceutically acceptable salt thereof; wherein $R^1$ is HetA wherein HetA is a heteroaromatic ring selected from the group consisting of furanyl, thienyl, pyrrolyl, pyrazolyl, imidazolyl, triazolyl, tetrazolyl, oxazolyl, isoxazolyl, thiazolyl, isothiazolyl, oxadiazolyl, thiadiazolyl, pyridyl, pyrimidinyl, pyrazinyl, and pyridazinyl, wherein the heteroaromatic ring is optionally substituted with from 1 to 3 substituents each of which is independently Cl, Br, F, CN, $NO_2$, $C_{1-4}$ alkyl, $C_{1-4}$ fluoroalkyl, CH=CH—CN, OH, O—$C_{1-4}$ alkyl, O—$C_{1-4}$ fluoroalkyl, $NH_2$, $N(H)CH_3$, $N(CH_3)_2$, $C(O)NH_2$, $C(O)N(H)CH_3$, $C(O)N(CH_3)_2$, $C(O)CH_3$, $CO_2CH_3$, $SCH_3$, $S(O)CH_3$, $SO_2CH_3$, $SO_2NH_2$, $SO_2N(H)CH_3$, or $SO_2N(CH_3)_2$; and all other variables are as originally defined or as defined in Embodiment E1 or Embodiment E2 or Embodiment E3.

A sixteenth embodiment of the present invention (Embodiment E16) is a compound of Formula I, or a pharmaceutically acceptable salt thereof; wherein $R^1$ is HetA wherein HetA is a heteroaromatic ring which is pyridyl or pyrimidinyl, wherein the heteroaromatic ring is optionally substituted with from 1 to 3 substituents each of which is independently Cl, Br, F, $CH_3$, $CF_3$, $OCH_3$, $OCF_3$, $NH_2$, $N(H)CH_3$, $N(CH_3)_2$, $C(O)NH_2$, $C(O)N(H)CH_3$, $C(O)N(CH_3)_2$, $C(O)CH_3$, $CO_2CH_3$, $SCH_3$, $S(O)CH_3$, $SO_2CH_3$, $SO_2NH_2$, $SO_2N(H)CH_3$, or $SO_2N(CH_3)$; and all other variables are as originally defined or as defined in Embodiment E1 or Embodiment E2 or Embodiment E3.

A seventeenth embodiment of the present invention (Embodiment E17) is a compound of Formula I, or a pharmaceutically acceptable salt thereof; wherein:

$R^{2A}$, $R^{2B}$, and $R^{2C}$ are each independently:
(1) H,
(2) $C_{1-4}$ alkyl,
(3) $C_{1-4}$ fluoroalkyl,
(4) $C_{1-6}$ alkyl substituted with OH, O—$C_{1-4}$ alkyl, O—$C_{1-4}$ fluoroalkyl, CN, $NO_2$, $N(R^A)R^B$, $C(O)N(R^A)R^B$, $C(O)R^A$, $CO_2R^A$, or $S(O)_2R^A$,
(5) O—$C_{1-4}$ alkyl,
(6) O—$C_{1-4}$ fluoroalkyl,
(7) halogen,
(8) CN,
(9) $NO_2$,
(10) $N(R^A)R^B$,
(11) $C(O)N(R^A)R^B$,
(12) $C(O)R^A$,
(13) $C(O)$—$C_{1-4}$ fluoroalkyl,
(14) $C(O)OR^A$,
(15) $S(O)_2R^A$;
(16) $N(R^C)R^D$,
(17) $C(O)N(R^C)R^D$,
(18) $C_{3-6}$ cycloalkyl, or
(19) O—$C_{3-6}$ cycloalkyl;
$R^3$ is:
(1) H,
(2) OH,
(3) $C_{1-4}$ alkyl,
(4) $C_{1-4}$ fluoroalkyl,
(5) $C_{1-6}$ alkyl substituted with OH, O—$C_{1-4}$ alkyl, O—$C_{1-4}$ fluoroalkyl, CN, $NO_2$, $N(R^A)R^B$, $C(O)N(R^A)R^B$, $C(O)R^A$, $CO_2R^A$, or $S(O)_2R^A$,
(6) O—$C_{1-4}$ alkyl,
(7) O—$C_{1-4}$ fluoroalkyl,
(8) halogen,
(9) CN,
(10) $NO_2$,
(11) $N(R^A)R^B$,
(12) $C(O)N(R^A)R^B$,
(13) $C(O)R^A$,
(14) $C(O)$—$C_{1-4}$ fluoroalkyl,
(15) $C(O)OR^A$,
(16) $S(O)_2R^A$;
(17) $N(R^C)R^D$,
(18) $C(O)N(R^C)R^D$,
(19) $C_{3-6}$ cycloalkyl, or
(20) O—$C_{3-6}$ cycloalkyl;
wherein any $R^A$ or $R^B$ which is part of $R^{2A}$, $R^{2B}$, $R^{2C}$, or $R^3$ is H or $C_{1-4}$ alkyl;
wherein any pair of $R^C$ and $R^D$ which is part of $R^{2A}$, $R^{2B}$, $R^{2C}$, or $R^3$, together with the N to which the pair is attached, form azetidinyl, pyrrolidinyl, piperidinyl, piperazinyl, morpholinyl, or thiomorpholinyl; wherein any of the rings is optionally substituted with 1 or 2 substituents each of which is independently $C_{1-4}$ alkyl, $C(O)$—$C_{1-4}$ alkyl, $C(O)O$—$C_{1-4}$ alkyl, or $S(O)_2$—$C_{1-4}$ alkyl; and wherein the S in thiomorpholinyl is optionally in the form of S(O) or $S(O)_2$;
and all other variables are as originally defined or as defined in any one of the preceding embodiments.

An eighteenth embodiment of the present invention (Embodiment E18) is a compound of Formula I, or a pharmaceutically acceptable salt thereof; wherein:
$R^{2A}$, $R^{2B}$, and $R^{2C}$ are each independently:
(1) H,
(2) $C_{1-4}$ alkyl,
(3) $CF_3$,
(4) $CH_2CF_3$,
(5) $CH_2OH$,
(6) $CH_2O$—$C_{1-4}$ alkyl,
(7) $CH_2CN$,
(8) $CH_2N(R^A)R^B$,
(9) $CH_2C(O)N(R^A)R^B$,
(10) $CH_2C(O)R^A$,
(11) $CH_2CO_2R^A$,
(12) $CH_2S(O)_2R^A$,
(13) O—$C_{1-4}$ alkyl,
(14) $OCF_3$,
(15) Cl,
(16) Br,
(17) F,
(18) CN,
(19) $NO_2$,
(20) $N(R^A)R^B$,
(21) $C(O)N(R^A)R^B$,
(22) $C(O)R^A$,
(23) $C(O)$—$C_{1-4}$ fluoroalkyl,
(24) $C(O)OR^A$,
(25) $S(O)_2R^A$,

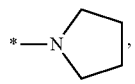 (26)

-continued

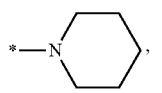

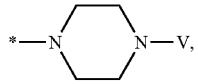

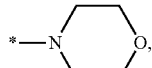

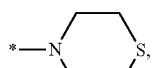

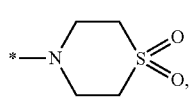

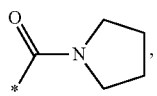

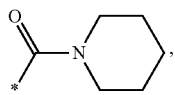

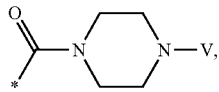

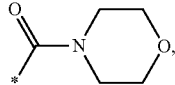

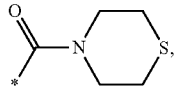

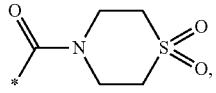

(38) cyclopropyl, or
(39) O-cyclopropyl;
V is H, $CH_3$, $C(O)CH_3$, $C(O)OCH_3$, or $S(O)_2CH_3$;
$R^3$ is:
(1) H,
(2) OH,
(3) $C_{1-4}$ alkyl,
(4) $CF_3$,
(5) O—$C_{1-4}$ alkyl,
(6) $OCF_3$,
(7) Cl,
(8) Br,
(9) F,
(10) CN,
(11) $NO_2$,
(12) $N(R^A)R^B$,
(13) $C(O)N(R^A)R^B$,
(14) $C(O)R^A$,
(15) $C(O)CF_3$,
(16) $C(O)OR^A$,
(17) $OC(O)R^A$,
(18) $SR^A$,
(19) $S(O)_2R^A$, or
(20) $S(O)_2N(R^A)R^B$;
and all other variables are as originally defined or as defined in any one of the preceding embodiments.

A nineteenth embodiment of the present invention (Embodiment E19) is a compound of Formula I, or a pharmaceutically acceptable salt thereof; wherein:
$R^{2A}$, $R^{2B}$, and $R^{2C}$ are each independently:
(1) H,
(2) $C_{1-3}$ alkyl,
(3) $CF_3$,
(4) $CH_2CF_3$,
(5) $CH_2OH$,
(6) $CH_2OCH_3$,
(7) $CH_2CN$,
(8) $CH_2NH_2$,
(9) $CH_2N(H)CH_3$,
(10) $CH_2N(CH_3)_2$,
(11) $CH_2C(O)NH_2$,
(12) $CH_2C(O)N(H)CH_3$,
(13) $CH_2C(O)N(CH_3)_2$,
(14) $CH_2C(O)CH_3$,
(15) $CH_2CO_2CH_3$,
(16) $CH_2S(O)_2CH_3$,
(17) O—$C_{1-3}$ alkyl,
(18) $OCF_3$,
(19) Cl,
(20) Br,
(21) F,
(22) CN,
(23) $NO_2$,
(24) $NH_2$,
(25) $N(H)CH_3$,
(26) $N(CH_3)_2$,
(27) $C(O)NH_2$,
(28) $C(O)N(H)CH_3$,
(29) $C(O)N(CH_3)_2$,
(30) $C(O)CH_3$,
(31) $C(O)CF_3$,
(32) $CO_2CH_3$, or
(33) $S(O)_2CH_3$;
$R^3$ is:
(1) H,
(2) OH,
(3) $C_{1-3}$ alkyl,
(4) $CF_3$,
(5) O—$C_{1-3}$ alkyl,
(6) $OCF_3$,
(7) Cl,
(8) Br,
(9) F,
(10) CN,
(11) $NO_2$,
(12) $NH_2$,
(13) $N(H)CH_3$,
(14) $N(CH_3)_2$,
(15) $C(O)NH_2$,
(16) $C(O)N(H)CH_3$,
(17) $C(O)N(CH_3)_2$,
(18) $C(O)H$,
(19) $C(O)CH_3$,
(20) $C(O)CF_3$,
(21) $C(O)OCH_3$,
(22) $OC(O)CH_3$,

(23) SCH$_3$,
(24) S(O)CH$_3$,
(25) S(O)$_2$CH$_3$, or
(26) S(O)$_2$NH$_2$;
and all other variables are as originally defined or as defined in any one of the preceding embodiments.

A twentieth embodiment of the present invention (Embodiment E20) is a compound of Formula I, or a pharmaceutically acceptable salt thereof; wherein $R^{2A}$, $R^{2B}$, and $R^{2C}$ are each independently H, CH$_3$, CH$_2$CH$_3$, CF$_3$, OCH$_3$, OCF$_3$, Cl, Br, F, or CN; $R^3$ is H, OH, CH$_3$, CH$_2$CH$_3$, CF$_3$, OCH$_3$, OCF$_3$, Cl, Br, F, or CN; and all other variables are as originally defined or as defined in any one of the preceding embodiments.

A twenty-first embodiment of the present invention (Embodiment E21) is a compound of Formula I, or a pharmaceutically acceptable salt thereof; wherein $R^{2A}$, $R^{2B}$, and $R^{2C}$ are each independently H, CH$_3$, Cl, Br, F, or CN; $R^3$ is H, OH, CH$_3$, Cl, Br, F, or CN; and all other variables are as originally defined or as defined in any one of the preceding embodiments.

A twenty-second embodiment of the present invention (Embodiment E22) is a compound of Formula I, or a pharmaceutically acceptable salt thereof; wherein $R^{2A}$, $R^{2B}$, and $R^{2C}$ are each independently H, CH$_3$, Cl, Br, F, or CN; $R^3$ is H, OH, CH$_3$, or F; and all other variables are as originally defined or as defined in any one of the preceding embodiments.

A twenty-third embodiment of the present invention (Embodiment E23) is a compound of Formula I, or a pharmaceutically acceptable salt thereof; wherein $R^{2A}$, $R^{2B}$, and $R^{2C}$ are each independently is H, Cl, or F; $R^3$ is H, OH, CH$_3$, Cl, or F; and all other variables are as originally defined or as defined in any one of the preceding embodiments.

A twenty-fourth embodiment of the present invention (Embodiment E24) is a compound of Formula I, or a pharmaceutically acceptable salt thereof; wherein $R^{2B}$ and $R^{2C}$ are each independently is H, CH$_3$, CF$_3$, Cl, Br, F or CN; and all other variables are as originally defined or as defined in any one of the preceding embodiments. In a sub-embodiment of this embodiment, $R^{2B}$ and $R^{2C}$ are each independently is H, CH$_3$, Cl, Br, F or CN. In another sub-embodiment of this embodiment, $R^{2B}$ is H, CH$_3$, CF$_3$, or Cl; and $R^{2C}$ is H, CH$_3$, or Cl.

A twenty-fifth embodiment of the present invention (Embodiment E25) is a compound of Formula I, or a pharmaceutically acceptable salt thereof; wherein $R^E$ and $R^F$ are each independently H, C$_{1-4}$ alkyl, Br, Cl, F, CN or C$_{1-4}$ fluoroalkyl; and all other variables are as originally defined or as defined in any one of the preceding embodiments. In a sub-embodiment of this embodiment, $R^E$ and $R^F$ are each independently H, C$_{1-4}$ alkyl, Br, Cl, F, CN or CF$_3$. In another sub-embodiment of this embodiment, $R^E$ and $R^F$ are each independently H, CH$_3$, Br, Cl, F, CN or CF$_3$.

A twenty-sixth embodiment of the present invention (Embodiment E26) is a compound of Formula I, or a pharmaceutically acceptable salt thereof; wherein $R^E$ and $R^F$ are each independently H, C$_{1-4}$ alkyl, Br, Cl, F, or CN; and all other variables are as originally defined or as defined in any one of the preceding embodiments.

A twenty-seventh embodiment of the present invention (Embodiment E27) is a compound of Formula I, or a pharmaceutically acceptable salt thereof; wherein $R^E$ and $R^F$ are each independently H, CH$_3$, Br, Cl, F, or CN; and all other variables are as originally defined or as defined in any one of the preceding embodiments.

A twenty-eighth embodiment of the present invention (Embodiment E28) is a compound of Formula I, or a pharmaceutically acceptable salt thereof; wherein $R^E$ and $R^F$ are each independently H, Br, Cl, F, or CN; and all other variables are as originally defined or as defined in any one of the preceding embodiments.

A twenty-ninth embodiment of the present invention (Embodiment E29) is a compound of Formula I, or a pharmaceutically acceptable salt thereof; wherein $R^E$ and $R^F$ are each independently H, Br, Cl, or F; and all other variables are as originally defined or as defined in any one of the preceding embodiments.

A thirtieth embodiment of the present invention (Embodiment E30) is a compound of Formula I, or a pharmaceutically acceptable salt thereof, wherein the compound of Formula I is a compound of Formula II (alternatively referred to as "Compound II"):

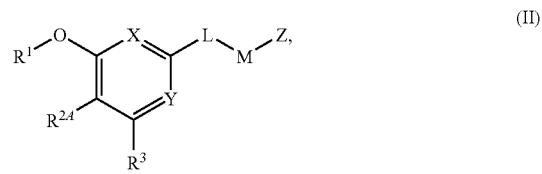

wherein X is N, CH, C(—C$_{1-4}$ alkyl), C(Br), C(Cl), C(F), C(CN) or C(CF$_3$); and Y is N, CH, C(—C$_{1-4}$ alkyl), C(Br), C(Cl), C(F), C(CN) or C(CF$_3$), with the proviso that either one of X and Y is N or both X and Y are N; and all other variables are as originally defined or as defined in any one of the preceding embodiments. In a sub-embodiment of this embodiment, X is N; and Y is CH, C(CH$_3$), C(Br), C(Cl), C(F), C(CN) or C(CF$_3$) in Compound II. In another sub-embodiment, X is CH, C(CH$_3$), C(Br), C(Cl), C(F), C(CN) or C(CF$_3$); and Y is N.

A thirty-first embodiment of the present invention (Embodiment E31) is a compound of Formula I, or a pharmaceutically acceptable salt thereof, wherein the compound of Formula I is a compound of Formula II, wherein X is N, CH, C(—C$_{1-4}$ alkyl), C(Br), C(Cl), C(F), or C(CN); and Y is N, CH, C(—C$_{1-4}$ alkyl), C(Br), C(Cl), C(F), or C(CN), with the proviso that either one of X and Y is N or both X and Y are N; and all other variables are as originally defined or as defined in any one of the preceding embodiments. In a sub-embodiment of this embodiment, X is N; and Y is CH, C(CH$_3$), C(Br), C(Cl), C(F), or C(CN) in Compound II. In another sub-embodiment of this embodiment, X is N; and Y is CH, C(Cl), or C(F) in Compound II. In another sub-embodiment, X is CH, C(CH$_3$), C(Br), C(Cl), C(F), or C(CN); and Y is N. In still another sub-embodiment, X is CH, C(Cl), or C(F); and Y is N.

A thirty-second embodiment of the present invention (Embodiment E32) is a compound of Formula I, or a pharmaceutically acceptable salt thereof, wherein L is a single bond that attaches M directly to ring A, O, N(H), N(CH$_3$), CH$_2$, or CH(CH$_3$); M is CH$_2$, CH(CH$_3$), or CH(OH); and all other variables are as originally defined or as defined in any one of the preceding embodiments.

A thirty-third embodiment of the present invention (Embodiment E33) is a compound of Formula I, or a pharmaceutically acceptable salt thereof, wherein L is a single bond that attaches M directly to ring A, O, N(H), N(CH$_3$), CH$_2$, or CH(CH$_3$); M is CH$_2$ or CH(CH$_3$); and all other variables are as originally defined or as defined in any one of the preceding embodiments.

A thirty-fourth embodiment of the present invention (Embodiment E34) is a compound of Formula I, or a pharmaceutically acceptable salt thereof, wherein L is a single bond that attaches M directly to ring A, O, N(H), or CH₂; M is CH₂ or CH(OH); and all other variables are as originally defined or as defined in any one of the preceding embodiments.

A thirty-fifth embodiment of the present invention (Embodiment E35) is a compound of Formula I, or a pharmaceutically acceptable salt thereof, wherein L is a single bond that attaches M directly to ring A, O, N(H), or CH₂; M is CH₂; and all other variables are as originally defined or as defined in any one of the preceding embodiments.

A thirty-sixth embodiment of the present invention (Embodiment E36) is a compound of Formula I, or a pharmaceutically acceptable salt thereof, wherein L is O, N(H), or CH₂; M is CH₂; and all other variables are as originally defined or as defined in any one of the preceding embodiments.

A thirty-seventh embodiment of the present invention (Embodiment E37) is a compound of Formula I, or a pharmaceutically acceptable salt thereof, wherein L is a single bond that attaches ring A directly to M, CH₂, or CH(CH₃); M is CH₂ or CH(CH₃); and all other variables are as originally defined or as defined in any one of the preceding embodiments.

A thirty-eighth embodiment of the present invention (Embodiment E38) is a compound of Formula I, or a pharmaceutically acceptable salt thereof, wherein L is CH₂; M is CH₂; and all other variables are as originally defined or as defined in any one of the preceding embodiments.

A thirty-ninth embodiment of the present invention (Embodiment E39) is a compound of Formula I, or a pharmaceutically acceptable salt thereof, wherein L is CH₂ or CH(CH₃); M is C(O)NH or C(O)N(CH₃); and all other variables are as originally defined or as defined in any one of the preceding embodiments.

A fortieth embodiment of the present invention (Embodiment E40) is a compound of Formula I, or a pharmaceutically acceptable salt thereof, wherein Z is G¹ or G²;

G¹ is:

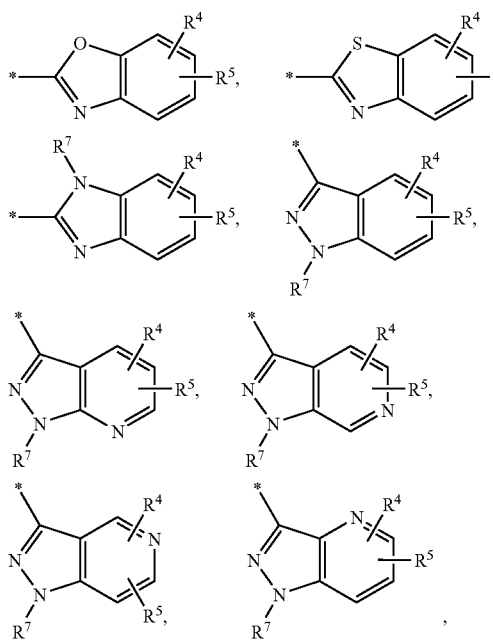

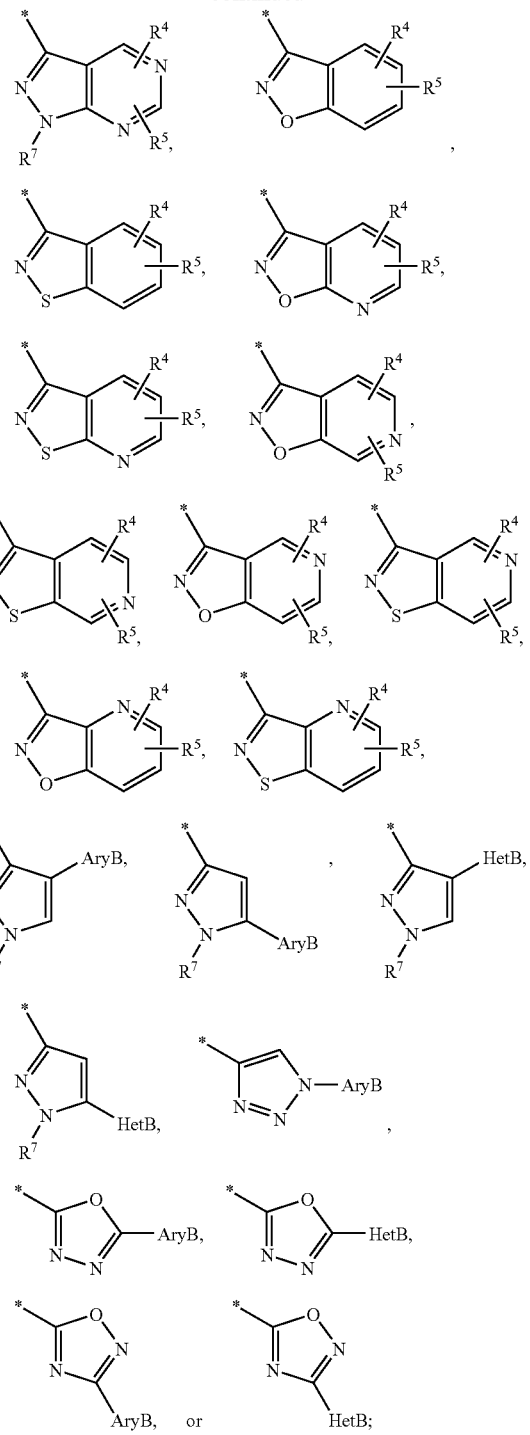

G² is:

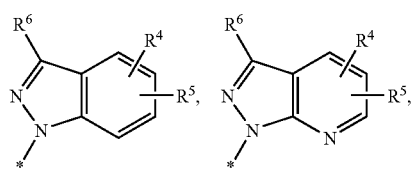

-continued

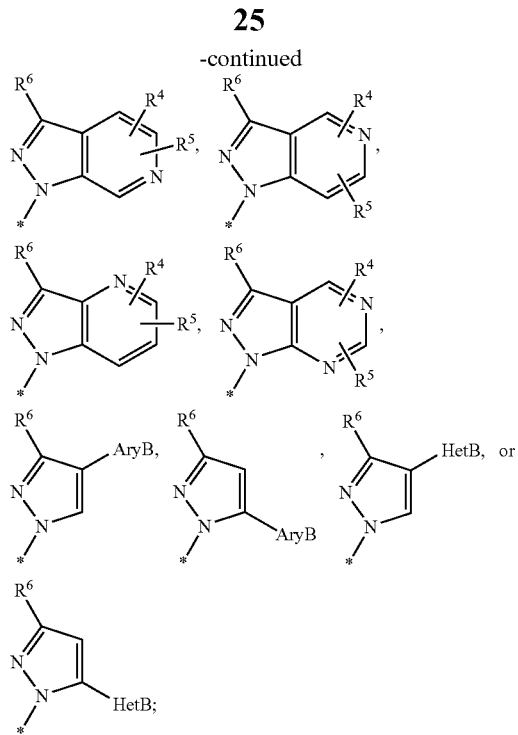

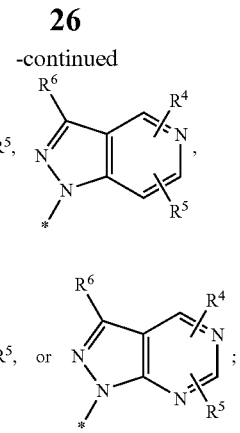

and all other variables are as originally defined or as defined in any one of the preceding embodiments.

A forty-first embodiment of the present invention (Embodiment E41) is a compound of Formula I, or a pharmaceutically acceptable salt thereof, wherein Z is $G^1$ or $G^2$;
$G^1$ is:

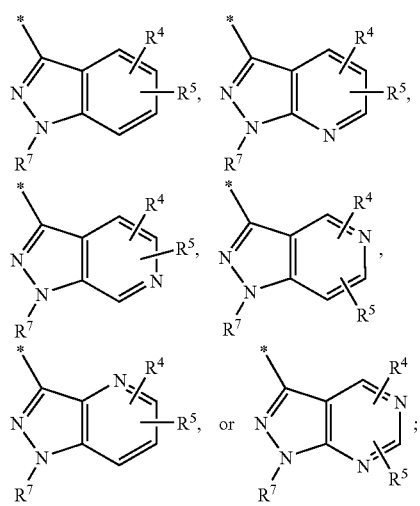

$G^2$ is:

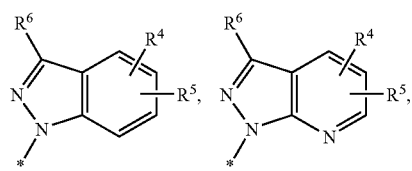

and all other variables are as originally defined or as defined in any one of the preceding embodiments.

A forty-second embodiment of the present invention (Embodiment E42) is a compound of Formula I, or a pharmaceutically acceptable salt thereof, wherein Z is $G^1$, which is:

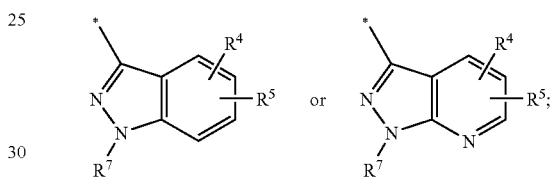

and all other variables are as originally defined or as defined in any one of the preceding embodiments.

A forty-third embodiment of the present invention (Embodiment E43) is a compound of Formula I, or a pharmaceutically acceptable salt thereof, wherein Z is $G^1$, which is:

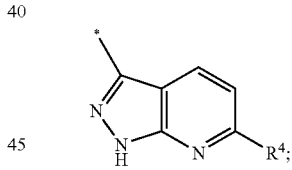

and all other variables are as originally defined or as defined in any one of the preceding embodiments.

A forty-fourth embodiment of the present invention (Embodiment E44) is a compound of Formula I, or a pharmaceutically acceptable salt thereof, wherein Z is $G^4$, which is:

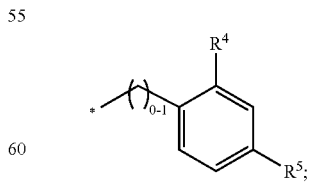

and all other variables are as originally defined or as defined in any one of the preceding embodiments.

A forty-fifth embodiment of the present invention (Embodiment E45) is a compound of Formula I, or a pharmaceutically acceptable salt thereof, wherein $R^4$ and $R^5$ are each independently:
(1) H,
(2) $C_{1-4}$ alkyl,
(3) $C_{1-4}$ fluoroalkyl,
(4) $C_{1-6}$ alkyl substituted with OH, O—$C_{1-4}$ alkyl, O—$C_{1-4}$ fluoroalkyl, CN, $NO_2$, $N(R^A)R^B$, $C(O)N(R^A)R^B$, $C(O)R^A$, $CO_2R^A$, or $S(O)_2R^A$,
(5) O—$C_{1-4}$ alkyl,
(6) O—$C_{1-4}$ fluoroalkyl,
(7) halogen,
(8) CN,
(9) $NO_2$,
(10) $N(R^A)R^B$,
(11) $C(O)N(R^A)R^B$,
(12) $C(O)R^A$,
(13) $C(O)$—$C_{1-4}$ fluoroalkyl,
(14) $C(O)OR^A$,
(15) $S(O)_2R^A$;
(16) $N(R^C)R^D$,
(17) $C(O)N(R^C)R^D$,
(18) $C_{3-6}$ cycloalkyl,
(19) O—$C_{3-6}$ cycloalkyl, or
(20) OH, or
(21) imidazolyl;
any $R^A$ or $R^B$ which is part of either $R^4$ or $R^5$ is H or $C_{1-4}$ alkyl;
any pair of $R^C$ and $R^D$ which is part of either $R^4$ or $R^5$, together with the N to which the pair is attached, form azetidinyl, pyrrolidinyl, piperidinyl, piperazinyl, morpholinyl, or thiomorpholinyl; wherein any of the rings is optionally substituted with 1 or 2 substituents each of which is independently $C_{1-4}$ alkyl, $C(O)R^A$, $C(O)OR^A$, $C(O)N(R^A)R^B$, or $S(O)_2R^A$; and wherein the S in thiomorpholinyl is optionally in the form of S(O) or $S(O)_2$;
and all other variables are as originally defined or as defined in any one of the preceding embodiments. In a first sub-embodiment of Embodiment E45, $R^4$ and $R^5$ are each independently selected from groups (1) to (20) as originally defined in Embodiment E45 (i.e., this sub-embodiment excludes (21) imidazolyl); and all other variables are as originally defined in Embodiment E45.

A forty-sixth embodiment of the present invention (Embodiment E46) is a compound of Formula I, or a pharmaceutically acceptable salt thereof, wherein $R^4$ and $R^5$ are each independently:
(1) H,
(2) $C_{1-4}$ alkyl,
(3) $CF_3$,
(4) $CH_2CF_3$,
(5) $CH_2OH$,
(6) $CH_2O$—$C_{1-4}$ alkyl,
(7) $CH_2CN$,
(8) $CH_2N(R^A)R^B$,
(9) $CH_2C(O)N(R^A)R^B$,
(10) $CH_2C(O)R^A$,
(11) $CH_2CO_2R^A$,
(12) $CH_2S(O)_2R^A$,
(13) O—$C_{1-4}$ alkyl,
(14) $OCF_3$,
(15) Cl,
(16) Br,
(17) F,
(18) CN,
(19) $NO_2$,
(20) $N(R^A)R^B$,
(21) $C(O)N(R^A)R^B$,
(22) $C(O)R^A$,
(23) $C(O)$—$C_{1-4}$ fluoroalkyl,
(24) $C(O)OR^A$,
(25) $S(O)_2R^A$,

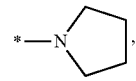
(26)

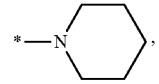
(27)

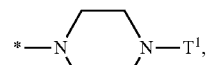
(28)

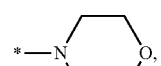
(29)

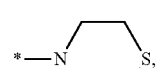
(30)

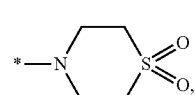
(31)

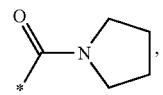
(32)

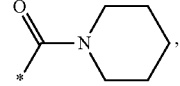
(33)

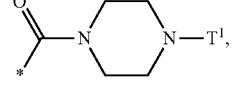
(34)

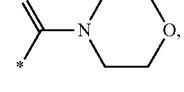
(35)

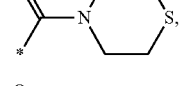
(36)

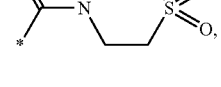
(37)

(38) cyclopropyl,
(39) O-cyclopropyl, or
(40) OH, or
(41) imidazolyl;
each $T^1$ is independently H, $C_{1-4}$ alkyl, $C(O)R^A$, $C(O)O R^A$, $C(O)N(R^A)R^B$, or $S(O)_2R^A$;
and all other variables are as originally defined or as defined in any one of the preceding embodiments. In a first sub-embodiment of this embodiment, each T1 is independently H, $C_{1-4}$ alkyl, $C(O)$—$C_{1-4}$ alkyl, $C(O)O$—$C_{1-4}$ alkyl, $C(O)N($—$C_{1-4}$ alkyl$)_2$, or $S(O)_2$—$C_{1-4}$ alkyl. In a second sub-embodiment of this embodiment, each T1 is independently H, CH₃, C(O)CH₃, C(O)OCH₃, C(O)N(CH₃)₂, or S(O)₂CH₃. In a third sub-embodiment of Embodiment E46, $R^4$ and $R^5$ are each independently selected from groups (1) to (40) as originally defined in Embodiment E46 (i.e., this sub-embodiment excludes (41) imidazolyl); and all other variables are as originally defined in Embodiment E46 or as defined in either one of the first and second sub-embodiments.

A forty-seventh embodiment of the present invention (Embodiment E47) is a compound of Formula I, or a pharmaceutically acceptable salt thereof, wherein $R^4$ and $R^5$ are each independently:
(1) H,
(2) $C_{1-3}$ alkyl,
(3) $CF_3$,
(4) $CH_2CF_3$,
(5) $CH_2OH$,
(6) $CH_2OCH_3$,
(7) $CH_2CN$,
(8) $CH_2NH_2$,
(9) $CH_2N(H)CH_3$,
(10) $CH_2N(CH_3)_2$,
(11) $CH_2C(O)NH_2$,
(12) $CH_2C(O)N(H)CH_3$,
(13) $CH_2C(O)N(CH_3)_2$,
(14) $CH_2C(O)CH_3$,
(15) $CH_2CO_2CH_3$,
(16) $CH_2S(O)_2CH_3$,
(17) O—$C_{1-3}$ alkyl,
(18) $OCF_3$,
(19) Cl,
(20) Br,
(21) F,
(22) CN,
(23) $NO_2$,
(24) $NH_2$,
(25) $N(H)CH_3$,
(26) $N(CH_3)_2$,
(27) $C(O)NH_2$,
(28) $C(O)N(H)CH_3$,
(29) $C(O)N(CH_3)_2$,
(30) $C(O)CH_3$,
(31) $C(O)CF_3$,
(32) $CO_2CH_3$,
(33) $S(O)_2CH_3$, or
(34) OH;
and all other variables are as originally defined or as defined in any one of the preceding embodiments.

A forty-eighth embodiment of the present invention (Embodiment E48) is a compound of Formula I, or a pharmaceutically acceptable salt thereof, wherein $R^4$ and $R^5$ are each independently H, $CH_3$, $CH_2CH_3$, $CF_3$, $OCH_3$, $OCF_3$, Cl, Br, F, CN, $NH_2$, $N(H)CH_3$, $N(CH_3)_2$, or OH; and all other variables are as originally defined or as defined in any one of the preceding embodiments.

A forty-ninth embodiment of the present invention (Embodiment E49) is a compound of Formula I, or a pharmaceutically acceptable salt thereof, wherein $R^4$ is H, $CH_3$, $CF_3$, $OCH_3$, $OCF_3$, Cl, Br, F, CN, or $NH_2$; $R^5$ is H; and all other variables are as originally defined or as defined in any one of the preceding embodiments.

A fiftieth embodiment of the present invention (Embodiment E50) is a compound of Formula I, or a pharmaceutically acceptable salt thereof, wherein $R^4$ is H or $NH_2$; $R^5$ is H; and all other variables are as originally defined or as defined in any one of the preceding embodiments.

A fifty-first embodiment of the present invention (Embodiment E51) is a compound of Formula I, or a pharmaceutically acceptable salt thereof, wherein $R^4$ is H, $CH_3$, Cl, or Br; $R^5$ is H, Cl, Br, $S(O)_2NH_2$, or $C(O)NH_2$; and provided that $R^4$ and $R^5$ are not both H; and all other variables are as originally defined or as defined in any one of the preceding embodiments.

A fifty-second embodiment of the present invention (Embodiment E52) is a compound of Formula I, or a pharmaceutically acceptable salt thereof, wherein $R^6$ is:
(1) H,
(2) $C_{1-4}$ alkyl,
(3) OH,
(4) O—$C_{1-4}$ alkyl,
(5) $NH_2$,
(6) N(H)—$C_{1-4}$ alkyl,
(7) N(—$C_{1-4}$ alkyl)₂, or
(8) a saturated heterocyclic ring selected from the group consisting of 1-azetidinyl, 1-pyrrolidinyl, 1-piperidinyl, 1-piperazinyl, 1-azepanyl, 4-morpholinyl, and 4-thiomorpholinyl wherein the S in the ring is optionally S(O) or $S(O)_2$, wherein the heterocyclic ring is optionally substituted with 1 or 2 substituents each of which is independently $C_{1-4}$ alkyl, C(O)—$C_{1-4}$ alkyl, C(O)O—$C_{1-4}$ alkyl C(O)NH₂, C(O)NH(—$C_{1-4}$ alkyl), C(O)N(—$C_{1-4}$ alkyl)₂, or S(O)₂—$C_{1-4}$ alkyl;
and all other variables are as originally defined or as defined in any one of the preceding embodiments.

A fifty-third embodiment of the present invention (Embodiment E53) is a compound of Formula I, or a pharmaceutically acceptable salt thereof, wherein $R^6$ is:
(1) H,
(2) $C_{1-3}$ alkyl,
(3) OH,
(4) $C(O)N(H)CH_3$,
(29) $C(O)N(CH_3)_2$,
(30) $C(O)CH_3$,
(32) $CO_2CH_3$,
(33) $S(O)_2CH_3$, or

(26)

(27)

(28)

wherein $T^2$ is $CH_3$, $C(O)CH_3$, $C(O)OCH_3$, $C(O)N(CH_3)_2$, or $S(O)_2CH_3$,

(29)

(30)

(31)

and all other variables are as originally defined or as defined in any one of the preceding embodiments.

A fifty-fourth embodiment of the present invention (Embodiment E54) is a compound of Formula I, or a pharmaceutically acceptable salt thereof, wherein $R^6$ is H or $C_{1-3}$ alkyl; and all other variables are as originally defined or as defined in any one of the preceding embodiments.

A fifty-fifth embodiment of the present invention (Embodiment E55) is a compound of Formula I, or a pharmaceutically acceptable salt thereof, wherein $R^6$ is H or $CH_3$; and all other variables are as originally defined or as defined in any one of the preceding embodiments.

A fifty-sixth embodiment of the present invention (Embodiment E56) is a compound of Formula I, or a pharmaceutically acceptable salt thereof, wherein $R^6$ is H; and all other variables are as originally defined or as defined in any one of the preceding embodiments.

A fifty-seventh embodiment of the present invention (Embodiment E57) is a compound of Formula I, or a pharmaceutically acceptable salt thereof, wherein $R^7$ and $R^{7''}$ are each independently H or $C_{1-4}$ alkyl; and all other variables are as originally defined or as defined in any one of the preceding embodiments.

A fifty-eighth embodiment of the present invention (Embodiment E58) is a compound of Formula I, or a pharmaceutically acceptable salt thereof, wherein $R^7$ is H or $C_{1-4}$ alkyl and $R^{7''}$ is H; and all other variables are as originally defined or as defined in any one of the preceding embodiments.

A fifty-ninth embodiment of the present invention (Embodiment E59) is a compound of Formula I, or a pharmaceutically acceptable salt thereof, wherein $R^7$ and $R^{7''}$ are each independently H or $CH_3$; and all other variables are as originally defined or as defined in any one of the preceding embodiments.

A sixtieth embodiment of the present invention (Embodiment E60) is a compound of Formula I, or a pharmaceutically acceptable salt thereof, wherein $R^7$ is H or $CH_3$ and $R^{7''}$ is H; and all other variables are as originally defined or as defined in any one of the preceding embodiments.

A sixty-first embodiment of the present invention (Embodiment E61) is a compound of Formula I, or a pharmaceutically acceptable salt thereof, wherein $R^7$ and $R^{7''}$ are both H; and all other variables are as originally defined or as defined in any one of the preceding embodiments.

A sixty-second embodiment of the present invention (Embodiment E62) is a compound of Formula I, or a pharmaceutically acceptable salt thereof, wherein AryB is phenyl or naphthyl, wherein the phenyl or naphthyl is optionally substituted with from 1 to 3 substituents each of which is independently halogen, CN, $NO_2$, $C_{1-4}$ alkyl, $C_{1-4}$ haloalkyl, OH, O—$C_{1-4}$ alkyl, O—$C_{1-4}$ haloalkyl, $N(R^A)R^B$, $C(O)N(R^A)R^B$, $C(O)R^A$, $CO_2R^A$, $SR^A$, $S(O)R^A$, $SO_2R^A$, $SO_2N(R^A)R^B$, or $SO_2N(R^A)C(O)R^B$; any $R^A$ or $R^B$ which is part of a substituent in AryB is H or $C_{1-4}$ alkyl; and all other variables are as originally defined or as defined in any one of the preceding embodiments.

A sixty-third embodiment of the present invention (Embodiment E63) is a compound of Formula I, or a pharmaceutically acceptable salt thereof, wherein AryB is phenyl, which is optionally substituted with from 1 to 3 substituents each of which is independently Cl, Br, F, CN, $CH_3$, $CF_3$, OH, $OCH_3$, $OCF_3$, $NH_2$, $N(H)CH_3$, $N(CH_3)_2$, $C(O)NH_2$, $C(O)N(H)CH_3$, $C(O)N(CH_3)_2$, $C(O)CH_3$, $C(O)CF_3$, $CO_2CH_3$, $S(O)_2CH_3$, or $SO_2NH_2$; and all other variables are as originally defined or as defined in any one of the preceding embodiments.

A sixty-fourth embodiment of the present invention (Embodiment E64) is a compound of Formula I, or a pharmaceutically acceptable salt thereof, wherein AryB is phenyl, which is optionally substituted with from 1 or 2 substituents each of which is independently Cl, Br, F, CN, $CH_3$, $CF_3$, OH, $OCH_3$, or $OCF_3$; and all other variables are as originally defined or as defined in any one of the preceding embodiments.

A sixty-fifth embodiment of the present invention (Embodiment E65) is a compound of Formula I, or a pharmaceutically acceptable salt thereof, wherein HetB is a heteroaromatic ring selected from the group consisting of pyrrolyl, pyrazolyl, oxazolyl, isoxazolyl, thiazolyl, isothiazolyl, triazolyl, pyridine, pyrimidine, and pyrazine, wherein the heteroaromatic ring is optionally substituted with from 1 to 3 substituents each of which is independently halogen, CN, $NO_2$, $C_{1-4}$ alkyl, $C_{1-4}$ haloalkyl, OH, O—$C_{1-4}$ alkyl, O—$C_{1-4}$ haloalkyl, $N(R^A)R^B$, $C(O)N(R^A)R^B$, $C(O)R^A$, $CO_2R^A$, $SR^A$, $S(O)R^A$, $SO_2R^A$, $SO_2N(R^A)R^B$, $SO_2N(R^A)C(O)R^B$, or OH; any $R^A$ or $R^B$ which is part of a substituent in HetB is H or $C_{1-4}$ alkyl; and all other variables are as originally defined or as defined in any one of the preceding embodiments.

A sixty-sixth embodiment of the present invention (Embodiment E66) is a compound of Formula I, or a pharmaceutically acceptable salt thereof, wherein HetB is a heteroaromatic ring selected from the group consisting of pyrrolyl, pyrazolyl, oxazolyl, isoxazolyl, thiazolyl, isothiazolyl, triazolyl, pyridine, pyrimidine, and pyrazine, wherein the heteroaromatic ring is optionally substituted with from 1 to 3 substituents each of which is independently Cl, Br, F, CN, $CH_3$, $CF_3$, OH, $OCH_3$, $OCF_3$, $NH_2$, $N(H)CH_3$, $N(CH_3)_2$, $C(O)NH_2$, $C(O)N(H)CH_3$, $C(O)N(CH_3)_2$, $C(O)CH_3$, $C(O)CF_3$, $CO_2CH_3$, $S(O)_2CH_3$, or $SO_2NH_2$; and all other variables are as originally defined or as defined in any one of the preceding embodiments.

A sixty-seventh embodiment of the present invention (Embodiment E67) is a compound of Formula I, or a pharmaceutically acceptable salt thereof, wherein HetB is pyridinyl which is optionally substituted with 1 or 2 substituents each of which is independently Cl, Br, F, CN, $CH_3$, $CF_3$, OH, $OCH_3$, or $OCF_3$; and all other variables are as originally defined or as defined in any one of the preceding embodiments.

A sixty-eighth embodiment of the present invention (Embodiment E68) is a compound of Formula I, or a pharmaceutically acceptable salt thereof, wherein $R^A$ and $R^B$ are each independently H or $C_{1-4}$ alkyl; and all other variables are as originally defined or as defined in any of the preceding embodiments.

A sixty-ninth embodiment of the present invention (Embodiment E69) is a compound of Formula I, or a pharmaceutically acceptable salt thereof, wherein $R^A$ and $R^B$ are each independently H or $CH_3$; and all other variables are as originally defined or as defined in any of the preceding embodiments.

A seventieth embodiment of the present invention (Embodiment E70) is a compound of Formula I, or a pharmaceutically acceptable salt thereof, wherein $R^C$ and $R^D$ are each independently H or $C_{1-4}$ alkyl; or alternatively and independently each pair of $R^C$ and $R^D$ together with the N atom to which they are both attached form a 4-to 7-membered, saturated monocyclic ring optionally containing 1 heteroatom in addition to the nitrogen attached to $R^C$ and $R^D$ selected from N, O, and S, where the S is optionally oxidized to S(O) or S(O)$_2$; and wherein the monocyclic ring is optionally substituted with 1 or 2 substituents each of which is independently C$_{1-4}$ alkyl, C(O)N(R$^A$)R$^B$, C(O)R$^A$, C(O)OR$^A$, or S(O)$_2$R$^A$; and all other variables are as originally defined or as defined in any of the preceding embodiments.

A seventy-first embodiment of the present invention (Embodiment E71) is a compound of Formula I, or a pharmaceutically acceptable salt thereof, wherein R$^C$ and R$^D$ are each independently H or C$_{1-4}$ alkyl; or alternatively and independently each pair of R$^C$ and R$^D$ together with the N atom to which they are both attached form a saturated monocyclic ring selected from the group consisting of

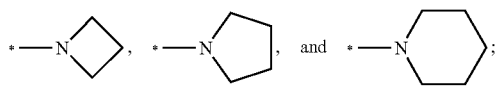

and all other variables are as originally defined or as defined in any of the preceding embodiments.

A seventy-second embodiment of the present invention (Embodiment E72) is a compound of Formula I, or a pharmaceutically acceptable salt thereof, wherein R$^C$ and R$^D$ are each independently H or C$_{1-4}$ alkyl; and all other variables are as originally defined or as defined in any of the preceding embodiments.

A seventy-third embodiment of the present invention (Embodiment E73) is a compound of Formula I, or a pharmaceutically acceptable salt thereof, wherein R$^C$ and R$^D$ are each independently H or CH$_3$; and all other variables are as originally defined or as defined in any of the preceding embodiments.

A seventy-fourth embodiment of the present invention (Embodiment E74) is a compound of Formula I, or a pharmaceutically acceptable salt thereof, wherein R$^8$, R$^9$ and R$^{10}$ are each independently H or C$_{1-4}$ alkyl; and all other variables are as originally defined or as defined in any of the preceding embodiments.

A seventy-fifth embodiment of the present invention (Embodiment E75) is a compound of Formula I, or a pharmaceutically acceptable salt thereof, wherein R$^8$, R$^9$ and R$^{10}$ are each independently H or CH$_3$; and all other variables are as originally defined or as defined in any of the preceding embodiments.

A seventy-sixth embodiment of the present invention (Embodiment E76) is a compound of Formula I, or a pharmaceutically acceptable salt thereof, wherein R$^8$ is H or CH$_3$; R$^9$ and R$^{10}$ are both H; and all other variables are as originally defined or as defined in any of the preceding embodiments.

Unless it is expressly stated to the contrary or otherwise is clear from the context, the provisos set forth in the definition of Compound I in the Summary of the Invention apply to the preceding and subsequent embodiments herein. It is clear from the context, for example, that when any one of Embodiments E40 to E43 is incorporated into the definition of Compound I as originally defined, neither proviso A nor proviso B applies, whereas provisos a, b and c associated with the definitions of L, M and Z do apply. Furthermore, to the extent any embodiment refers back to and incorporates Embodiment E2 or Embodiment E3, it includes the provisos A and B set forth therein. It is understood, however, that the definitions of variables in the provisos can be customized to reflect the definitions of variables in the embodiments being incorporated therein. For example, when Embodiment E61 (i.e., R$^7$ and R$^{7"}$ are both H) is incorporated into Embodiment E3, the proviso can be adjusted to read as follows—and provided that:

(A) when ring A is ring ii-a, X is C(R$^E$) and Y is N, then G$^2$ is not

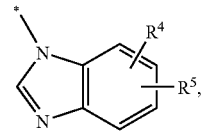

and (B) the compound of Formula I is not 6-methyl-6'-phenoxy-2,2'-methylenedipyridine.

As another example, when Embodiment E31 (i.e., the compound is a compound of Formula II) is incorporated into the definition of Compound I as defined Embodiment E1, the proviso associated with the definitions of L, M and Z applies and can be adjusted to read as follows—and provided that (a) when Z is G$^2$ or G$^3$, then L is a single bond that attaches the ring carbon between X and Y directly to M, CH$_2$, CH(CH$_3$), or C(CH$_3$)$_2$, and M is CH$_2$, CH(CH$_3$), or C(CH$_3$)$_2$.

As still another example, when Embodiment E41 is incorporated into the definition of Compound I as defined in Embodiment E1, the provisos associated with the definitions of L, M and Z apply and can be adjusted to read as follows—and provided that:

(a) when Z is G$^2$ and ring A is ii-a or ii-b or ii-d or ii-e, then L is a single bond that attaches ring A directly to M, CH$_2$, CH(CH$_3$), or C(CH$_3$)$_2$, and M is CH$_2$, CH(CH$_3$), or C(CH$_3$)$_2$, (b) when Z is G$^2$ and ring A is ii-c, then L is CH$_2$, CH(CH$_3$), or C(CH$_3$)$_2$, and M is CH$_2$, CH(CH$_3$), or C(CH$_3$)$_2$, and (c) when Z is G$^1$ and ring A is ii-c, then L is a single bond that attaches ring A directly to M, CH$_2$, CH(CH$_3$), or C(CH$_3$)$_2$, and M is CH$_2$, CH(CH$_3$), or C(CH$_3$)$_2$.

A first class of compounds of the present invention (alternatively referred to herein as Class C1) includes compounds of Formula II and pharmaceutically acceptable salts thereof, wherein:

R$^1$ is as defined in Embodiment E6;

R$^{2A}$ and V (which is part of the definition of R$^{2A}$) are each as defined in Embodiment E18;

R$^3$ is as defined in Embodiment E18;

X is N, CH, C(—C$_{1-4}$ alkyl), C(Br), C(Cl), C(F), C(CN), or C(CF$_3$);

Y is N, CH, C(—C$_{1-4}$ alkyl), C(Br), C(Cl), C(F), C(CN), or C(CF$_3$); and with the proviso that either one of X and Y is N or both X and Y are N;

L is a single bond that attaches the ring carbon between X and Y directly to M, O, N(H), N(CH$_3$), CH$_2$, or CH(CH$_3$);

M is CH$_2$, CH(CH$_3$), or CH(OH);

Z, G$^1$ and G$^2$ are each as defined in Embodiment E41 (wherein the proviso associated with the definitions L, M and Z is modified to read as follows: and provided that when Z is G$^2$, then L is a single bond that attaches the ring carbon between X and Y directly to M, CH$_2$, or CH(CH$_3$), and M is CH$_2$ or CH(CH$_3$));

R$^4$, R$^5$ and T$^1$ (which is part of the definition of R$^4$ and R$^5$) are each as defined in Embodiment E46;

R$^6$ is as defined in Embodiment E52;

R$^7$ is H or C$_{1-4}$ alkyl;

each R$^A$ is independently H or C$_{1-4}$ alkyl; and each R$^B$ is independently H or C$_{1-4}$ alkyl.

A first sub-class of the first class (alternatively referred to herein as "Sub-class C1-S1") includes compounds of Formula II and pharmaceutically acceptable salts thereof, wherein:

X is N, CH, C(—C$_{1-4}$ alkyl), C(Br), C(Cl), C(F), or C(CN);

Y is N, CH, C(—C$_{1-4}$ alkyl), C(Br), C(Cl), C(F), or C(CN);

M is CH$_2$ or CH(CH$_3$);

and all other variables are as originally defined in Class C1.

A second sub-class of the first class (Sub-class C1-S2) includes compounds of Formula II and pharmaceutically acceptable salts thereof, wherein R$^4$, R$^5$ and T$^1$ are each as defined in the third sub-embodiment of Embodiment E46; and all other variables are as originally defined in Class C1.

A second class of compounds of the present invention (Class C2) includes compounds of Formula II and pharmaceutically acceptable salts thereof, wherein:

R$^1$ is as defined in Embodiment E7;

R$^{2A}$ is as defined in Embodiment E19;

R$^3$ is as defined in Embodiment E19;

X is N, and Y is CH, C(CH$_3$), C(Br), C(Cl), C(F), C(CN), or C(CF$_3$); or

Y is N, and X is CH, C(CH$_3$), C(Br), C(Cl), C(F), C(CN), or C(CF$_3$);

L is a single bond that attaches the ring carbon between X and Y directly to M, O, N(H), or CH$_2$;

M is CH$_2$ or CH(OH);

Z is G$^1$, and G$^1$ is as defined in Embodiment E42;

R$^4$ and R$^5$ and are each as defined in Embodiment E47; and

R$^7$ is H or CH$_3$.

A first sub-class of the second class (Sub-class C2-S1) includes compounds of Formula II and pharmaceutically acceptable salts thereof, wherein:

R$^1$ is as defined in the first sub-embodiment of Embodiment E7;

X is N, and Y is CH, C(CH$_3$), C(Br), C(Cl), C(F), or C(CN); or

Y is N, and X is CH, C(CH$_3$), C(Br), C(Cl), C(F), or C(CN);

M is CH$_2$;

and all other variables are as originally defined in Class C2.

A third class of compounds of the present invention (Class C3) includes compounds of Formula II and pharmaceutically acceptable salts thereof, wherein:

R$^1$ is AryA which is 3-chloro-5-cyanophenyl;

R$^{2A}$ is H, CH$_3$, Cl, Br, F, or CN;

R$^3$ is H, OH, CH$_3$, Cl, Br, F, or CN;

X is N, and Y is CH, C(Cl), or C(F); or Y is N, and X is CH, C(Cl), or C(F);

Z is as defined in Embodiment E43; and

R$^4$ is H or NH$_2$.

A first sub-class of the third class (Sub-class C3-S1) includes compounds of Formula II and pharmaceutically acceptable salts thereof, wherein:

R$^3$ is H, OH, CH$_3$, or F;

L is O, N(H), or CH$_2$;

M is CH$_2$;

and all other variables are as originally defined in Class C3.

A fourth class of compounds of the present invention (Class C4) includes compounds of Formula III:

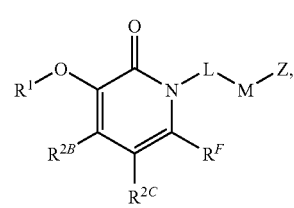

(III)

and pharmaceutically acceptable salts thereof, wherein:

R$^1$ is as defined in Embodiment E6;

R$^{2B}$, R$^{2C}$ and V (which is part of the definition of R$^{2B}$ and R$^{2C}$) are each as defined in Embodiment E18;

R$^F$ is H, C$_{1-4}$ alkyl, Br, Cl, F, or CN;

L is a single bond that attaches the ring nitrogen directly to M, CH$_2$, or CH(CH$_3$);

M is CH$_2$ or CH(CH$_3$);

Z, G$^1$ and G$^2$ are each as defined in Embodiment E41 (wherein the proviso associated with the definitions L, M and Z is modified to read as follows: and provided that when Z is G$^2$, then L is CH$_2$ or CH(CH$_3$), and M is CH$_2$ or CH(CH$_3$));

R$^4$, R$^5$ and T$^1$ (which is part of the definition of R$^4$ and R$^5$) are each as defined in Embodiment E46;

R$^6$ is as defined in Embodiment E52;

R$^7$ is H or C$_{1-4}$ alkyl;

each R$^A$ is independently H or C$_{1-4}$ alkyl; and each R$^B$ is independently H or C$_{1-4}$ alkyl.

A first sub-class of the fourth class (Sub-class C4-S1) includes compounds of Formula II and pharmaceutically acceptable salts thereof, wherein R$^4$ and R$^5$ are as defined in the third sub-embodiment of Embodiment E46; and all other variables are as originally defined in Class C4.

A fifth class of compounds of the present invention (Class C5) includes compounds of Formula III, and pharmaceutically acceptable salts thereof, wherein:

R$^1$ is AryA which is:

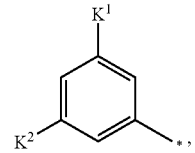

wherein K$^1$ and K$^2$ are each independently Br, Cl, or CN;

R$^{2B}$ is H, CH$_3$, CF$_3$, Cl, Br, F, or CN;

R$^{2C}$ is H, CH$_3$, CF$_3$, Cl, Br, F, or CN;

R$^F$ is H;

L is a bond or CH$_2$;

M is CH$_2$;

Z is

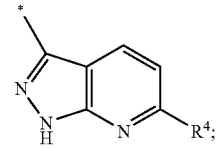

and

R$^4$ is H or NH$_2$.

A first sub-class of the fifth class (Sub-class C5-S1) includes compounds of Formula III and pharmaceutically acceptable salts thereof, wherein:
$R^1$ is AryA which is 3-chloro-5-cyanophenyl;
$R^{2B}$ is H, CH$_3$, Cl, Br, F, or CN;
$R^{2C}$ is H, CH$_3$, Cl, Br, F, or CN;
and all other variables are as originally defined in Class C5.

A second sub-class of the fifth class (Sub-class C5-S2) includes compounds of Formula III and pharmaceutically acceptable salts thereof, wherein:
$R^1$ is AryA which is selected from the group consisting of 3-chloro-5-cyanophenyl, 3-bromo-5-chlorophenyl, 3,5-dicyanophenyl, and 3,5-dichlorophenyl;
$R^{2B}$ is H, CH$_3$, CF$_3$, or Cl;
$R^{2C}$ is H, CH$_3$, or Cl;
L is a bond;
and all other variables are as originally defined in Class C5.

A sixth class of compounds of the present invention (Class C6) includes compounds of Formula IV:

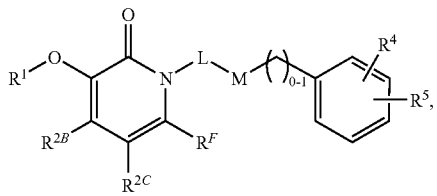

(IV)

and pharmaceutically acceptable salts thereof, wherein:
$R^1$ is as defined in Embodiment E6;
$R^{2B}$, $R^{2C}$ and V (which is part of the definition of $R^{2B}$ and $R^{2C}$) are each as defined in Embodiment E 18;
$R^F$ is H, C$_{1-4}$ alkyl, Br, Cl, F, or CN;
L is CH$_2$ or CH(CH$_3$);
M is C(O)NH or C(O)N(CH$_3$);
$R^4$, $R^5$ and T$^1$ (which is part of the definition of $R^4$ and $R^5$) are each as defined in Embodiment E46;
each $R^A$ is independently H or C$_{1-4}$ alkyl; and
each $R^B$ is independently H or C$_{1-4}$ alkyl.

A first sub-class of the sixth class (Sub-class C6-S1) includes compounds of Formula V:

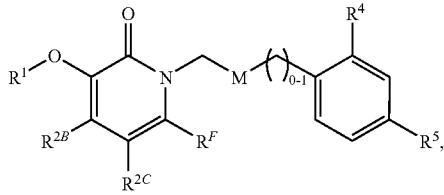

(V)

and pharmaceutically acceptable salts thereof, wherein:
$R^1$ is AryA which is:

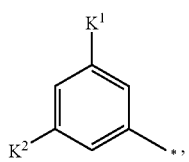

wherein K$^1$ and K$^2$ are each independently Br, Cl, or CN;
$R^{2B}$ is H, CH$_3$, CF$_3$, Cl, Br, F, or CN;
$R^{2C}$ is H, CH$_3$, CF$_3$, Cl, Br, F, or CN;
$R^F$ is H;
M is C(O)NH or C(O)N(CH$_3$);
$R^4$ is H, CH$_3$, Cl, or Br; and
$R^5$ is H, Cl, Br, S(O)$_2$NH$_2$, or C(O)NH$_2$;
and provided that $R^4$ and $R^5$ are not both H.

A second sub-class of the sixth class (Sub-class C6-S2) includes compounds of Formula V, and pharmaceutically acceptable salts thereof, wherein
$R^1$ is AryA which is selected from the group consisting of 3-chloro-5-cyanophenyl, 3-bromo-5-chlorophenyl, 3,5-dicyanophenyl, and 3,5-dichlorophenyl;
$R^{2B}$ is H, CH$_3$, CF$_3$, or Cl;
$R^{2C}$ is H, CH$_3$, or Cl;
and all other variables are as defined in Sub-class C6-S1.

Another embodiment of the present invention is a compound of Formula I, or a pharmaceutically acceptable salt thereof, wherein the compound is selected from the group consisting of the title compounds set forth in Examples 1 to 25.

Another embodiment of the present invention is a compound of Formula I, or a pharmaceutically acceptable salt thereof, as originally defined or as defined in any of the foregoing embodiments, sub-embodiments, aspects, classes, or sub-classes, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest purity level governs. A compound or salt of 100% purity is one which is free of detectable impurities as determined by a standard method of analysis. With respect to a compound of the invention which has one or more asymmetric centers and can occur as mixtures of stereoisomers, a substantially pure compound can be either a substantially pure mixture of the stereoisomers or a substantially pure individual diastereomer or enantiomer.

The present invention also includes prodrugs of the compounds of Formula I. The term "prodrug" refers to a derivative of a compound of Formula I, or a pharmaceutically acceptable salt thereof, which is converted in vivo into Compound I. Prodrugs of compounds of Formula I can exhibit enhanced solubility, absorption, and/or lipophilicity compared to the compounds per se, thereby resulting in increased bioavailability and efficacy. The in vivo conversion of the prodrug can be the result of an enzyme-catalyzed chemical reaction, a metabolic chemical reaction, and/or a spontaneous chemical reaction (e.g., solvolysis). When the compound contains, for example, a hydroxy group, the prodrug can be a derivative of the hydroxy group such as an ester (—OC(O)R), a carbonate ester (—OC(O)OR), a phosphate ester (—O—P (=O)(OH)$_2$), or an ether (—OR). Other examples include the following: When the compound of Formula I contains a carboxylic acid group, the prodrug can be an ester or an amide, and when the compound of Formula I contains a primary amino group or another suitable nitrogen that can be derivatized, the prodrug can be an amide, carbamate, urea, imine, or a Mannich base. One or more functional groups in Compound I can be derivatized to provide a prodrug thereof. Conventional procedures for the selection and preparation of suitable prodrug derivatives are described, for example, in *Design of Prodrugs*, edited by H. Bundgaard, Elsevier, 1985; J. J. Hale et al., *J. Med. Chem.* 2000, vol. 43, pp. 1234-1241; C. S. Larsen and J. Ostergaard, "Design and application of prodrugs" in: *Textbook of Drug Design and Discovery*, 3rd edition, edited by C. S. Larsen, 2002, pp. 410-458; and Beaumont et al., *Current Drug Metabolism* 2003, vol. 4, pp. 461-458; the disclosures of each of which are incorporated herein by reference in their entireties.

Another embodiment of the present invention (alternatively referred to as "Embodiment PD1") is a compound of Formula I-P:

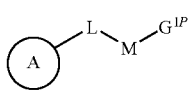
(I-P)

wherein:
$G^{1P}$ is:

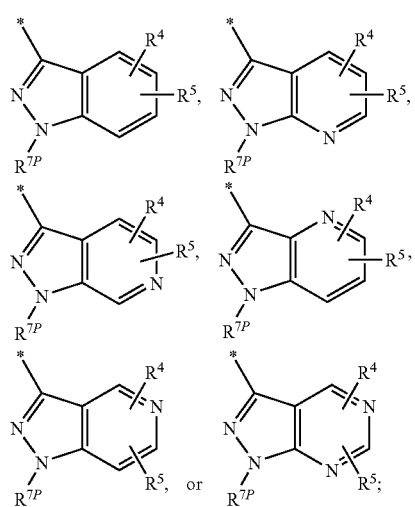

$R^{7P}$ is $PO(OH)O^-.M^+$; $PO(O^-)_2.2M^+$; $PO(O^-)_2.M^{2+}$; or an acid salt of:

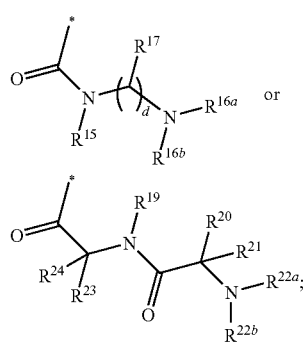

$M^+$ is a pharmaceutically acceptable monovalent counterion;
$M^{2+}$ is a pharmaceutically acceptable divalent counterion;
$R^{15}$ is H or $C_{1-4}$ alkyl;
$R^{16a}$ and $R^{16b}$ are each independently H or $C_{1-4}$ alkyl;
$R^{17}$ is H or $C_{1-4}$ alkyl;
$R^{19}$ is H or $C_{1-4}$ alkyl;
$R^{20}$, $R^{21}$, $R^{22a}$, $R^{22b}$, $R^{23}$ and $R^{24}$ are each independently H or $C_{1-4}$ alkyl; and
d is an integer equal to 2, 3, or 4;
and all other variables are as originally defined above for a compound of Formula I or as defined in Embodiment E1.

Another embodiment of the present invention (Embodiment PD2) is a compound as defined in Embodiment PD 1, wherein the compound is a compound of Formula

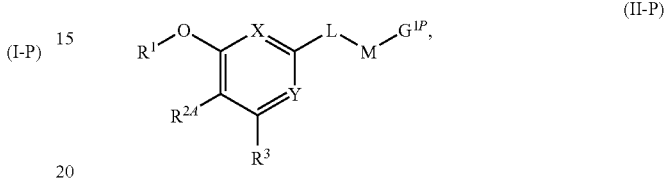
(II-P)

wherein all variables are as defined in Embodiment PD1.

Another embodiment of the present invention (Embodiment PD3) is a compound as defined in Embodiment PD2, wherein the compound is a compound of Formula

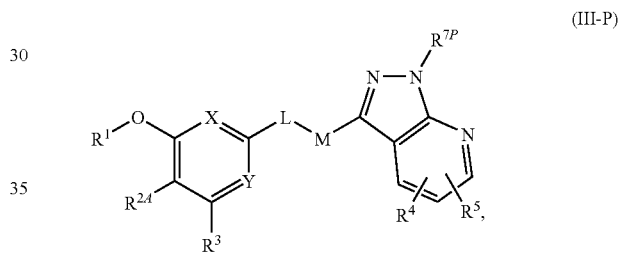
(III-P)

wherein all variables are as defined in Embodiment PD2.

Sub-embodiments of the present invention include a compound of Formula I-P as defined in Embodiment PD 1, wherein the variables are as respectively defined in Embodiments E4 to E39, E45 to E51 and E68 to E76.

Another embodiment of the present invention (Embodiment PD4) is a compound as defined in any one of Embodiments PD1 to PD3, wherein $R^{7P}$ is an acid salt of:

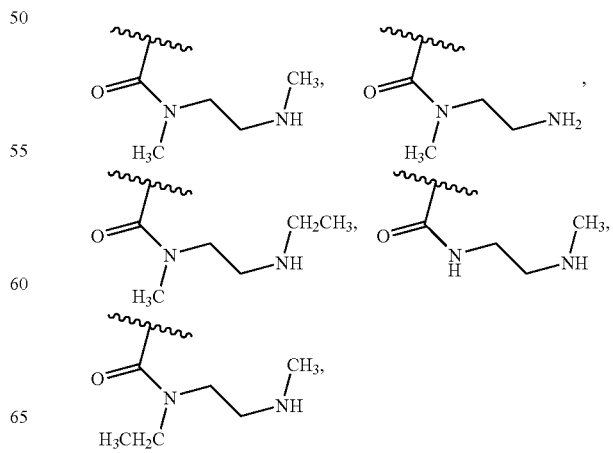

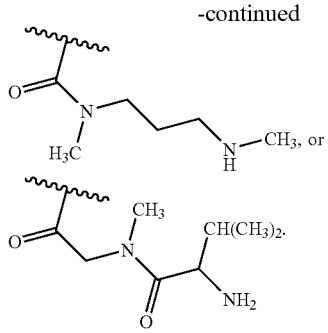

In an aspect of Embodiment PD4, the acid salt in the definition of $R^{7P}$ is a hydrochloride salt.

Pharmaceutically acceptable monovalent counterions ($M^+$) suitable for use in the prodrugs of the invention described in the foregoing embodiments include $NH_4^+$, alkali metal cations (e.g., $Na^+$ or $K^+$), and cations from alkylamines, hydroxyalkylamines (e.g., tris(hydroxymethyl)methylamine), choline, lysine, arginine, histidine, and N-methyl-D-glucamine. Suitable divalent counterions ($M^{2+}$) include the cations of alkaline earth metals such as $Mg^{2+}$ and $Ca^{2+}$. Additional pharmaceutically acceptable salts of basic drugs (pharmaceutically acceptable monovalent and divalent counterions) are described in P. L. Gould, *Int. J. Pharm.* 1986, vol. 33 pp. 201-217 and S. M. Berge et al., *J. Pharm. Sci.,* 1977, vol. 66, pp. 1-19.

Acid salts suitable for use in the prodrugs of the invention described in the foregoing embodiments include the salts of organic and inorganic acids. Suitable salts of inorganic acids include the salts of hydrochloric acid, sulfuric acid, alkali metal bisulfates (e.g., $KHSO_4$), and the like. Suitable salts of organic acids include the salts of carboxylic acids and sulfonic acids, such as alkylcarboxylic acids (e.g., acetic acid, propanoic acid, butyric acid, etc.), arylcarboxylic acids (benzoic acid), alkylsulfonic acids (e.g., ethylsulfonic acid), and arylsulfonic acids (e.g., benzenesulfonic acid or toluenesulfonic acid).

While not wishing to be bound by any particular theory, it is believed that the compounds set forth in Embodiments PD2 to PD4 act as prodrugs, wherein the compound is relatively stable at low pH (e.g., pH=1 to 3) but will convert by hydrolysis or cyclization to its free base at physiological pH (e.g., a pH of greater than about 7), thereby releasing the active substance in vivo. This reaction is exemplified as follows for a hydrochloride salt:

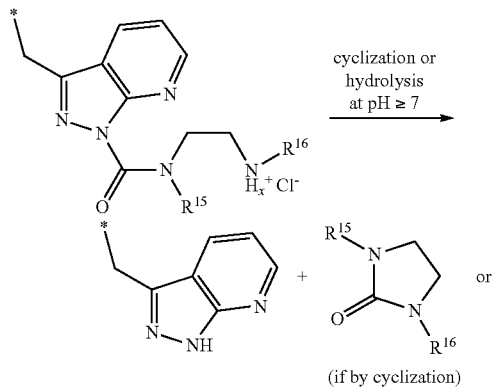

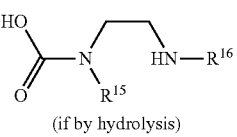

(if by hydrolysis)

Other embodiments of the present invention include the following:

(a) A pharmaceutical composition comprising an effective amount of a compound of Formula I as defined above, or a prodrug or pharmaceutically acceptable salt thereof, and a pharmaceutically acceptable carrier.

(b) A pharmaceutical composition which comprises the product prepared by combining (e.g., mixing) an effective amount of a compound of Formula I as defined above, or a prodrug or pharmaceutically acceptable salt thereof, and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, HIV reverse transcriptase inhibitors, HIV integrase inhibitors, HIV fusion inhibitors, and HIV entry inhibitors.

(e) A combination which is (i) a compound of Formula I as defined above, or a prodrug or pharmaceutically acceptable salt thereof, and (ii) an anti-HIV agent selected from the group consisting of HIV antiviral agents, immunomodulators, and anti-infective agents; wherein Compound I and the anti-HIV agent are each employed in an amount that renders the combination effective for inhibition of HIV reverse transcriptase, for treatment or prophylaxis of infection by HIV, or for treatment, prophylaxis of, or delay in the onset or progression of AIDS.

(f) The combination of (e), wherein the anti-HIV agent is an antiviral selected from the group consisting of HIV protease inhibitors, HIV reverse transcriptase inhibitors (nucleoside or non-nucleoside), HIV integrase inhibitors, HIV fusion inhibitors, and HIV entry inhibitors.

(g) A method for the inhibition of HIV reverse transcriptase in a subject in need thereof which comprises administering to the subject an effective amount of a compound of Formula I or a prodrug or pharmaceutically acceptable salt thereof.

(h) A method for the prophylaxis or treatment of infection by HIV (e.g., HIV-1) in a subject in need thereof which comprises administering to the subject an effective amount of a compound of Formula I or a prodrug or pharmaceutically acceptable salt thereof.

(i) The method of (h), wherein the compound of Formula I is administered in combination with an effective amount of at least one other HIV antiviral selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, and HIV entry inhibitors.

(j) A method for the prophylaxis, treatment or delay in the onset or progression of AIDS in a subject in need thereof which comprises administering to the subject an effective amount of a compound of Formula I or a prodrug or pharmaceutically acceptable salt thereof (k) The method of (j), wherein the compound is administered in combination with an effective amount of at least one other HIV antiviral selected from the group consisting of HIV protease inhibitors, HIV integrase inhibitors, non-nucleoside HIV reverse transcriptase inhibitors, nucleoside HIV reverse transcriptase inhibitors, HIV fusion inhibitors, and HIV entry inhibitors.

(l) A method for the inhibition of HIV reverse transcriptase in a subject in need thereof which comprises administering to the subject the pharmaceutical composition of (a), (b), (c) or (d) or the combination of (e) or (f).

(m) A method for the prophylaxis or treatment of infection by HIV (e.g., HIV-1) in a subject in need thereof which comprises administering to the subject the pharmaceutical composition of (a), (b), (c) or (d) or the combination of (e) or (f).

(n) A method for the prophylaxis, treatment, or delay in the onset or progression of AIDS in a subject in need thereof which comprises administering to the subject the pharmaceutical composition of (a), (b), (c) or (d) or the combination of (e) or (f).

The present invention also includes a compound of Formula I, or a prodrug or pharmaceutically acceptable salt thereof, (i) for use in, (ii) for use as a medicament for, or (iii) for use in the preparation of a medicament for: (a) therapy (e.g., of the human body), (b) medicine, (c) inhibition of HIV reverse transcriptase, (d) treatment or prophylaxis of infection by HIV, or (e) treatment, prophylaxis of, or delay in the onset or progression of AIDS. In these uses, the compounds of the present invention can optionally be employed in combination with one or more anti-HIV agents selected from HIV antiviral agents, anti-infective agents, and immunomodulators.

Additional embodiments of the invention include the pharmaceutical compositions, combinations and methods set forth in (a)-(n) above and the uses (i)(a)-(e) through (iii)(a)-(e) set forth in the preceding paragraph, wherein the compound of the present invention employed therein is a compound of one of the embodiments, sub-embodiments, aspects, classes, or sub-classes described above. In all of these embodiments etc., the compound may optionally be used in the form of a prodrug or pharmaceutically acceptable salt.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or its prodrug or salt and a pharmaceutically acceptable carrier and optionally one or more excipients, it is understood that the term "substantially pure" is in reference to a compound of Formula I or its prodrug or salt per se.

Still additional embodiments of the present invention include the pharmaceutical compositions, combinations and methods set forth in (a)-(n) above and the uses (i)(a)-(e) through (iii)(a)-(e) set forth above, wherein the HIV of interest is HIV-1. Thus, for example, in the pharmaceutical composition (d), the compound of Formula I is employed in an amount effective against HIV-1 and the anti-HIV agent is an HIV-1 antiviral selected from the group consisting of HIV-1 protease inhibitors, HIV-1 reverse transcriptase inhibitors, HIV-1 integrase inhibitors, HIV-1 fusion inhibitors and HIV-1 entry inhibitors.

As used herein, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and iso-propyl, ethyl and methyl. As another example, "$C_{1-4}$ alkyl" refers to n-, iso-, sec- and t-butyl, n- and isopropyl, ethyl and methyl.

The term "alkenyl" refers to a monovalent straight or branched chain aliphatic hydrocarbon radical containing one carbon-carbon double bond and having a number of carbon atoms in the specified range. Thus, for example, "$C_2$-$C_6$ alkenyl" (or "$C_{2-6}$ alkenyl") refers to all of the hexenyl and pentenyl isomers as well as 1-butenyl, 2-butenyl, 3-butenyl, isobutenyl, 1-propenyl, 2-propenyl, and ethenyl (or vinyl). A class of alkenyls of interest with respect to the invention are alkenyls of formula —CH=CH—$(CH_2)_{1-3}CH_3$.

The term "alkynyl" refers to a monovalent straight or branched chain aliphatic hydrocarbon radical containing one carbon-carbon triple bond and having a number of carbon atoms in the specified range. Thus, for example, "$C_2$-$C_6$ alkynyl" (or "$C_{2-6}$ alkynyl") refers to all of the hexynyl and pentynyl isomers as well as 1-butynyl, 2-butynyl, 3-butynyl, 1-propynyl, 2-propynyl, and ethynyl.

The term "alkylene" refers to any divalent linear or branched chain aliphatic hydrocarbon radical having a number of carbon atoms in the specified range. Thus, for example, "—$C_{1-6}$ alkylene-" refers to any of the $C_1$ to $C_6$ linear or branched alkylenes, and "—$C_{1-4}$ alkylene-" refers to any of the $C_1$ to $C_4$ linear or branched alkylenes. A class of alkylenes of interest with respect to the invention is —$(CH_2)_{1-6}$—, and sub-classes of particular interest include —$(CH_2)_{1-4}$—, —$(CH_2)_{2-4}$—, —$(CH_2)_{1-3}$—, —$(CH_2)_{2-3}$—, —$(CH_2)_{1-2}$—, and —$CH_2$—. Another sub-class of interest is an alkylene selected from the group consisting of —$CH_2$—, —CH($CH_3$)—, and —C($CH_3)_2$—.

The term "cycloalkyl" refers to any monocyclic ring of an alkane having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl.

The term "cycloalkenyl" refers to any monocyclic ring of an alkene having a number of carbon atoms in the specified range. Thus, for example, "$C_{5-8}$ cycloalkenyl" (or "$C_5$-$C_8$ cycloalkenyl") refers to cyclopentenyl, cyclohexenyl, cycloheptenyl, and cyclooctenyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "$C_{1-6}$ haloalkyl" (or "C haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.). A fluoroalkyl of particular interest is $CF_3$.

The term "C(O)" refers to carbonyl. The terms "$S(O)_2$" and "$SO_2$" each refer to sulfonyl. The term "S(O)" refers to sulfinyl.

An asterisk ("*") at the end of an open bond in a chemical group denotes the point of attachment of the group to the rest of the compound.

The term "aryl" refers to (i) phenyl, (ii) 9- or 10-membered bicyclic, fused carbocyclic ring systems in which at least one ring is aromatic, and (iii) 11- to 14-membered tricyclic, fused carbocyclic ring systems in which at least one ring is aromatic. Suitable aryls include, for example, phenyl, naphthyl, tetrahydronaphthyl (tetralinyl), indenyl, anthracenyl, and fluorenyl. A class of aryls of interest with respect to the invention is phenyl and napthyl. An aryl of particular interest is phenyl.

The term "heteroaryl" refers to (i) a 5-or 6-membered heteroaromatic ring containing from 1 to 4 heteroatoms independently selected from N, O and S, wherein each N is optionally in the form of an oxide, (ii) a 9-or 10-membered bicyclic fused ring system, or (iii) an 11-to 16-membered tricyclic fused ring system, wherein the fused ring system of (ii) or (iii) contains from 1 to 6 heteroatoms independently selected from N, O and S, wherein each ring in the fused ring system contains zero, one or more than one heteroatom, at least one ring is aromatic, each N is optionally in the form of an oxide, and each S in a ring which is not aromatic is optionally S(O) or S(O)$_2$. Suitable 5-and 6-membered heteroaromatic rings include, for example, pyridyl, pyrrolyl, pyrazinyl, pyrimidinyl, pyridazinyl, triazinyl, thienyl, furanyl, imidazolyl, pyrazolyl, triazolyl (i.e., 1,2,3-triazolyl or 1,2,4-triazolyl), tetrazolyl, oxazolyl, isooxazolyl, oxadiazolyl (i.e., the 1,2,3-, 1,2,4-, 1,2,5-(furazanyl) or 1,3,4-isomer), oxatriazolyl, thiazolyl, isothiazolyl, and thiadiazolyl. Suitable 9-and 10-membered heterobicyclic, fused ring systems include, for example, benzofuranyl, indolyl, indazolyl, naphthyridinyl, isobenzofuranyl, benzopiperidinyl, benzisoxazolyl, benzoxazolyl, chromenyl, quinolinyl, isoquinolinyl, cinnolinyl, quinazolinyl, tetrahydroquinolinyl, tetrahydroisoquinolinyl, isoindolyl, benzodioxolyl (e.g., benzo-1,3-dioxolyl:

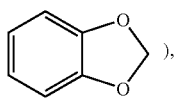), benzopiperidinyl, benzisoxazolyl, benzoxazolyl, chromanyl, isochromanyl, benzothienyl, benzofuranyl, imidazo[1,2-a]pyridinyl, benzotriazolyl, dihydroindolyl, dihydroisoindolyl, indazolyl, indolinyl, isoindolinyl, quinoxalinyl, quinazolinyl, 2,3-dihydrobenzofuranyl, and 2,3-dihydrobenzo-1,4-dioxinyl (i.e.,

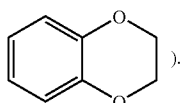).

Suitable tricyclic heteroaryls include, for example, xanthyl and carbazolyl.

Examples of 4-to 7-membered, saturated heterocyclic rings within the scope of this invention (see, e.g., the definition of $R^C$ and $R^D$) include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4-to 7-membered, mono-unsaturated heterocyclic rings within the scope of this invention include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

It is understood that the specific rings and ring systems suitable for use in the present invention are not limited to those listed in the preceding paragraphs. These rings and ring systems are merely representative.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also to be understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. As another example, an aryl or heteroaryl described as optionally substituted with "from 1 to 6 substituents" is intended to include as aspects thereof, an aryl or heteroaryl substituted with 1 to 6 substituents, 2 to 6 substituents, 3 to 6 substituents, 4 to 6 substituents, 5 to 6 substituents, 6 substituents, 1 to 5 substituents, 2 to 5 substituents, 3 to 5 substituents, 4 to 5 substituents, 5 substituents, 1 to 4 substituents, 2 to 4 substituents, 3 to 4 substituents, 4 substituents, 1 to 3 substituents, 2 to 3 substituents, 3 substituents, 1 to 2 substituents, 2 substituents, and 1 substituent.

When any variable (e.g., $R^A$ or $R^B$) occurs more than one time in any constituent or in Formula I or in any other formula depicting and describing compounds of the present invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., cycloalkyl, aryl, or heteroaryl) provided such ring substitution is chemically allowed and results in a stable compound.

As would be recognized by one of ordinary skill in the art, certain of the compounds of the present invention can exist as tautomers. All tautomeric forms of these compounds, whether isolated individually or in mixtures, are within the scope of the present invention. For example, in instances where a hydroxy (—OH) substituent is permitted on a heteroaromatic ring and keto-enol tautomerism is possible, it is understood that the substituent might in fact be present, in whole or in part, in the keto form, as exemplified here:

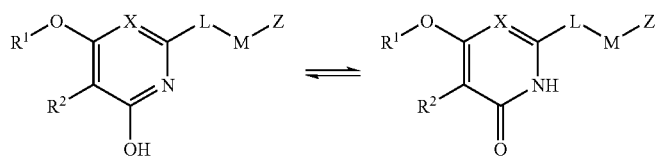

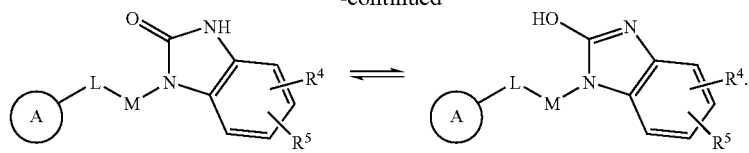

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I.

As a result of the selection of substituents and substituent patterns, certain compounds of the present invention can have asymmetric centers and can occur as mixtures of stereoisomers, or as individual diastereomers, or enantiomers. All isomeric forms of these compounds, whether individually or in mixtures, are within the scope of the present invention.

The methods of the present invention involve the use of compounds of the present invention in the inhibition of HIV reverse transcriptase (e.g., wild type HIV-1 and/or mutant strains thereof), the prophylaxis or treatment of infection by human immunodeficiency virus (HIV) and the prophylaxis, treatment or delay in the onset or progression of consequent pathological conditions such as AIDS. Prophylaxis of AIDS, treating AIDS, delaying the onset or progression of AIDS, or treating or prophylaxis of infection by HIV is defined as including, but not limited to, treatment of a wide range of states of HIV infection: AIDS, ARC (AIDS related complex), both symptomatic and asymptomatic, and actual or potential exposure to HIV. For example, the present invention can be employed to treat infection by HIV after suspected past exposure to HIV by such means as blood transfusion, exchange of body fluids, bites, accidental needle stick, or exposure to patient blood during surgery. As another example, the present invention can also be employed to prevent transmission of HIV from a pregnant female infected with HIV to her unborn child or from an HIV-infected female who is nursing (i.e., breast feeding) a child to the child via administration of an effective amount of Compound I or a prodrug or pharmaceutically acceptable salt thereof.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, or benzoic acid. When compounds employed in the present invention carry an acidic moiety (e.g., —COOH or a phenolic group), suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of Formula I mean providing the compound or a prodrug of the compound to the individual in need of treatment or prophylaxis. When a compound or a prodrug thereof is provided in combination with one or more other active agents (e.g., antiviral agents useful for treating or prophylaxis of HIV infection or AIDS), "administration" and its variants are each understood to include provision of the compound or prodrug and other agents at the same time or at different times. When the agents of a combination are administered at the same time, they can be administered together in a single composition or they can be administered separately.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of active compound sufficient to inhibit HIV reverse transcriptase (wild type and/or mutant strains thereof) and thereby elicit the response being sought (i.e., an "inhibition effective amount"). When the active compound (i.e., active ingredient) is administered as the salt, references to the amount of active ingredient are to the free form (i.e., the non-salt form) of the compound.

In the method of the present invention (i.e., inhibiting HIV reverse transcriptase, treating or prophylaxis of HIV infection or treating, prophylaxis of, or delaying the onset or progression of AIDS), the compounds of Formula I, optionally in the form of a salt or a prodrug, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, infrasternal injection or infusion techniques), by inhalation spray, or rectally, in the form of a unit dosage of a pharmaceutical composition containing an effective amount of the compound and conventional non-toxic pharmaceutically acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in Remington's Pharmaceutical Sciences, 18$^{th}$ edition, edited by A. R. Gennaro, Mack Publishing Co., 1990 and in Remington—The Science and Practice of Pharmacy, 21st edition, Lippincott Williams & Wilkins, 2005.

In one embodiment, the compound of Formula I can be orally administered as a suspension of an amorphous mixture of Compound I and a polymeric stabilizing agent. The amorphous mixture can be obtained by dissolving or suspending Compound I and the polymer in a suitable solvent and then spray drying. The spray dried mixture can then be stably suspended in a suitable carrier for administration. This approach is attractive for compounds of Formula I with relatively low aqueous solubility. For example, an amorphous mixture of the compound of Example 13 and HPMCAS-LF/LG (available as AQCAT from Shin Etsu) in a 1:4 ratio can be obtained by first completely dissolving HPPMCAS-LF/LG in acetone, then adding and dissolving the compound, and then spray drying the solution to obtain a solid amorphous mixture. The spray drying can be conducted using a conventional spray dryer such as a Niro SD Micro spray dryer in which nitrogen and solution are fed via a 2-fluid nozzle into a drying chamber in which additional heated gas is flowing to dry the droplets, after which the dried particles are carried by the processing gas into a cyclone followed by a bag filter for collection. This amorphous mixture can then be stably suspended in methocel at a pH below about 5.5 for administration. Subsequent to administration the compound will be released when pH is above 5.5 such as in the upper intestine in humans.

The compounds of Formula I can be administered orally in a dosage range of 0.001 to 1000 mg/kg of mammal (e.g., human) body weight per day in a single dose or in divided doses. One preferred dosage range is 0.01 to 500 mg/kg body weight per day orally in a single dose or in divided doses. Another preferred dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of a compound of Formula I with one or more anti-HIV agents. An "anti-HIV agent" is any agent which is directly or indirectly effective in the inhibition of HIV reverse transcriptase or another enzyme required for HIV replication or infection, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS. Suitable HIV antivirals for use in combination with the compounds of the present invention include, for example, those listed in Table A as follows:

TABLE A

| Name | Type |
|---|---|
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| efavirenz, EFV, Sustiva ®, Stocrin ® | nnRTI |
| efavirenz + emtricitabine + tenofovir DF, Atripla ® | nnRTI + nRTI |
| emtricitabine, FTC, Emtriva ® | nRTI |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| tipranavir, Aptivus ® | PI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor. Some of the drugs listed in the table are used in a salt form; e.g., abacavir sulfate, indinavir sulfate, atazanavir sulfate, nelfinavir mesylate.

It is understood that the scope of combinations of the compounds of this invention with anti-HIV agents is not limited to the HIV antivirals listed in Table A, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the Physicians' Desk Reference, Thomson PDR, Thomson PDR, 57$^{th}$ edition (2003), the 58$^{th}$ edition (2004), the 59$^{th}$ edition (2005), and so forth. The dosage ranges for a compound of the invention in these combinations are the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV reverse transcriptase, e.g., by competitive inhibition. Thus the compounds of this invention are commercial products to be sold for these purposes.

Abbreviations employed herein include the following: ACN=acetonitrile; Bn=benzyl; BOC (or Boc)=t-butyloxycarbonyl; BrdUTP=bromodeoxyuridine triphosphate; t-BuLi=tert-butyl lithium; CHAPS=3[(3-cholamidopropyl) dimethylammonio]-propanesulfonic acid; DCE=1,2-dichloroethane; DCM=dichloromethane; DDQ=2,3-dichloro-5,6-dicyano-1,4-benzoquinone; DHP=dihydropyran; DIBAL=diisobutylaluminum hydride; DMAP=4-dimethylaminopyridine; DME=1,2-dimethoxyethane; DMF=dimethylformamide; DMSO=dimethyl sulfoxide; DPPA=diphenylphosphoryl azide; dNTP=deoxynucleoside triphosphate; EGTA=ethylene glycol bis(2-aminoethyl ether)-N,N,N',N'-tetraacetic acid; Et=ethyl; EtOAc=ethyl acetate; EtOH=ethanol; FBS=fetal bovine serum; HIV=human immunodeficiency virus; HPMCAS=hydroxypropyl methylcellulose acetate succinate); HPLC=high performance liquid chromatography; HRMS=high resolution mass spectroscopy; LC-MS=liquid chromatography-mass spectroscopy; LRMS=low resolution mass spectroscopy; Me=methyl; MeOH=methanol; NBS=N-bromosuccinimide; NCS=N-chlorosuccinimide; NMP=N-methyl pyrrolidinone; NMR=nuclear magnetic resonance; $Pd_2dba_3$=tris(dibenzylideneacetone) dipalladium; Ph=phenyl; t-BuOH=tert-butanol; TEA=triethylamine; TFA=trifluoroacetic acid; THF=tetrahydrofuran; TMANO=trimethylamine N-oxide.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Scheme I depicts a method for preparing compounds of Formula I in which ring A is a substituted pyridyl ring, wherein difluoropyridine I-1 can be treated with an appropriate aryl or heteroaryl alcohol and base (e.g., sodium carbonate or potassium carbonate) to provide I-2. The fluorine of I-2 can be displaced with the sodium salt of an oxygen anion or the appropriate amine to afford the desired products I-3 and I-4 respectively.

Scheme I

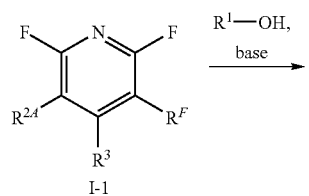

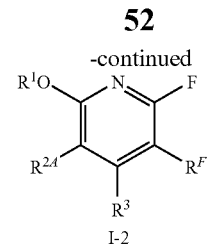

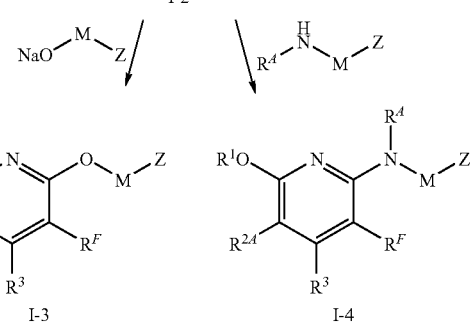

Scheme II details a method for preparing compounds of Formula I in which ring A is a substituted pyridine and L-M=$CH_2CH_2$, wherein methylpyridine II-3 (which can be prepared from II-1 or alternatively from II-2) is halogenated (e.g., brominated) using standard radical halogenation conditions to give the alpha-halo intermediate II-4. Halomethylpyridine II-4 can then be treated with triphenylphosphine to provide phosphinyl halide II-5. which can then be reacted with an aldehyde of formula $G^1$-CHO under standard Wittig conditions to provide vinylpyridine II-6. The vinyl moiety can be reduced (e.g., via hydrogenation) to afford the desired II-7.

Scheme II

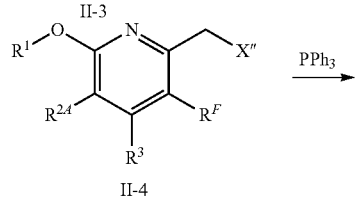

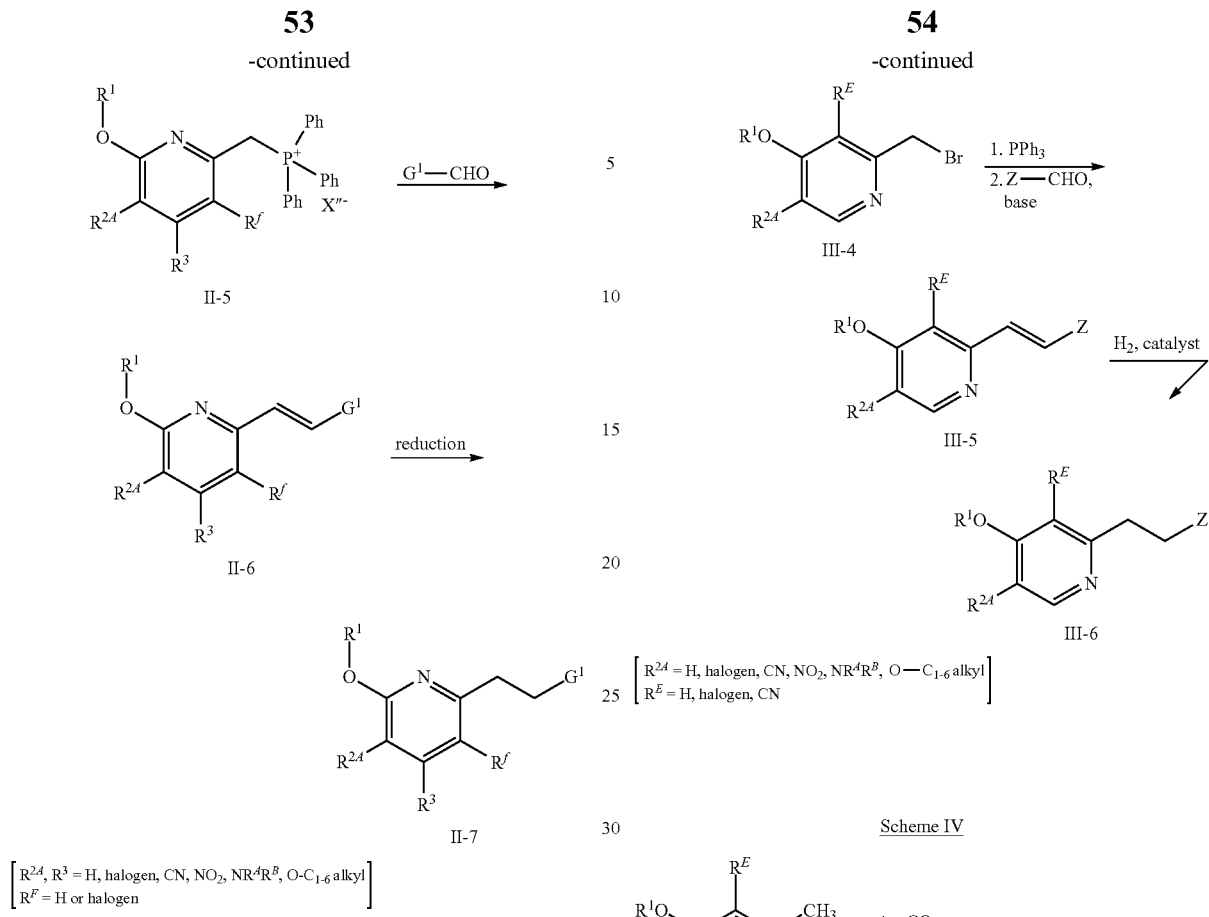
Schemes III, IV, and V as follows depict synthetic approaches similar to that set forth in Scheme II for preparing isomeric pyridine and pyridinone derivatives:

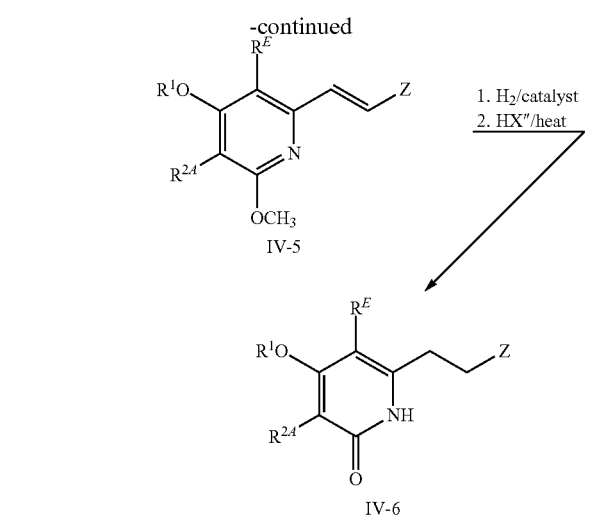

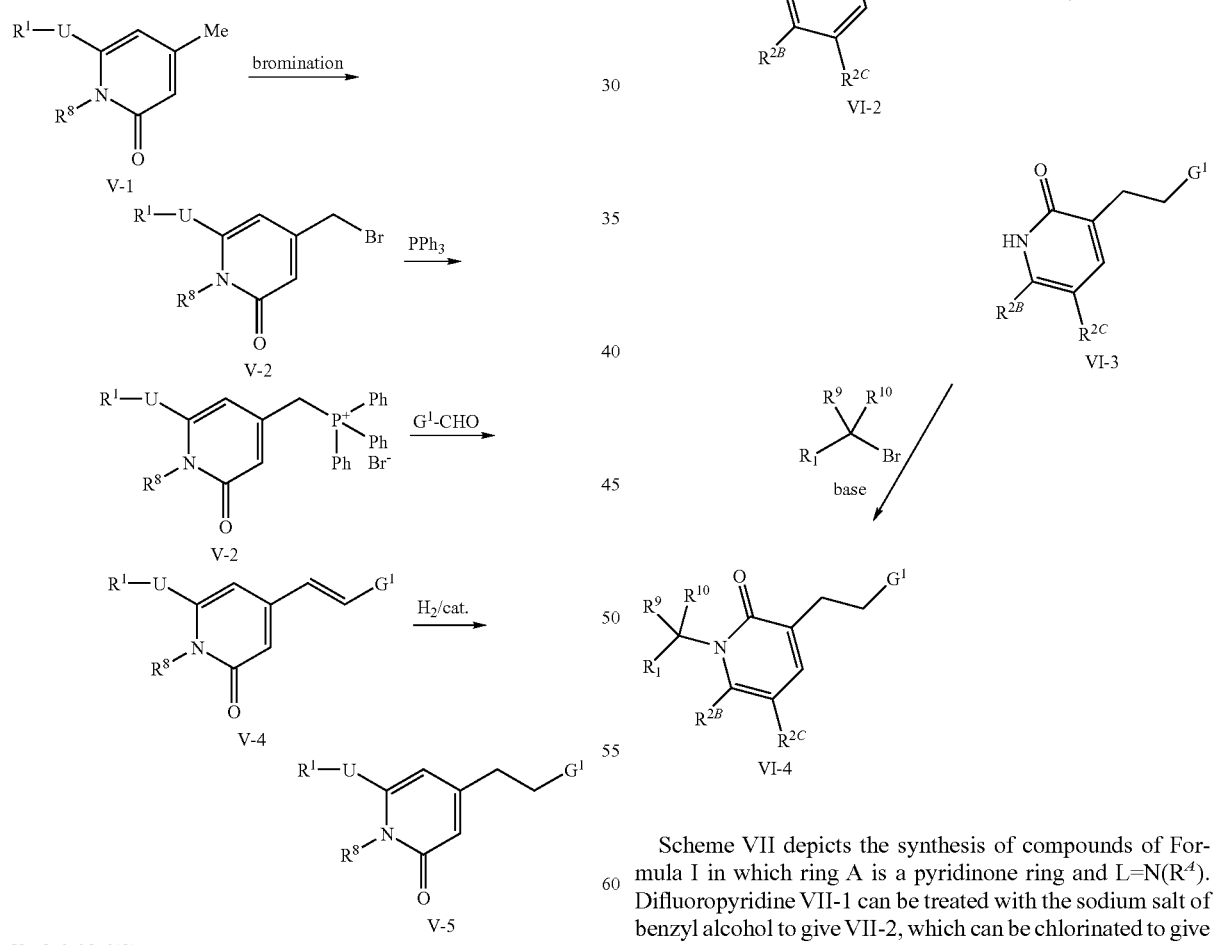

ods, wherein the Wittig reaction is employed in an alternative approach. Substituted aldehyde V-1 and the phosphonium salt G1-PPh₃ X can be reacted under standard conditions to give alkene VI-2. The double bond can be reduced with concurrent removal of the benzyl protecting group (e.g., by catalytic hydrogenation) to provide pyridinone VI-3, which can be alkylated to afford desired product VI-4.

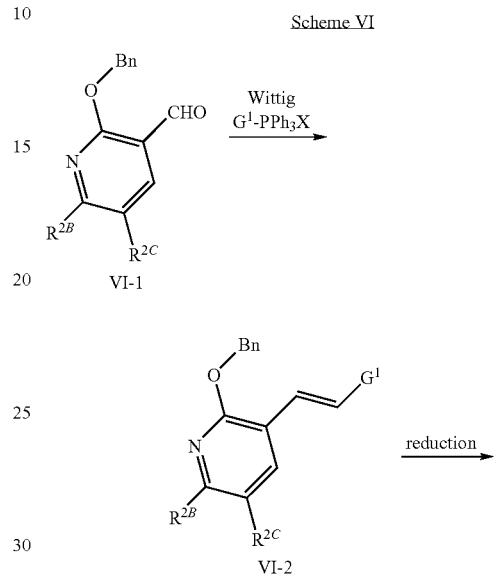

Scheme VII depicts the synthesis of compounds of Formula I in which ring A is a pyridinone ring and L=N(R$^A$). Difluoropyridine VII-1 can be treated with the sodium salt of benzyl alcohol to give VII-2, which can be chlorinated to give chlorofluoropyridine VII-3. The fluorine can be displaced by heating with the appropriate amine to give aminopyridine VII-4. The benzyl protecting group can then be reductively removed (e.g., by Pd-catalyzed hydrogenation) to afford desired product VII-5.

Scheme VI shows the synthesis of an additional pyridinone isomer of Formula I via a modification of the previous meth- Scheme VIII highlights a method that can be used to prepare compounds of Formula I in which ring A is a pyridinone ring and L-M-Z=CH$_2$-G$^1$. Pyridinone VIII-1 can be converted to the methoxypyridine VIII-2 by silver catalyzed alkylation. The methoxypyridine VIII-2 can then be halogenated using standard radical conditions (N-halo succinimide, catalytic benzoyl peroxide, carbon tetrachloride or a similarly inert solvent) to give the alpha halo intermediate VIII-3. Dehalooxidation using TMANO or a similar reagent can provide the aldehyde VIII-4. The aldehyde group on VIII-4 can be reductively aminated by treatment with G$^1$-Li (prepared from butyl lithium and G$^1$-X via halogen metal exchange) to afford alcohol VIII-5. The pyridine can then be dehydroxylated and reconverted to the pyridinone (via demethylation of the methoxy pyridine intermediate VIII-6) to provide the desired VIII-7.

Scheme IX depicts a method analogous to Scheme VIII for the preparation of compounds of Formula I in which ring A is a pyridinone ring and L-M-Z=CH$_2$-G$^2$. The alpha halo intermediate IX-1 (prepared in an analogous manner to compound VIII-3 in Scheme VIII) is treated with G$^2$-H in the presence of a strong base such as NaH to give IX-2. IX-2 is demethylated using a strong acid (HX″) with heating to provide the desired product IX-3.

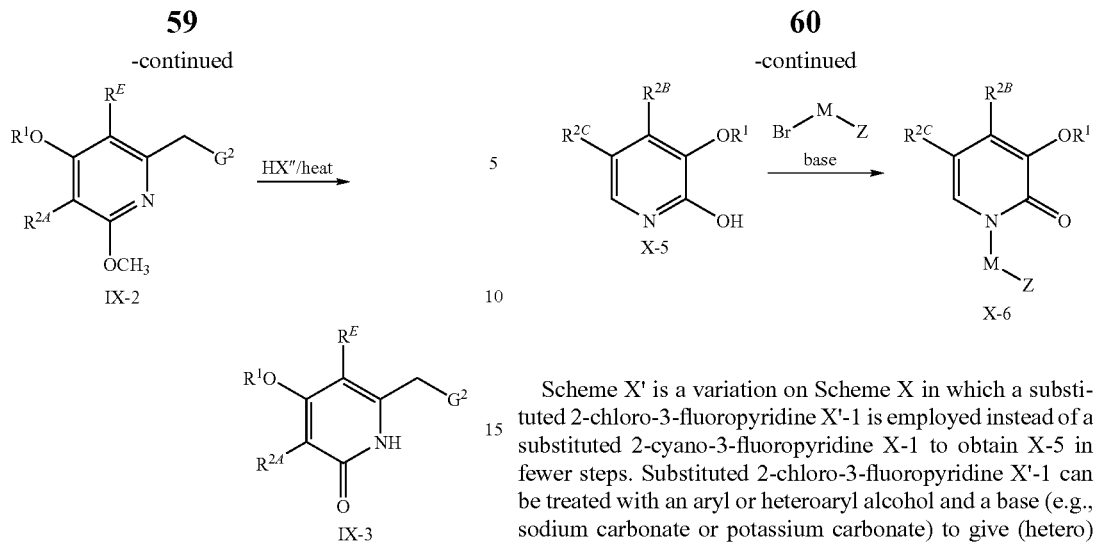

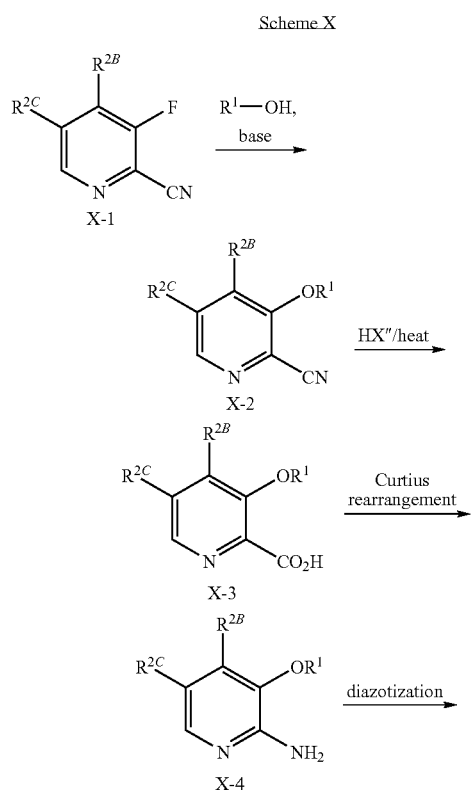

Scheme X shows a synthesis of compounds of Formula I in which ring A is an isomeric pyridinone ring, and L-M-Z=CH$_2$—Z or CH$_2$CH$_2$—Z, wherein substituted 2-cyano-3-fluoropyridine X-1 can be treated with an aryl or heteroaryl alcohol and a base (e.g., sodium carbonate or potassium carbonate) to give (hetero)aryloxypyridine X-2. The nitrile can then be hydrolyzed using a strong aqueous acid (e.g., hydrochloric acid or sulfuric acid) and heat to afford the carboxypyridine X-3. Curtius rearrangement can then be employed to provide amine X-4, which can then be diazotized to give the pyridinone X-5, which can then be alkylated with the appropriate bromide in the presence of a base to afford desired product X-6.

Scheme X' is a variation on Scheme X in which a substituted 2-chloro-3-fluoropyridine X'-1 is employed instead of a substituted 2-cyano-3-fluoropyridine X-1 to obtain X-5 in fewer steps. Substituted 2-chloro-3-fluoropyridine X'-1 can be treated with an aryl or heteroaryl alcohol and a base (e.g., sodium carbonate or potassium carbonate) to give (hetero)aryloxypyridine X'-2. Chloropyridine X'-2 can then be hydrolyzed using a strong aqueous base (e.g., KOH) to give the pyridinone X-5, which can then be alkylated with the appropriate bromide in the presence of a base to afford desired product X-6.

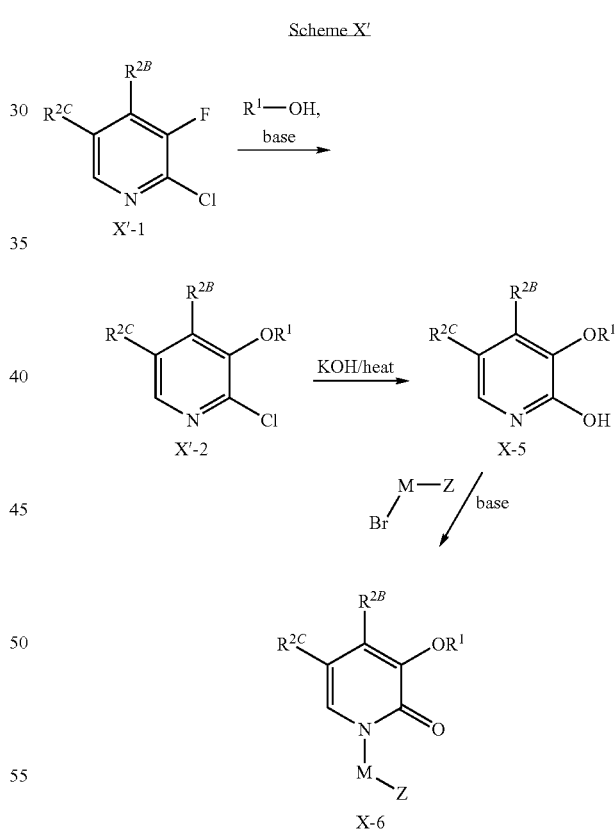

Scheme XI shows a method for the synthesis of isomeric pyridinone derivatives of Formula I in which R$^8$=H, alkyl, halogenated alkyl, or cycloalkyl, wherein pyrone IX-1 can be heated with amine R$^8$—NH$_2$ to give the N-substituted pyridinone derivative IX-2. The pyridinone can then be alkylated with strong base (e.g., an alkali metal hydride such as sodium hydride or lithium hydride) and the appropriate bromide to afford desired product IX-3.

Scheme XI

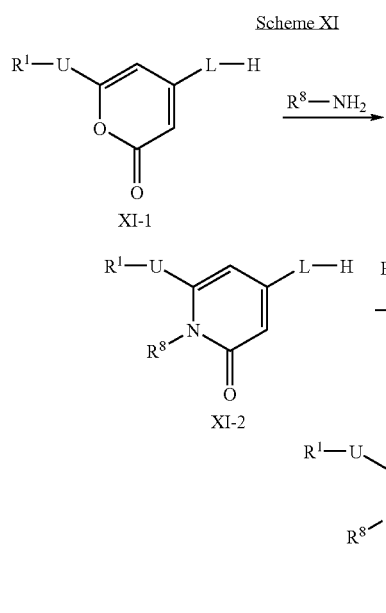

Scheme XII shows a method for the synthesis of an isomeric pyridinone of Formula I in which $R^{2B}$=H, alkyl, haloalkyl, or cycloalkyl and L=NH, wherein nitropyridinone intermediate XII-1 can be reduced by catalytic hydrogenation to give the aminopyridinone XII-2. The aminopyridinone can then be alkylated with the appropriate bromide in the presence of a strong base such as NaH or KH to afford desired product XII-3.

Scheme XII

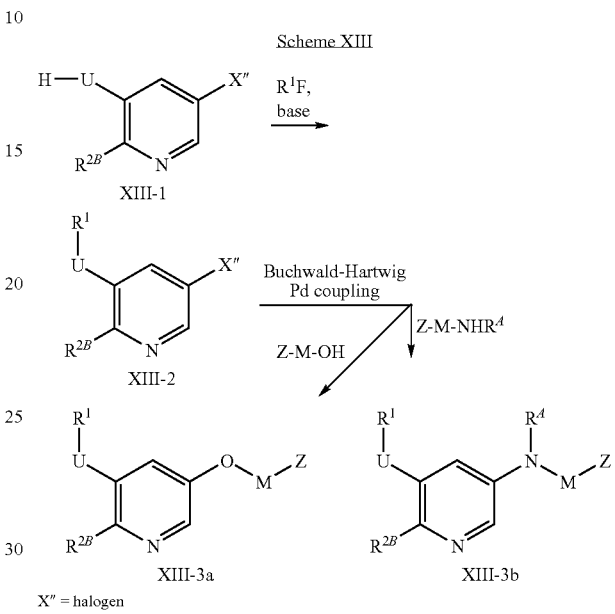

$R^{2B}$ = H, alkyl, haloalkyl, cycloalkyl

Scheme XIII shows a method for preparing compounds of Formula I in which ring A is a 2,3,5 tri-substituted pyridine substituted as follows: $R^{2B}$=H, alkyl, haloalkyl, cycloalkyl, $NO_2$, CN, $N(R^A)R^B$, or $C(O)N(R^A)R^B$; U=O or S; X''=Cl, Br, or I; and L=O or $NR^A$. In this method, substituted pyridine XIII-1 can be treated with a heteroaryl or aryl fluoride in the presence of a base to provide (hetero)arylated intermediate XIII-2, which can then be subjected to Buchwald-Hartwig Palladium coupling conditions (as described in the following references: *Org. Lett* 2005., 7(18): 3965-3968; *J. Amer. Chem. Soc.* 1997, 119: 3395-3396; *J Amer. Chem. Soc.* 1997, 119: 6787-6795) using an appropriate catalyst such as $Pd_2dba_3$, base (e.g., sodium tert-butoxide or potassium phosphate) and an appropriate amine or alcohol to obtain desired product XIII-3a or XIII-3b.

Scheme XIII

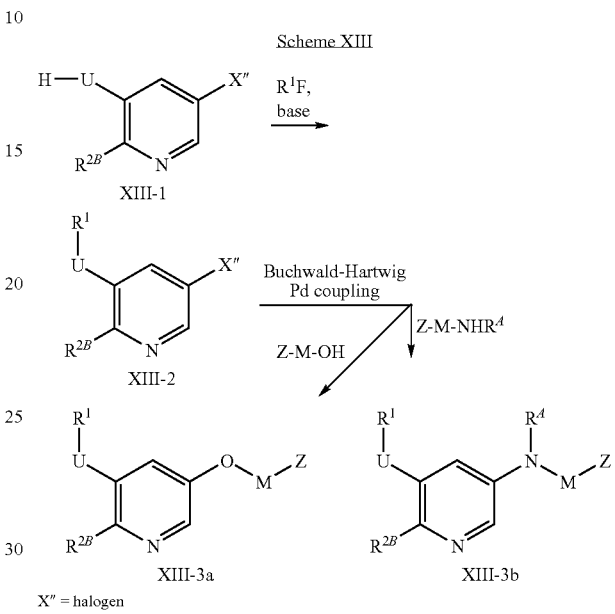

X'' = halogen

The following examples serve only to illustrate the invention and its practice. The examples are not to be construed as limitations on the scope or spirit of the invention. The term "room temperature" in the examples refers to the ambient temperature which was typically in the range of about 19° C. to 26° C.

PREPARATIVE EXAMPLE 1 tert-butyl
3-formyl-1H-pyrazolo[3,4-b]pyridine-1-carboxylate
(Intermediate I-A)

I-A

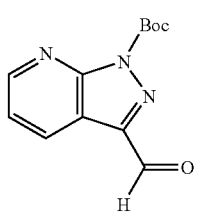

Solid trimethylamine N-oxide (241 mg; 3.20 mmol) was added to a solution of tert-butyl 3-(bromomethyl)-1H-pyrazolo[3,4-b]pyridine-1-carboxylate (1-1; 400 mg; 1.281 mmol) in dichloromethane, and the resulting reaction mixture was stirred at room temperature for 3 hours. The reaction mixture was diluted with dichloromethane, washed with brine (2×), dried over $MgSO_4$, and evaporated to give the title compound I-A as a white solid. MS M+1=148.1. ¹H NMR (CDCl₃): 1.75 (s, 9H), 7.42 (m, 1H), 8.64 (d, 1H), 8.80 (d, 1H), 10.28 (s, 1H).

PREPARATIVE EXAMPLE 2

6-fluoro-1-(4-methoxybenzyl)-1H-pyrazolo[3,4-b]pyridine-3-carbaldehyde (Intermediate I-E)

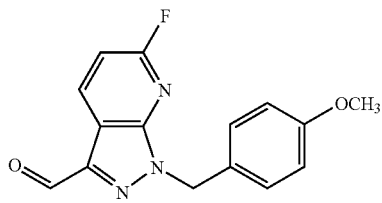

I-E

Step 1: tert-Butyl 6-fluoro-1-(4-methoxybenzyl)-1H-pyrazolo[3,4-b]pyridine-3-carboxylate (I-B)

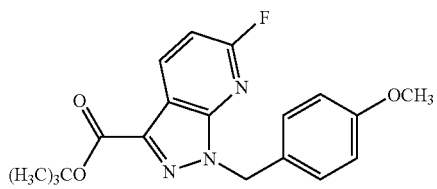

I-B

To a solution of tert-butyl 6-fluoro-1H-pyrazolo[3,4-b]pyridine-3-carboxylate (29.55 g, 125 mmol) in THF (300 mL) cooled in an ice bath was added KOtBu (13.98 g, 125 mmol) at such a rate as to maintain the temperature between 5-10° C., and then 4-methoxybenzyl bromide (18.2 mL, 125 mmol) was added. The resulting mixture was stirred in an ice bath for 1 hour and then stirred at room temperature for 18 hours. The resulting suspension was quenched with saturated aqueous NH₄Cl (200 mL) and then extracted with EtOAc (2×300 mL). The combined organic extracts were washed with brine, dried with MgSO₄ and the solvent removed in vacuo. The resulting residue was purified on a silica gel (1000 g) column (0-11% EtOAc/hexanes) to give the title compound I-B. LRMS (M+1)=380.1

Step 2: [6-fluoro-1-(4-methoxybenzyl)-1H-pyrazolo[3,4-b]pyridin-3-yl]methanol (I-C)

DIBAL (6.99 mL; 7.0 mmol) was added at −78° C. to a solution of I-B (1.0 g; 2.80 mmol) in toluene at −78° C. The reaction mixture was stirred at −78° C. for 1.5 hours and then warmed to 0° C., at which point the reaction mixture was quenched with NH₄Cl and filtered through celite. The aqueous layer was extracted with methylene chloride, and the extract dried and concentrated to give the title compound I-C as an oil. The product was used without further purification. MS M+1=288.0. ¹H NMR (CDCl₃): 1.90 (m, 1H), 3.72 (s, 3H), 4.95 (d, 2H), 5.45 (s, 2H), 6.72 (d, 1H), 6.80 (d, 2H), 7.28 (d, 2H), 8.15 (t, 1H).

Step 3: 6-fluoro-1-(4-methoxybenzyl)-1H-pyrazolo[3,4-b]pyridine-3-carbaldehyde (1-E)

DMSO (0.247 mL, 3.48 mmol) was added to a solution of oxalyl chloride (183 uL, 2.08 mmol) in dichloromethane at −78° C. The mixture was stirred for 20 minutes and then a solution of I-C (500 mg; 1.74 mmol) in dichloromethane was added dropwise and the contents stirred for 40 minutes. After 40 minutes TEA (1.2 mL, 8.70 mmol) was added and the reaction mixture was warmed with stirring to room temperature and then stirred for an additional 1 hour. The reaction mixture was diluted with water and extracted with dichloromethane. The combined organic extracts were dried over MgSO₄ and concentrated to yield a solid, which was purified via column chromatography to give the title compound I-E. MS M+1: 285.9. ¹H NMR (CDCl₃): 3.80 (s, 3H), 5.62 (s, 2H), 6.85 (d, 2H), 6.95 (d, 1H), 7.20 (d, 2H), 8.60 (t, 1H), 10.15 (s, 1H).

PREPARATIVE EXAMPLE 3

3-chloro-5-{[2-oxo-4-(trifluoromethyl)-1,2-dihydropyridin-3-yl]oxy}benzonitrile 3C

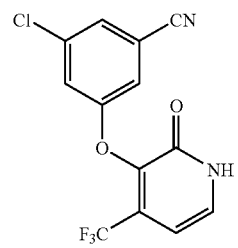

3C

Step 1: 3-(3-bromo-5-chlorophenoxy)-2-chloro-4-(trifluoromethyl)pyridine 3A

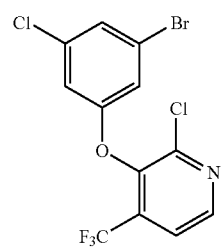

3A

To a round bottom flask charged with 3-bromo-5-chlorophenol (5.20 g, 25.1 mmol) and potassium carbonate (3.46 g, 25.1 mmol) was added N-methylpyrrolidinone (25 mL). To this suspension under N₂ was added 2-chloro-3-fluoro-4-(trifluoromethyl)pyridine (5.00 g, 25.1 mmol) and the reaction mixture was placed in an oil bath at 120° C. After 60 minutes, the reaction mixture was allowed to cool to room temperature at which point, water (100 mL) was added. The mixture was extracted with ethyl acetate (2×100 mL) and the combined organic fractions were washed with brine (3×100 mL), dried (MgSO₄), filtered and the solvent was evaporated under reduced pressure. The resulting residue was adsorbed onto silica gel and purified by column chromatography on a pre-packed silica gel Redi Sep 330 gram column, eluting with 0-75% CH$_2$Cl$_2$ in hexanes to yield the title compound. $^1$H NMR (CDCl$_3$) δ 8.53 (d, J=5.0 Hz, 1H), 7.62 (d, J=5.0 Hz, 1H), 7.29-7.27 (m, 1H), 6.87-6.84 (m, 1H), 6.76-6.73 (m, 1H). FIRMS (M+1)=385.8957.

Step 2: 3-(3-bromo-5-chlorophenoxy)-4-(trifluoromethyl)pyridin-2(1H)-one 3B

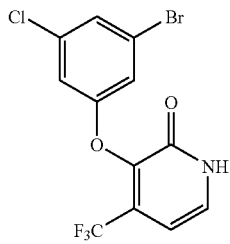

To a round bottom flask charged with 3-(3-bromo-5-chlorophenoxy)-2-chloro-4-(trifluoromethyl)pyridine (9.1 g, 25.3 mmol) and potassium hydroxide (3.96 g, 70.5 mmol) was added tert-butanol (100 mL). This suspension was placed in an oil bath at 75° C. After 48 hours, the reaction mixture was allowed to cool to room temperature and was quenched with saturated aqueous ammonium chloride (50 mL) and diluted with water (50 mL). The mixture was extracted with ethyl acetate (2×100 mL) and the combined organic fractions were washed with water (3×100 mL). The solvent was evaporated under reduced pressure to yield a solid. This was adsorbed onto silica and purified by column chromatography on a pre-packed silica gel Redi Sep 330 gram column, eluting with 0-5% methanol in CH$_2$Cl$_2$ to give the title compound. 1H NMR (DMSO-d$_6$) δ 12.68 (s, 1H), 7.58 (d, J=6.8 Hz, 1H), 7.44-7.40 (m, 1H), 7.20-7.18 (m, 1H), 7.13-7.10 (m, 1H), 6.47 (d, J=6.8 Hz, 1H). FIRMS (M+1)=367.9295.

Step 3: 3-chloro-5-{[2-oxo-4-(trifluoromethyl)-1,2-dihydropyridin-3-yl]oxy}benzonitrile To a round bottom flask charged with 3-(3-bromo-5-chlorophenoxy)-4-(trifluoromethyl)pyridin-2(1H)-one (3.00 g, 8.14 mmol) and copper (I) cyanide (7.29 g, 81.0 mmol) was added N-methylpyrrolidinone (25 mL). This suspension under N$_2$ was placed in an oil bath at 175° C. After 5 hours the reaction mixture was allowed to cool to room temperature. Glacial acetic acid (30 mL) was added to the mixture and stirred for 10 minutes. The mixture was diluted with ethyl acetate (100 mL), filtered through diatomaceous earth and the pad was washed with ethyl acetate (100 mL). The filtrate was washed with water (3×100 mL) and brine (2×100 mL). The organic fraction was dried (Na$_2$SO$_4$), filtered and the solvent was removed under reduced pressure to yield a solid. This was adsorbed onto silica gel and purified by column chromatography on a pre-packed silica gel Redi Sep 120 gram column, eluting with 0-5% methanol in CH$_2$Cl$_2$ to yield the title compound. $^1$H NMR (DMSO-d$_6$) δ 12.70 (s, 1H), 7.76-7.72 (m, 1H), 7.62-7.56 (m, 2H), 7.54-7.52 (m, 1H), 6.48 (d, J=6.8 Hz, 1H). LRMS (M+1)=314.87.

EXAMPLE 1

3-chloro-5-({5-chloro-3-fluoro-6-[(1H-pyrazolo[3,4-b]pyridin-3-ylmethyl)amino]pyridin-2-yl}oxy)benzonitrile (1-7)

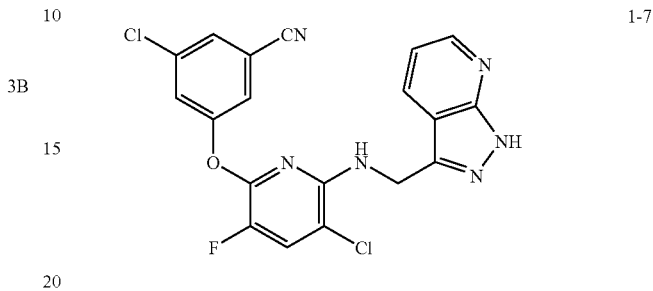

Step 1: 3-(azidomethyl)-1H-pyrazolo[3,4-b]pyridine (1-2)

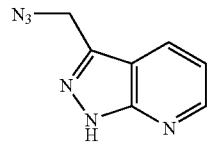 [SMILES: [N-]=[N+]=NCc1n[nH]c2ncccc12]

A solution of 250 mg (0.80 mmol) of tert-butyl 3-(bromomethyl)-1H-pyrazolo[3,4-b]pyridine-1-carboxylate (1-1) and sodium azide (55 mg; 0.85 mmol) in 1 mL anhydrous DMF was heated at 90° C. for 5 hours. The reaction was cooled, diluted with water, and extracted twice with 25 mL portions of EtOAc. The combined EtOAc extracts were washed with brine, dried (anhydrous MgSO$_4$) and concentrated to give a dark oil. The oil was purified by reverse phase preparative HPLC on a Gilson apparatus to give the title compound as a tan solid. MS M+1=152.

Step 2: 3-(aminomethyl)-1H-pyrazolo[3,4-b]pyridine (1-3)

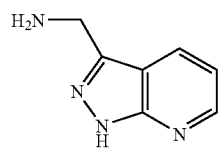

A mixture of 286 mg (1.64 mmol) of 1-2 and 35 mg of 10% palladium on carbon catalyst in 2 mL of absolute EtOH was hydrogentated at 1 atmosphere pressure using a hydrogen filled balloon. After approximately 2 hours, the reaction was determined to be complete by LC-MS analysis. The reaction was filtered through a Celite pad, and the filtrate concentrated in vacuo to give the title product as a pale yellow oil. MS M+1=149.

Step 3: 3-chloro-5-[(5-chloro-3,6-difluoropyridin-2-yl)oxy]benzonitrile (1-6)

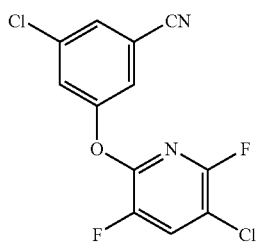

1-6

A solution of 3-chloro-5-cyanophenol (1-4; 218 mg; 1.41 mmol) and 3-chloro-2,5,6-trifluoropyridine (1-5; 250 mg; 1.49 mmol) in anhydrous DMF (2 mL) was cooled to −40° C. under a nitrogen atmosphere. The reaction mixture was then treated with 260 mg (1.94 mmol) of anhydrous potassium carbonate added in one portion, and the reaction mixture was vigorously stirred and allowed to warm to room temperature slowly over 90 minutes. The reaction mixture was then stirred for another hour at room temperature. The reaction mixture was diluted with a large excess of water, and a thick precipitate formed. After trituration, the suspension was filtered and the solid dried to give the title compound as an off white amorphous solid. $^1$H NMR (CDCl$_3$): 7.91 (m, 2H), 7.99 (t, 1H), 8.60 (q, 1H). MS M+1=302.

Step 4: 3-chloro-5-({5-chloro-3-fluoro-6-[(1H-pyrazolo[3,4-b]pyridin-3-ylmethyl)amino]pyridin-2-yl}oxy)benzonitrile (1-7)

A solution of 50 mg (0.166 mmol) of 1-6 and 25 mg (0.166 mmol) of 1-3 in 1.5 mL of dry NMP was heated with stirring at 90° C. under nitrogen. After 7 hours, the reaction was stopped and cooled. The reaction mixture was diluted with water, and extracted twice with EtOAc. The combined EtOAc extracts were washed with water and brine, dried, filtered, and concentrated in vacuo to give a crude oil. The crude product was purified by reversed phase preparative HPLC on a Gilson apparatus to give the title product as a white amorphous solid. MS M+1=430. $^1$H NMR (CDCl$_3$): 4.77 (d, 2H), 5.60 (br m, 1H), 7.17 (q, 1H), 7.34 (m, 1H), 7.36 (m, 1H), 7.39 (m, 1H), 7.50 (d, 1H), 8.01 (dd, 1H), 8.53 (m, 1H), 10.5-11.5 (br, 1H).

EXAMPLE 2

3-[(6-{[(6-amino-1H-pyrazolo[3,4-b]pyridin-3-yl)methyl]amino}-5-chloro-3-fluoropyridin-2-yl)oxy]-5-chlorobenzonitrile (2-7)

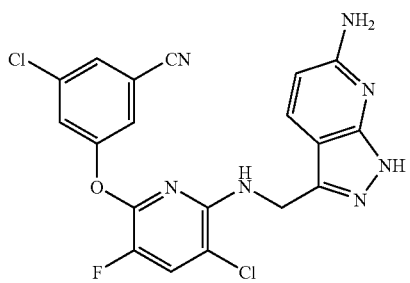

2-7

Step 1: 3-(bromomethyl)-6-fluoro-1H-pyrazolo[3,4-b]pyridine (2-2)

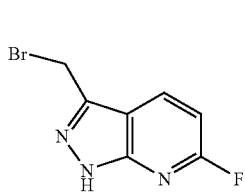

2-2

A solution of 1-Boc-3-(bromomethyl)-6-fluoro-1H-pyrazolo[3,4-b]pyridine (2-1; 195 mg; 0.59 mmol) was stirred in TFA (1 mL) for approximately 30 minutes. The reaction was concentrated in vacuo to give 136 mg (99%) of the desired product as a yellow solid after pumping. The crude product was used as is in the next step.

Step 2: 3-(bromomethyl)-6-fluoro-1-(tetrahydro-2H-pyran-2-yl)-1H-pyrazolo[3,4-b]pyridine (2-3)

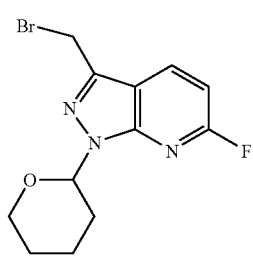

2-3

A solution of 2-2 (167 mg; 0.73 mmol) in 2 mL anhydrous acetonitrile was treated with DDQ (171 mg; 0.07 mmol), followed by 61 mg (0.73 mmol) of 3,4-dihydro-2H-pyran, and the solution heated at 80° C. under nitrogen. LC-MS indicated that the reaction was complete after 1 hour. The reaction mixture was concentrated in vacuo to a brown oil, which was then purified by flash chromatography over silica gel, eluting with 3:1 hexanes:EtOAc. Fractions containing desired product were combined and concentrated in vacuo to give the desired product 2-3 as a clear oil. $^1$H NMR (CDCl$_3$): 1.63 (m, 1H), 1.77 (m, 2H), 1.95 (dd, 1H), 2.13 (m, 1H), 2.56 (m, 1H), 3.80 (t, 1H), 4.13 (dd, 1H), 4.77 (s, 2H), 5.95 (dd, 1H), 6.85 (dd, 1H), 8.24 (t, 1H).

Step 3: 3-(azidomethyl)-6-fluoro-1-(tetrahydro-2H-pyran-2-yl)-1H-pyrazolo[3,4-b]pyridine (2-4)

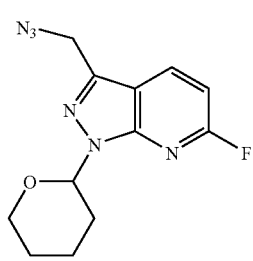

2-4

A solution of 2-3 (155 mg; 0.49 mmol) in 1 mL anhydrous DMF under nitrogen was treated with NaN₃ (32 mg; 0.49 mmol), and the solution heated at 80° C. LC-MS after 30 minutes indicated the reaction was complete, and the reaction mixture was concentrated in vacuo to give the title product as a yellow oil/solid. ¹H NMR (CDCl₃): 1.63 (m, 1H), 1.78 (complex, 2H), 1.94 (dd, 1H), 2.31 (m, 1H), 2.58 (m, 1H), 3.80 (dt, 1H), 4.14 (dd, 1H), 4.70 (q, 2H), 5.97 (dd, 1H), 6.84 (dd, 1H), 8.19 (t, 1H).

Step 4: 3-(aminomethyl)-6-fluoro-1-(tetrahydro-2H-pyran-2-yl)-1H-pyrazolo[3,4-b]pyridine (2-5)

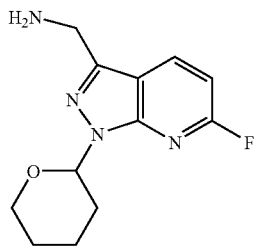

2-5

Compound 2-4 (135 mg; 0.49 mmol) was hydrogenated in the presence of 10% Pd on carbon catalyst (25 mg) under 1 atmosphere hydrogen pressure (balloon) at room temperature. After 45 minutes LC-MS indicated that the reduction was complete. The reaction mixture was filtered through Celite, and the filtrate concentrated in vacuo to give the title product as a clear oil/solid. MS M+1=251. ¹H NMR (CDCl₃): 1.61 (m, 1H), 1.78 (m, 2H), 1.92 (dd, 1H), 2.03 (br m, 1H), 2.13 (br m, 1H), 2.60 (br m, 1H), 3.80 (br t, 1H), 4.12 (dd, 1H), 4.22 (br s, 2H), 5.93 (dd, 1H), 6.78 (dd, 1H), 8.21 (t, 1H).

Step 5: 3-chloro-5-{[5-chloro-3-fluoro-6-({[6-fluoro-1-(tetrahydro-2H-pyran-2-yl)-1H-pyrazolo[3,4-b]pyridin-3-yl]methyl}amino)pyridin-2-yl]oxy}benzonitrile (2-6)

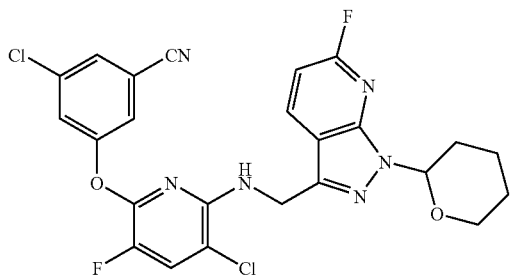

2-6

A solution of 2-5 (75 mg; 0.30 mmol) and 1-6 (90 mg; 0.30 mmol) in anhydrous NMP (2 mL) was heated with stirring at 80° C. under nitrogen. After approximately 3 hours, LC-MS indicated that the reaction was complete. The reaction mixture was cooled and diluted with a large excess of water. The resulting mixture was extracted 2× with EtOAc, and the combined extracts washed with water and brine, dried and concentrated to give crude title product as a yellow oil/solid. Crude compound was used as is in the next reaction.

Step 6: 3-[(6-{[(6-amino-1H-pyrazolo[3,4-b]pyridin-3-yl)methyl]amino}-5-chloro-3-fluoropyridin-2-yl)oxy]-5-chlorobenzonitrile (2-7)

A solution of crude 2-6 (121 mg; 0.23 mmol) and p-methoxybenzylamine (31 mg; 0.23 mmol) in NMP (2 mL) was heated at 80° C. under nitrogen. After overnight heating LC-MS indicated that the reaction was complete. The reaction mixture was cooled and diluted with water, and the mixture extracted twice with EtOAc. Combined EtOAc extracts were washed with water and brine, dried and concentrated to an oil. The oil was purified by preparative LC (Gilson) to give 70 mg of the protected product as a yellow oil. A solution of the oil in 2 mL of TFA was heated at 60° under nitrogen. After approximately 4 hours LC-MS indicated that the reaction was complete. The reaction mixture was concentrated to a dark oil/solid. The oil was purified by reverse phase preparative LC (Gilson), and the good fractions combined and concentrated to give the desired product as an amorphous TFA salt. ¹H NMR (CDCl₃): 4.73 (d, 2H), 5.59 (br s, 1H), 6.76 (dd, 1H), 7.36 (m, 2H), 7.41 (m, 1H), 7.50 (dd, 1H), 7.97 (dd, 1H).

EXAMPLE 3

3-chloro-5-({3-chloro-2-oxo-6-[2-(1H-pyrazolo[3,4-b]pyridin-3-yl)ethyl]-1,2-dihydropyridin-4-yl}oxy)benzonitrile (3-8) and 3-chloro-5-({2-oxo-6-[2-(1H-pyrazolo[3,4-b]pyridin-3-yl)ethyl]-1,2-dihydropyridin-4-yl}oxy)benzonitrile (3-9)

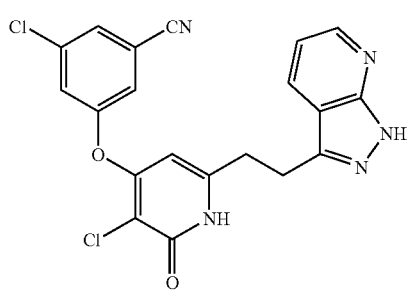

3-8

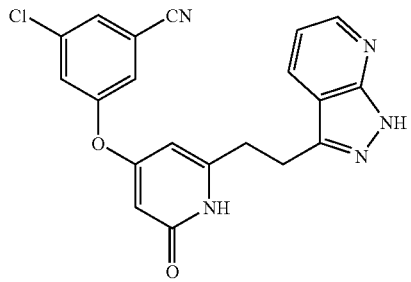

3-9

Step 1: 3-chloro-5-[(6-methyl-2-oxo-1,2-dihydropyridin-4-yl)oxy]benzonitrile (3-3)

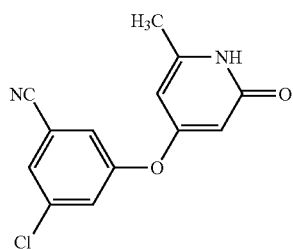

3-3

To a solution of 4-hydroxy-6-methyl-2-oxo-1,2-dihydropyridine (3-2; 20.1 g; 161 mmol) in NMP (1.6 L) was added 3-chloro-5-fluorobenzonitrile (3-1; 25 g; 161 mmol) and potassium carbonate (44.4 g; 321 mmol). The resulting solution stirred at 120° C. overnight. The reaction mixture was cooled to ambient temperature and diluted with 4 L of ice-water. The aqueous layer was acidified to pH 5 to precipitate out the product. The precipitate was collected via filtration, washed with water, and air dried. The crude solid product was triturated in 5% methanol/dichloromethane and filtered to give a solid. The solid was triturated with 1:1 ethyl acetate:hexane, stirred, and filtered to afford the title product as a tan solid. MS M+1=261.0.

$^1$H NMR (CD$_3$OD): 2.30 (s, 3H), 5.62 (s, 1H), 6.05 (s, 1H), 7.55 (s, 1H), 7.0 (s, 1H), 7.76 (s, 1H).

As an alternative to trituration, the crude product can be crystallized from methanol at a concentration of 5 mL/g to obtain the title product in sufficient purity to be used in the next step.

Step 2: 3-chloro-5-[(3-chloro-6-methyl-2-oxo-1,2-dihydropyridin-4-yl)oxy]benzonitrile (3-4)

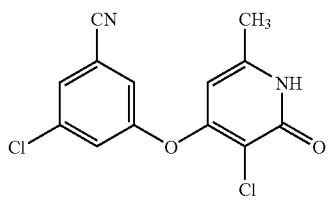

A solution of 3-3 (250 mg; 0.959 mmol) and N-chlorosuccinimide (141 mg; 1.055 mmol) in 10 mL of an acetic acid:dichloroethane mixture (1:1) was heated to 70° C. overnight. The reaction was determined to be complete via LCMS analysis. The reaction mixture was evaporated to remove volatile solvents and the residue azeotroped with toluene (2×) to yield a white solid. The crude material was purified via silica gel chromatography (0-20% MeOH in CH$_2$Cl$_2$) to afford the title compound. MS M+1=294.9. $^1$H NMR (CDCl$_3$): 2.15 (2, 3H), 5.75 (s, 1H), 7.70 (s, 1H), 7.82 (s, 1H), 7.92 (s, 1H).

As an alternative to purification via silica gel chromatography, the crude material can be crystallized from methanol at a concentration of 5 mL/g to obtain the title compound in sufficient purity to be used in the next step.

Step 3: 3-chloro-5-[(3-chloro-2-methoxy-6-methylpyridin-4-yl)oxy]benzonitrile (3-5)

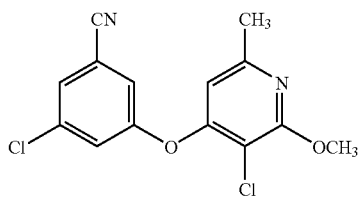

Compound 3-4 (2.45 g; 8.32 mmol), methyl iodide (1.573 mL; 25.2 mmol), silver carbonate (3.28 g; 11.89 mmol) and chloroform (100 mL) were added to a sealed vessel. The contents of the sealed vessel were heated at 50° C. for 3 hours in the absence of light. The reaction was cooled to room temperature, the insoluble material filtered off, and the filtrate concentrated in vacuo. The crude material was purified via silica gel chromatography (0-10% EtOAc in hexane) to give the title compound. MS M+1=308.9. $^1$H NMR (CDCl$_3$): 2.42 (s, 3H), 4.05 (s, 3H), 6.36 (s, 1), 7.16 (m, 1H), 7.24 (m, 1H), 7.44 (m, 1H).

Step 4: 3-{[6-(bromomethyl)-3-chloro-2-methoxypyridin-4-yl]oxy}-5-chlorobenzonitrile (3-6)

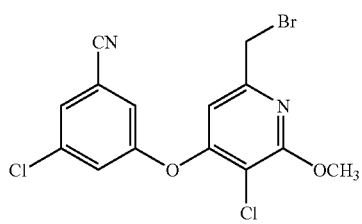

To a solution of 3-5 (1.9 g; 6.15 mmol) in carbon tetrachloride was added N-bromosuccinimide (1.31 g; 7.38 mmol) and benzoyl peroxide (0.298 mg; 1.23 mmol). The reaction mixture was heated at reflux for 5 hours, cooled to room temperature, and concentrated to a solid. The crude mixture was purified via column chromatography (0-10% EtOAc in hexane) to give the title compound. MS M+1=388.8. $^1$H NMR (CDCl$_3$): 4.08 (s, 3H), 4.38 (s, 2H), 6.60 (s, 1H), 7.16 (s, 1H), 2.26 (s, 1H), 7.44 (s, 1H).

Step 5: tert-butyl 3-{(E)-2-[5-chloro-4-(3-chloro-5-cyanophenoxy)-6-methoxypyridin-2-yl]vinyl}-1H-pyrazolo[3,4-b]pyridine-1-carboxylate (3-7)

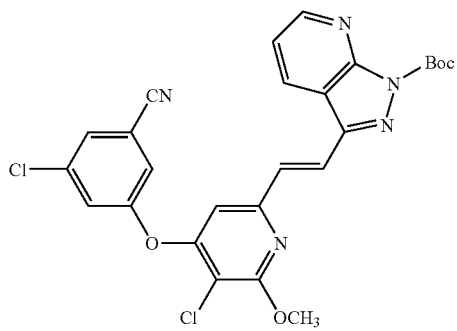

Compound 3-6 (735 mg; 2.08 mmol) and triphenylphosphine (545 mg; 2.08 mmol) were added to toluene (20 mL) and the mixture heated at reflux for 2 hours. The reaction mixture was concentrated to remove the volatile liquids to give the crude phosphonium bromide salt, which was used with no further purification. The phosphonium bromide salt (800 mg; 0.8 mmol) was dissolved in DMF and cooled to 0° C. using an ice-water bath. Potassium carbonate (774 mg; 5.60 mmol) was added to the reaction mixture and the ice-water bath was removed and the reaction mixture allowed to warm to ambient temperature. After stirring at room temperature for 30 minutes, Intermediate I-A (198 mg; 0.800 mmol) was added as a solution in DMF and the resulting mixture was heated to 72° C. for 2 hours. The reaction mixture was then cooled to room temperature and was diluted with water and EtOAc. The aqueous layer was extracted three times with EtOAc, and the combined organic layers washed with water (4×) and brine (1×), dried over magnesium sulfate, and evaporated to an oil. The crude material was purified via silica gel chromatography (0-70% EtOAc in hexane) to yield the desired product as white solid. MS M+1=538.0. $^1$H NMR (CDCl$_3$): 1.75 (s, 9H), 4.18 (s, 3H), 6.58 (s, 1H), 7.22 (m, 1H), 7.30 (m, 1H), 7.34-7.40 (m, 2H), 7.48 (m, 1H), 7.94 (m, 1H), 7.98 (m, 1H), 8.34-8.38 (d, 1H), 8.76-8.78 (m, 1H).

Step 6: 3-chloro-5-({3-chloro-2-oxo-6-[2-(1H-pyrazolo[3,4-b]pyridin-3-yl)ethyl]-1,2-dihydropyridin-4-yl}oxy)benzonitrile (3-8)

To a solution of 3-7 (270 mg; 0.50 mmol) in a 1:1 mixture of THF:ethanol (40 mL) was added 10% Pd/C (130 mg; 1.22 mmol). The reaction mixture was purged with nitrogen (3×), hydrogen (3×), and then stirred under atmospheric pressure of hydrogen for 2.5 hours at room temperature. The reaction mixture was filtered and concentrated to a solid. The crude material was dissolved in 10 mL DME:hydrobromic acid (48% in water) (1:1) and the reaction mixture was then heated with stirring at 50° C. for 2 hours. The reaction was cooled to room temperature and diluted with water and EtOAc. The pH of the aqueous layer was adjusted to 6, and the aqueous layer extracted with EtOAc (3×). The combined organic layers were washed with water (4×), brine (2×), dried over MgSO$_4$, and concentrated. The crude material was purified by reverse phase preparative HPLC on a Gilson apparatus to give the title compound as a white solid. MS M+1=425.7. $^1$H NMR (DMSO-d$_6$): 2.90 (m, 2H), 3.18 (m, 2H), 5.96 (s, 1H), 7.12 (m, 1H), 7.60 (m, 1H), 7.68 (s, 1H), 7.88 (m, 1H), 8.22 (m, 1H), 8.45 (m, 1H), 12.32 (bs, 1H), 13.26 (bs, 1H).

Step 7: 3-chloro-5-({2-oxo-6-[2-(1H-pyrazolo[3,4-b]pyridin-3-yl)ethyl]-1,2-dihydropyridin-4-yl}oxy)benzonitrile (3-9)

In a manner identical to that described above in Step 6 for Compound 3-8, from Compound 3-7 (325 mg; 0.604 mmol) was collected Compound 3-8 and the title compound 3-9 as a by product. MS M+1=391.8: $^1$H NMR (DMSO-d$_6$): 2.90 (m, 2H), 3.20 (m, 2H), 5.75 (s, 1H), 7.12 (m, 1H), 7.20 (m, 1H), 7.55 (m, 1H), 7.64 (m, 2H), 8.20 (m, 1H), 8.45 (m, 1H), 12.30 (s, 1H), 13.25 (s, 1H).

EXAMPLE 4

3-({6-[2-(6-amino-1H-pyrazolo[3,4-b]pyridin-3-yl)ethyl]-3-chloro-2-oxo-1,2-dihydropyridin-4-yl}oxy)-5-chlorobenzonitrile (4-4)

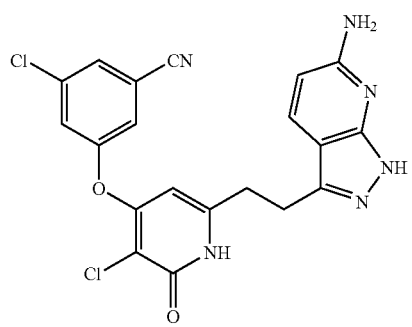

4-4

Step 1: 3-chloro-5-[(3-chloro-6-{(E)-2-[6-fluoro-1-(4-methoxybenzyl)-1H-pyrazolo[3,4-b]pyridin-3-yl]vinyl}-2-methoxypyridin-4-yl)oxy]benzonitrile (4-1)

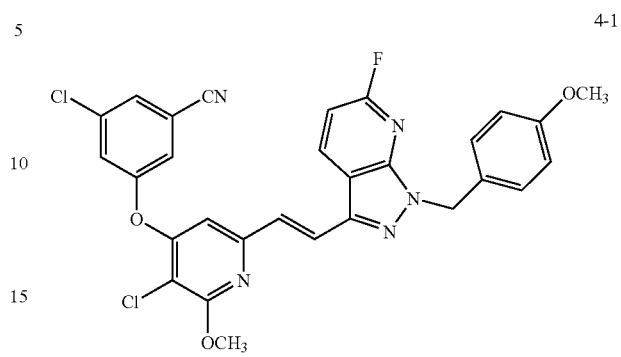

4-1

A mixture of 3-6 (900 mg; 2.32 mmol) and triphenylphosphine (608 mg; 2.32 mmol) were added to toluene (20 mL) and heated at reflux for 2 hours. Removal of the volatile liquids yielded the phosphonium bromide salt (M+1=568.7) as a white solid. Potassium carbonate (1.71 mg; 12.3 mmol) was added to a solution of the crude phosphonium bromide (1.15 g; 1.768 mmol) in DMF at 0° C. (ice-water bath). The ice-water bath was then removed immediately and the reaction mixture allowed to warm to ambient temperature. After stirring at room temperature for 30 minutes, Intermediate I-E (198 mg; 0.800 mmol) was added as a solution in DMF and the resulting mixture was heated to 72° C. for 1.5 hours. The reaction mixture was then cooled to room temperature and diluted with water and EtOAc. The aqueous layer was extracted with EtOAc (3×), and the combined org. layers washed with water (4×), brine (1×), dried over magnesium sulfate, and concentrated. The crude material was purified via silica gel chromatography to give the title compound. MS M+1=575.6. $^1$H NMR (CDCl$_3$): 3.78 (s, 3H), 4.18 (s, 3H), 5.55 (s, 2H), 6.55 (s, 1H), 6.82 (m, 3H), 7.16 (d, 1H), 7.21 (m, 1H), 7.30 (m, 1H), 7.34 (d, 2H), 7.48 (m, 1H), 7.86 (d, 1H), 8.35 (dd, 1H).

Step 2: 3-chloro-5-[(3-chloro-6-{2-[6-fluoro-1-(4-methoxybenzyl)-1H-pyrazolo[3,4-b]pyridin-3-yl]ethyl}-2-methoxypyridin-4-yl)oxy]benzonitrile (4-2)

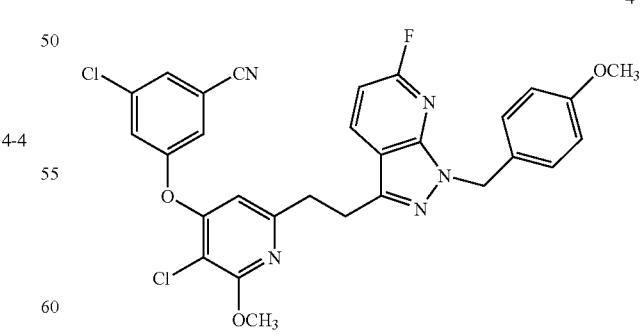

4-2

Compound 4-1 (400 mg; 0.694 mmol) was dissolved in 6 mL THF/MeOH (1:1) and the system purged with nitrogen (3×). 10% Pd/C (739 mg; 0.694 mmol) was then added to the reaction mixture which was then purged (3×) with nitrogen and then with hydrogen (3×). The purged reaction mixture Step 3: 3-chloro-5-{[3-chloro-2-methoxy-6-(2-{1-(4-methoxybenzyl)-6-[(4-methoxybenzyl)amino]-1H-pyrazolo[3,4-b]pyridin-3-yl}ethyl)pyridin-4-yl]oxy}benzonitrile (4-3)

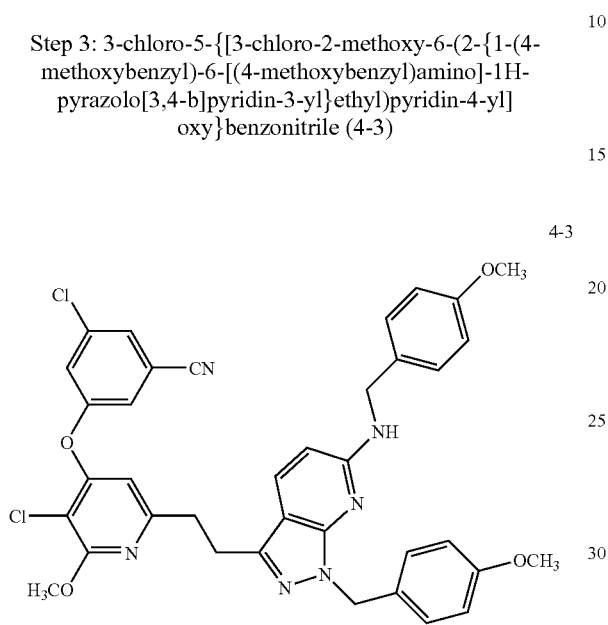

To a solution of 4-2 (300 mg; 0.519 mmol) in DMSO (2 mL) was added p-methoxybenzylamine (285 mg; 2.075 mmol). The reaction mixture was heated with stirring overnight at 85° C. The reaction mixture was then cooled to room temperature, diluted with water, and the aqueous layer extracted with EtOAc (3×). Combined organic layers were washed with water (4×), brine (1×), dried over MgSO$_4$, and concentrated to yield an oil. The crude oil was purified via silica gel chromatography (10-60% EtOAc in hexane) to give the title compound.

MS M+1=694.6 $^1$H NMR (CDCl$_3$): 3.04 (t, 2H), 3.20 (t, 2H), 3.74 (s, 3H), 3.80 (s, 3H), 4.02 (s, 3H), 4.58 (m, 2H), 4.94 (m, 1H), 5.38 (s, 2H), 6.16 (d, 1H), 6.26 (s, 1H), 6.74 (d, 2H), 6.84 (d, 2H), 7.20 (m, 1H), 7.12 (m, 1H), 7.16 (d, 1H), 7.28 (d, 2H), 7.38 (m, 1H), 7.4 (d, 1H).

Step 4: 3-({6-[2-(6-amino-1H-pyrazolo[3,4-b]pyridin-3-yl)ethyl]-3-chloro-2-oxo-1,2-dihydropyridin-4-yl}oxy)-5-chlorobenzonitrile (4-4)

A solution of 4-3 (271 mg; 0.390 mmol) in TFA (12 mL) was heated to 65° C. for 2 hours. The volatile material was then removed and the crude residue dissolved in 12 mL of DME:12N HCl (1:1). The mixture was heated to 65° C. for 4 hours, cooled to room temperature, and the volatile material removed. The crude residue was then dissolved in DMF, filtered, and purified by reverse phase preparative HPLC on a Gilson apparatus to give the title compound.

MS M+1=440.7. $^1$H NMR (CD$_3$OD) 3.90 (m, 2H), 3.25 (m, 2H), 5.72 (s, 1H), 6.54 (d, 1H), 7.34 (d, 2H), 7.68 (s, 1H), 7.96 (m, 1H).

EXAMPLE 5

3-chloro-5-({3,5-dichloro-2-oxo-6-[2-(1H-pyrazolo[3,4-b]pyridin-3-yl)ethyl]-1,2-dihydropyridin-4-yl}oxy)benzonitrile (5-6) and ethyl 3-chloro-5-({3,5-dichloro-2-oxo-6-[2-(1H-pyrazolo[3,4-b]pyridin-3-yl)ethyl]-1,2-dihydropyridin-4-yl}oxy)benzoate (5-7)

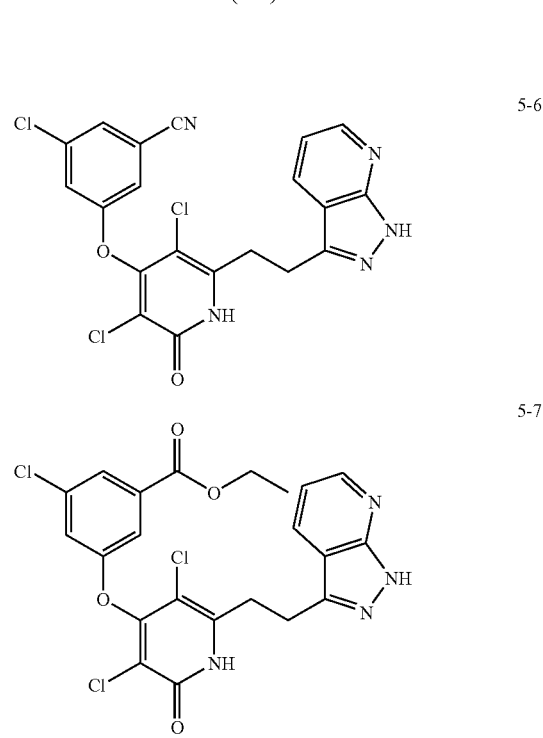

Step 1: 3-chloro-5-[(3,5-dichloro-6-methyl-2-oxo-1,2-dihydropyridin-4-yl)oxy]benzonitrile (5-1)

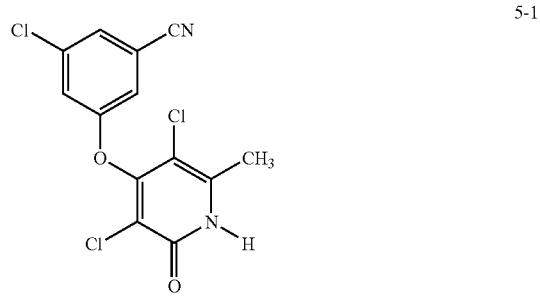 [SMILES: Cc1[nH]c(=O)c(Cl)c(Oc2cc(Cl)cc(C#N)c2)c1Cl]

A solution of Compound 3-3 (3 g; 11.5 mmol) and N-chlorosuccinimide (3.23 g; 24.17 mmol) in 60 mL of an acetic acid:dichloroethane mixture (1:2) was heated to 70° C. for 2 hours. The reaction was concentrated in vacuo to remove volatile solvents, and the residue azeotroped with toluene (2×) to yield a crude solid. The crude product was purified via silica gel chromatography (0-15% MeOH in CH$_2$Cl$_2$) to give title compound. MS M+1=330.8. $^1$H NMR (DMSO) 2.30 (s, 3H), 7.62 (m, 2H), 7.80 (s, 1H), 12.72 (s, 1H).

Step 2: 3-chloro-5-[(3,5-dichloro-2-methoxy-6-methylpyridin-4-yl)oxy]benzonitrile (5-2)

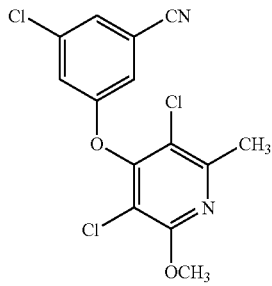

Compound 5-1 (3.2 g; 9.71 mmol), methyl iodide (1.21 mL; 19.4 mmol), silver carbonate (8.03 g; 29.1) mmol) and chloroform (100 mL) were added to a sealed vessel. The contents of the sealed vessel were heated at 50° C. overnight in the absence of light. The reaction mixture was cooled to room temperature, filtered to remove insoluble material, and the filtrate concentrated in vacuo. The crude material was purified via silica gel chromatography (0-15% EtOAc in hexane) to give the title compound. MS M+1=344.8. $^1$H NMR (CDCl$_3$): 2.58 (s, 3H), 4.06 (s, 3H), 6.96 (m, 1H), 7.20 (m, 1H), 7.38 (m, 1H).

Step 3: 3-{([2-(bromomethyl)-3,5-dichloro-6-methoxypyridin-4-yl]oxy}-5-chlorobenzonitrile (5-3)

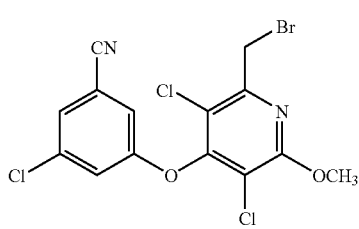

In a manner identical to that described above for the synthesis of Compound 3-6, the title product was obtained as a clear oil from Compound 5-2 (1.30 g; 3.78 mmol). MS M+1=422.5. $^1$H NMR (CDCl$_3$): 4.10 (s, 3H), 4.60 (s, 2H), 6.96 (s, 1H), 7.12 (s, 1H), 7.40 (s, 1H).

Step 4: tert-butyl 3-{(E)-2-[3,5-dichloro-4-(3-chloro-5-cyanophenoxy)-6-methoxypyridin-2-yl]vinyl}-1H-pyrazolo[3,4-b]pyridine-1-carboxylate (5-4)

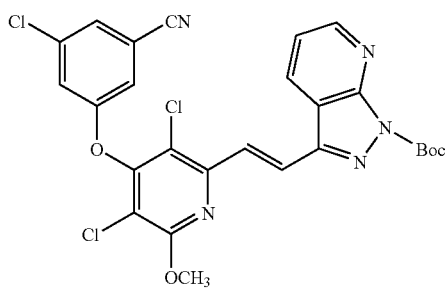

Compound 5-3 (1.0 g; 2.36 mmol) and triphenylphosphine (0.62 g; 2.36 mmol) were added to toluene (60 mL) and the mixture heated at reflux for 2 hours. The volatile liquids were evaporated and the residue was redissolved in 10 mL DMF. The reaction mixture was cooled to 0° C. using an ice-water bath and was then treated with potassium carbonate (565 mg; 4.09 mmol). Upon addition of the carbonate, the ice-water bath was removed and the reaction mixture allowed to warm to room temperature. After stirring at room temperature for 30 minutes, Intermediate I-A (144 mg; 0.584 mmol) was added as a solution in DMF and the resulting mixture was heated at 72° C. for 2 hours. The reaction mixture was then cooled to room temperature and diluted with water and EtOAc. The aqueous layer was extracted 3× with EtOAc and the combined organic extracts washed with water (4×), brine (1×), dried over magnesium sulfate, and evaporated to an oil. The crude oil was purified via silica gel chromatography (0-100% EtOAc in hexane) to give the title compound as white/yellow solid. MS M+1=473.6 (loss of Boc under LCMS conditions). $^1$H NMR (CDCl$_3$): 1.75 (s, 9H), 4.20 (s, 3H), 7.05 (m, 1H), 7.16 (m, 1H), 7.40 (m, 2H), 7.90 (d, 1H), 8.19 (d, 1H), 8.41 (m, 1H), 8.80 (m, 1H).

Step 5: tert-butyl 3-{2-[3,5-dichloro-4-(3-chloro-5-cyanophenoxy)-6-methoxypyridin-2-yl]ethyl}-1H-pyrazolo[3,4-b]pyridine-1-carboxylate (5-5)

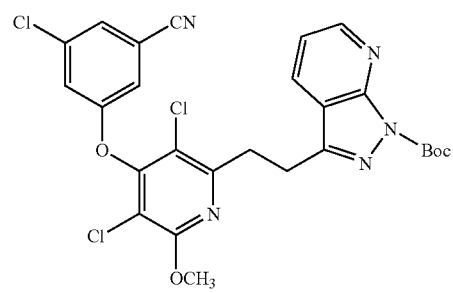

A solution of 5-4 (382 mg; 0.667 mmol) in ethanol/THF/methanol (20 mL:15 mL:2 mL) was purged with nitrogen (3×). 10% Pd/C (270 mg; 2.54 mmol) was added to the reaction mixture which was then purged with nitrogen (3×), and then with hydrogen (3×), and then left under atmospheric pressure of hydrogen overnight at room temperature. The reaction mixture was filtered through celite and the filtrate concentrated in vacuo. The crude residue was purified by flash chromatography (20-60% EtOAc in hexane) to give the title compound. MS M+1=475.5. $^1$H NMR (CDCl$_3$): 1.70 (s, 9H), 3.40 (m, 4H), 3.95 (s, 3H), 6.92 (s, 1H), 7.08 (m, 1H), 2.28 (m, 1H), 7.35 (m, 1H), 8.0 (dd, 1H), 8.70 (m, 1H).

Step 6: 3-chloro-5-({3,5-dichloro-2-oxo-6-[2-(1H-pyrazolo[3,4-b]pyridin-3-yl)ethyl]-1,2-dihydropyridin-4-yl}oxy)benzonitrile (5-6) and ethyl 3-chloro-5-({3,5-dichloro-2-oxo-6-[2-(1H-pyrazolo[3,4-b]pyridin-3-yl)ethyl]-1,2-dihydropyridin-4-yl}oxy)benzoate (5-7)

Compound 5-5 was dissolved in 2:1 EtOH:concentrated HCl and the reaction mixture was heated for 7 days at 65° C. The volatile liquids were removed in vacuo and the residue purified by reverse phase preparative HPLC on a Gilson apparatus to give 5-6 and 5-7.

5-6: MS M+1=461.5. $^1$H NMR (DMSO): 3.10 (m, 2H), 3.22 (m, 2H), 7.18 (m, 2H), 7.60 (m, 2H), 7.80 (m, 1H), 8.22 (m, 1H), 8.45 (m, 1H), 12.84 (bs, 1H), 13.30 (bs, 1H).

5-7: MS M+1=508.5. $^1$H NMR (DMSO-d$_6$): 1.30 (m, 3H), 3.10 (m, 2H), 3.22 (m, 2H), 4.30 (m, 2H), 7.18 (m, 1H), 7.40 (m, 1H), 7.45 (m, 1H), 7.66 (m, 1H), 8.22 (m, 1H), 8.46 (m, 1H), 12.84 (bs, 1H), 13.30 (bs, 1H).

EXAMPLE 6

3-chloro-5-({5-chloro-2-[2-(1H-pyrazolo[3,4-b]pyridin-3-yl)ethyl]pyridin-4-yl}oxy)benzonitrile (6-5)

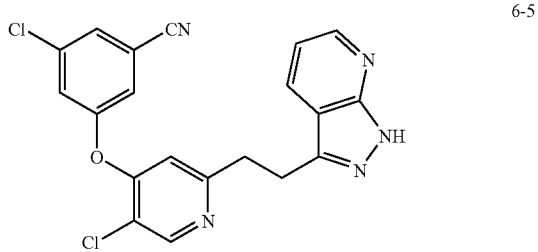 [SMILES: N#Cc1cc(Cl)cc(Oc2cc(CCc3n[nH]c4ncccc34)ncc2Cl)c1]

6-5

Step 1: 3-chloro-4-(3-chloro-5-cyanophenoxy)-6-methylpyridin-2-yl trifluoromethanesulfonate (6-1)

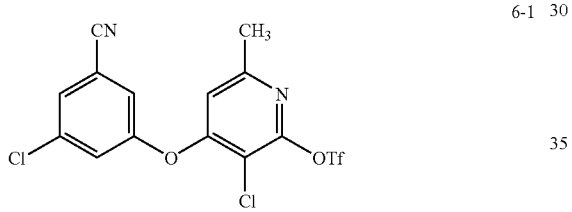

6-1

To a cooled solution (0° C.) of 3-4 (2.0 g; 3.39 mmol) in CH$_2$Cl$_2$ was added TEA (0.567 mL; 4.07 mmol) and trifluoromethanesulfonic anhydride (0.63 mL, 3.73 mmol). The reaction mixture was stirred for 1 hour at 0° C., then quenched with 0.1 N HCl and extracted with EtOAc (3×). The combined organic layers were washed with brine (1×) and then concentrated to a residue. The crude material was purified via silica gel column chromatography (0-30% EtOAc in hexane) to give the title compound. MS M+1=426.6. $^1$H NMR (CDCl$_3$): 2.48 (s, 3H), 6.62 (s, 1H), 7.30 (m, 1H), 7.36 (m, 1H), 7.58 (m, 1H).

Step 2: 3-chloro-5-[(5-chloro-2-methylpyridin-4-yl)oxy]benzonitrile (6-2)

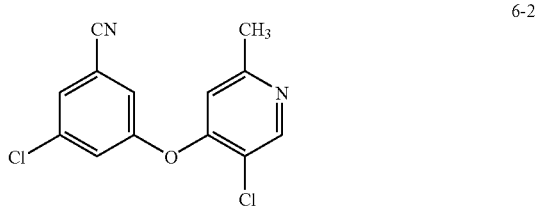 [SMILES: Cc1cc(Oc2cc(Cl)cc(C#N)c2)c(Cl)cn1]

6-2

To a solution of 6-1 (900 mg; 2.11 mmol) in DMF (20 mL) was added triphenylphosphine (55.3 mg; 0.211 mol), palladium (II) acetate (23.65 mg; 0.105 mol), TEA (0.88 mL; 6.32 mmol), and formic acid (0.162 mL; 4.21 mmol). The reaction mixture was purged with nitrogen and heated to 60° C. for 1.5 hours and then cooled to room temperature, after which the aqueous layer was extracted with EtOAc (2×). The combined organic layers were washed with water (4×), brine (2×), dried over MgSO$_4$, and concentrated. The crude residue was purified using silica gel chromatography (0-100% EtOAc in hexane) to give the title compound. MS M+1=278.9. $^1$H NMR (CDCl$_3$): 2.45 (s, 3H), 6.65 (s, 1H), 7.15 (m, 1H), 7.25 (m, 1H), 7.50 (m, 1H), 8.50 (s, 1H).

Step 3: 3-{[2-(bromomethyl)-5-chloropyridin-4-yl]oxy}-5-chlorobenzonitrile (6-3)

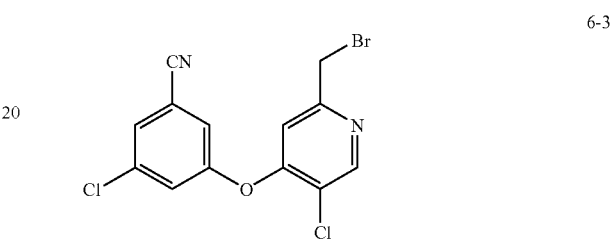

6-3

In a manner identical to that described above for Compound 3-6, the title compound was obtained as a white solid from 6-2 (200 mg; 0.717 mmol). MS M+1=356.7. $^1$H NMR (CDCl$_3$): 4.45 (s, 2H), 6.96 (s, 1H), 7.22 (m, 1H), 7.32 (m, 1H), 7.54 (m, 1H), 8.60 (s, 1H).

Step 4: tert-butyl 3-{(E)-2-[5-chloro-4-(3-chloro-5-cyanophenoxy)pyridin-2-yl]vinyl}-1H-pyrazolo[3,4-b]pyridine-1-carboxylate (6-4)

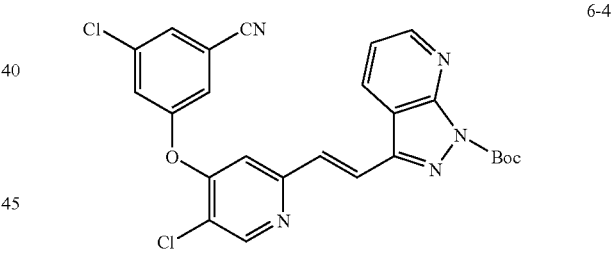

6-4

A mixture of 6-3 (90 mg; 0.251 mmol) and triphenylphosphine (66 mg; 0.251 mmol) in toluene (10 mL) was heated at reflux for 2 hours. The volatile liquids were removed by evaporation, and the residue dissolved in DMF. The DMF solution was cooled to 0° C. using an ice-water bath. Potassium carbonate (234 mg; 1.69 mmol) was then added to the reaction mixture and the ice-water bath removed. After stirring at room temperature for 30 minutes, Intermediate I-A (60 mg; 0.242 mmol) was added as a solution in DMF and the resulting mixture was heated at 72° C. for 1.5 hours. The reaction mixture was cooled to room temperature and diluted with water and EtOAc. The aqueous layer was extracted 3× with EtOAc and the combined organic layers washed with water (4×), brine (1×), dried over magnesium sulfate, and evaporated to an oil. The crude oil was purified via silica gel chromatography (0-70% EtOAc in hexane) to give the title compound as a white solid. MS M+1=507.8. $^1$H NMR (CDCl$_3$): 1.70 (s, 9H), 6.92 (s, 1H), 7.12 (m, 1H), 7.30 (m, 2H), 7.50 (m, 2H), 7.80 (d, 1H), 8.32 (m, 1H), 8.62 (s, 1), 8.74 (m, 1H).

81

Step 5: 3-chloro-5-({5-chloro-2-[2-(1H-pyrazolo[3,4-b]pyridin-3-yl)ethyl]pyridin-4-yl}oxy)benzonitrile (6-5)

To a solution of 6-4 (45 mg; 0.089 mmol) in a 1/1 mixture of THF/ethanol (6 mL) was added 10% Pd/C (36 mg; 0.338 mmol). The reaction mixture was purged with nitrogen (3×), hydrogen (3×), and stirred under atmospheric pressure of hydrogen for 18 hours at room temperature. The reaction mixture was filtered and the filtrate concentrated to a solid. The crude material was dissolved in TFA (8 mL) and stirred for 25 minutes at room temperature. The volatile liquids were removed in vacuo, and the crude residue purified by reverse phase preparative HPLC on a Gilson apparatus to give the title compound as a white solid. MS M+1=409.8. $^1$H NMR (CDCl$_3$): 3.30 (m, 2H), 3.40 (m, 2H), 6.70 (s, 1H), 7.12 (m, 1H), 7.16 (m, 1H), 7.20 (m, 1H), 7.50 (m, 1H), 8.06 (d, 1H), 8.50 (m, 1H), 8.58 (s, 1H).

EXAMPLE 7

3-chloro-5-{[3,5-dichloro-2-methyl-6-(1H-pyrazolo[3,4-b]pyridin-3-ylmethoxy)pyridin-4-yl]oxy}benzonitrile (7-1)

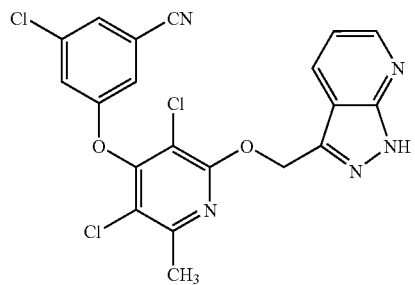

7-1

A solution of 5-1 (500 mg; 1.51 mmol), 2-1 (1.42 g; 4.55 mmol), and silver carbonate (837 mg; 3.03 mmol) in chloroform was heated in a sealed vessel at 50° C. in the absence of light for 18 hours. The reaction mixture was cooled to room temperature, and the solids filtered off and the filtrate concentrated in vacuo. The crude residue was dissolved in TFA and stirred for 30 minutes. The TFA was evaporated in vacuo and the crude residue purified by silica gel chromatography to give the title compound. MS M+1=461.5. $^1$H NMR (DMSO-d$_6$): 2.60 (s, 3H), 5.78 (s, 2H), 7.24 (m, 1H), 7.61 (m, 2H), 7.82 (m, 1H), 8.36 (m, 1H), 8.54 (m, 1H), 13.70 (s, 1H).

EXAMPLE 8

3-chloro-5-({3-chloro-2-oxo-6-[(1H-pyrazolo[3,4-b]pyridin-3-ylmethyl)amino]-1,2-dihydropyridin-4-yl}oxy)benzonitrile (8-5)

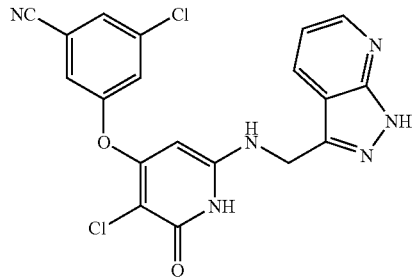

8-5

82

Step 1: 3-chloro-5-[(2,6-difluoropyridin-4-yl)oxy]benzonitrile (8-1)

Compound 1-4 (577 mg; 3.76 mmol) and potassium carbonate (779 mg; 5.64 mmol) were added to a solution of 2,4,6 trifluoropyridine (500 mg; 3.76 mmol) in DMF with stirring at −50° C. The reaction mixture was slowly warmed to room temperature and then diluted water and EtOAc, after which the aqueous layer was extracted with EtOAc. The combined organic layers were washed with water (3×), brine (2×), dried over MgSO$_4$, and concentrated to an oil. The crude residue was purified via column chromatography (0-25% EtOAc in hexanes.) to give the title compound. MS M+1=266.9. $^1$H NMR (CDCl$_3$): 6.32 (m, 2H), 7.30 (m, 1H), 7.36 (m, 1H), 7.56 (m, 1H).

Step 2: 3-{[2-(benzyloxy)-6-fluoropyridin-4-yl]oxy}-5-chlorobenzonitrile (8-2)

Sodium hydride (14 mg; 0.356 mmol) was added to a solution of benzyl alcohol (36 mg; 0.338 mmol) in THF, and the resulting solution stirred for 15 minutes. A solution of 8-1 (100 mg; 0.375 mmol) in THF (3 mL) was then added and the reaction mixture stirred overnight at room temperature. The reaction was then quenched with water, and extracted with EtOAc (3×). The combined organic layers were washed with brine (3×), dried over MgSO$_4$, and concentrated to an oil. The crude residue was purified via silica gel chromatography (0-20% EtOAc in hexanes) to give the title compound. MS M+1=354.9. $^1$H NMR (CDCl$_3$): 5.36 (s, 2H), 6.14 (m, 2H), 7.30 (m, 1H), 7.35-7.42 (m, 4H), 7.44 (m, 2H), 7.54 (m, 1H).

Step 3: 3-{[2-(benzyloxy)-3-chloro-6-fluoropyridin-4-yl]oxy}-5-chlorobenzonitrile (8-3)

NCS (565 mg 4.23 mmol) was added to a solution of 8-2 (1.0 g; 2.82 mmol) in 10 mL of DCE/acetic acid (1:1) and the resulting reaction mixture was heated with stirring at 70° C. for 12 hours. The reaction mixture was then allowed to cool to room temperature, concentrated, and the residue purified using silica gel chromatography (10-60% EtOAc in hexanes) to give the title compound. MS M+1=388.8. $^1$H NMR (CDCl$_3$): 5.48 (s, 2H), 6.08 (m, 1H), 7.24 (m, 1H), 7.34 (m, 1H) 7.36-7.44 (m, 3H), 7.50-7.58 (m, 3H).

Step 4: 3-({2-(benzyloxy)-3-chloro-6-[(1H-pyrazolo[3,4-b]pyridin-3-ylmethyl)amino]pyridin-4-yl}oxy)-5-chlorobenzonitrile (8-4)

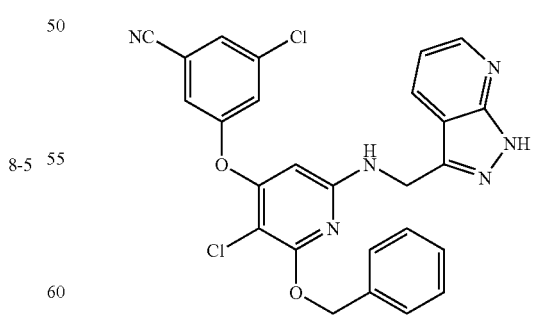

8-4

Compound 1-3 (38 mg; 0.257 mmol) was added to a solution of 8-3 (100 mg; 0.257 mmol) in NMP (2.5 mL), and the resulting reaction mixture was heated to 80° C. for 18 hours. The reaction mixture was then cooled to room temperature and diluted with water and EtOAc. The aqueous layer was extracted with EtOAc (3×), and the combined organic layers washed with water (3×), brine (2×), and dried over MgSO$_4$. The extract was concentrated to an oil and the crude oil purified via silica gel chromatography (0-10% MeOH in CH$_2$Cl$_2$) to give the title compound. MS M+1 517.1. $^1$H NMR (CDCl$_3$): 5.12 (m, 1H), 5.45 (m, 4H), 6.08 (s, 1H), 7.15 (m, 1H), 7.18 (m, 1H), 7.30-7.55 (m, 7H), 8.04 (d, 1H), 8.58 (d, 1H), 10.55 (bs, 1H).

Step 5: 3-chloro-5-({3-chloro-2-oxo-6-[(1H-pyrazolo[3,4-b]pyridin-3-ylmethyl)amino]-1,2-dihydropyridin-4-yl}oxy)benzonitrile (8-5)

10% Pd/C (17 mg; 0.160 mmol) was added to a solution of 8-4 (83 mg; 0.160 mmol) in methanol (1.6 mL) and the resulting reaction mixture was purged with nitrogen (3×), purged with hydrogen (3×), and then kept under atmospheric pressure of hydrogen for 48 hours at room temperature. The reaction mixture was then filtered through celite, and the filtrate concentrated and purified by reverse phase preparative HPLC on a Gilson apparatus to give the title compound. MS M+1=427.0. $^1$H NMR (DMSO-d$_6$) 4.52 (s, 2H), 5.10 (bs, 1H), 6.88 (bs, 1H), 7.10 (m, 1H), 7.50 (m, 1H), 7.60 (m, 1H), 7.80 (m, 1H), 8.15 (m, 1H), 8.44 (m, 1H), 11.16 (bs, 1H), 13.40 (bs, 1H).

EXAMPLE 9

3-chloro-5-({3-chloro-2-oxo-6-[(2-oxo-2,3-dihydro-1H-benzimidazol-1-yl)methyl]-1,2-dihydropyridin-4-yl}oxy)benzonitrile (9-8)

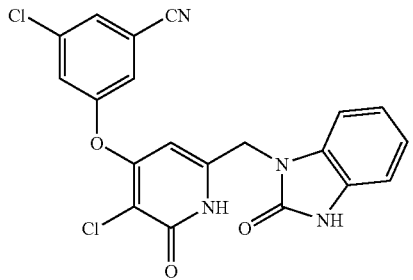

9-8

Step 1: 4-(3-bromo-5-chlorophenoxy)-6-methylpyridin-2(1H)-one (9-1)

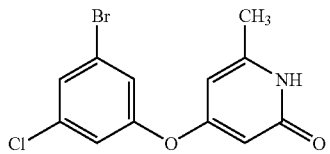

9-1

4-Hydroxy-6-methylpyridin-2(1H)-one (3-2; 10.0 g; 80 mmol) and 1-bromo-3-chloro-5-fluorobenzene (16.74 g; 80 mmol) and potassium carbonate (33.1 g; 240 mmol) were suspended in NMP (200 mL) and then heated at 140° C. for 5 days. The reaction mixture was cooled to room temperature, diluted with water (900 mL) and the pH of the solution was adjusted to 5 with concentrated HCl. The solid was filtered off, washed with water and suctioned dry. The crude material was adsorbed onto silica and purified in 2 runs on a silica column eluted with DCM:MeOH to give the title product (9-1) as a yellow solid. R$_f$=0.6(DCM:MeOH, 95:5). LCMS: M$^+$=315. $^1$H NMR (DMSO-d$_6$): δ 11.48 (s, 1H), 7.65 (s, 1H), 7.43 (s, 1H), 7.36 (s,1H), 5.86 (s, 1H), 5.36 (s, 1H), 2.16 (s, 3H).

Step 2: 4-(3-bromo-5-chlorophenoxy)-3-chloro-6-methylpyridin-2(1H)-one (9-2)

A solution of 9-1 (7.33 g; 23.30 mmol) in dichloroethane (200 mL) was treated with acetic acid (200 mL). This solution was heated to 70° C. and then NCS (2.96 g; 22.14 mmol) was added. The reaction mixture was refluxed for 4.5 hours, and then stirred overnight at 70° C. The volatiles were evaporated from the reaction mixture, and the solid residue was purified on a silica column eluted with DCM:MeOH to provide the title product (9-2). R$_f$=0.6 (DCM:MeOH, 95:5). LCMS: M+=349. $^1$H NMR (DMSO-d$_6$): δ 12.13 (s, 1H), 7.62 (s, 1H), 7.42 (s, 1H), 7.34 (s, 1H), 5.85 (s, 1H), 2.15 (s, 3H).

Step 3: 4-(3-bromo-5-chlorophenoxy)-3-chloro-2-methoxy-6-methylpyridine (9-3)

Methyl iodide (7.14 g; 50.30 mmol) and silver carbonate (4.16 g; 15.09 mmol) were added to 9-2 (3.51 g; 10.06 mmol) in chloroform, after which the reaction flask was wrapped in aluminum foil and heated at 50° C. overnight. The reaction mixture was then cooled to room temperature and the solids removed by filtration. The filtrate was concentrated, dissolved in DCM, and purified on a silica column eluted with EtOAc:hexane to give the desired product (9-3) as a crystalline solid. R$_f$=0.8 (EtOAc:hx 5:95). LCMS: M+=363. $^1$H NMR (CDCl$_3$): δ 7.31 (s, 1H), 7.05 (s, 1H), 6.95 (s, 1H), 6.27 (s, 1H), 4.00 (s, 3H), 2.35 (s, 3H).

Step 4: 4-(3-bromo-5-chlorophenoxy)-6-(bromomethyl)-3-chloro-2-methoxypyridine (9-4)

NBS (1.46 g; 8.21 mmol) and benzoyl peroxide (0.20 g; 0.82 mmol) were added to a solution of 9-3 (2.98 g; 8.21 mmol) in CCl$_4$ (200 mL) while stirring at reflux, after which the reaction mixture was refluxed overnight. The reaction mixture was then cooled, and the solids removed by filtration. The filtrate was evaporated to a crude oil. The crude material was purified via super critical CO$_2$ column chromatography to give the title product (9-4) as a solid. R$_f$=0.65 (hexanes:Et$_2$O 95:5). LCMS: M+=441. $^1$H NMR (CDCl$_3$): δ 7.38 (t, 1H), 7.11 (t, 1H), 7.00 (5, 1H), 6.57 (s, 1H), 4.35 (s, 2H), 4.06 (s, 3H).

Step 5: tert-butyl 3-{[4-(3-bromo-5-chlorophenoxy)-5-chloro-6-methoxypyridin-2-yl]methyl}-2-oxo-2,3-dihydro-1H-benzimidazole-1-carboxylate (9-6)

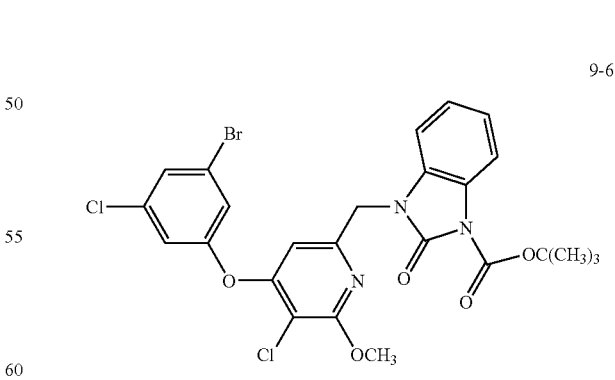

9-6

A solution of tert-butyl 2-oxo-2,3-dihydro-1H-benzimidazole-1-carboxylate (9-5; 113 mg; 0.48 mmol) in DMF (2 mL) was treated with 9-4 (193 mg; 0.44 mmol) and cesium carbonate (398 mg; 1.22 mmol). The resulting mixture was stirred at 50° C. overnight, then diluted with water and extracted with ethyl acetate. Aqueous work up and silica purification (EtOAc:hexanes) gave the title product (9-6). $R_f$=0.7 (EtOAc:hexanes 25:75). LCMS: M+=595. $^1$H NMR (CDCl$_3$): δ 7.82 (d, 1H), 7.31 (s, 1H), 7.14 (m, 2H), 7.01 (m, 2H), 6.89 (s, 1H), 6.47 (s, 1H), 4.98 (s, 2H), 3.92 (s, 3H), 1.67 (s, 9H).

Step 6: 3-chloro-5-({3-chloro-2-methoxy-6-[(2-oxo-2,3-dihydro-1H-benzimidazol-1-yl)methyl]pyridin-4-yl}oxy)benzonitrile (9-7)

A solution of 9-6 (130 mg; 0.22 mmol) in dry DMF was treated with (Ph$_3$P)$_4$Pd (50 mg; 0.044 mmol) and zinc cyanide (26 mg; 0.22 mmol). The reaction mixture was heated at 100° C. with stirring under nitrogen overnight. The reaction mixture was then cooled and the solids removed by filtration. The filtrate was evaporated and the residue was purified on a silica column eluted with MeOH:DCM to give the title product (9-7) as a solid. $R_f$=0.5 (DCM:MeOH, 95:5). LCMS: M+=442. $^1$H NMR (DMSO-d$_6$): δ 10.8 (s, 1H), 7.94 (s, 1H), 7.70 (m, 2H), 7.61 (m, 1H), 7.57 (m, 2H), 6.96 (s, 1H), 6.58 (s, 1H), 4.96 (s, 2H), 3.77 (s, 3H).

Step 7: 3-chloro-5-({3-chloro-2-oxo-6-[(2-oxo-2,3-dihydro-1H-benzimidazol-1-yl)methyl]-1,2-dihydropyridin-4-yl}oxy)benzonitrile (9-8)

An equal volume of 48% HBr was added to a suspension of 9-7 (100 mg; 0.23 mmol) in DME (3 mL). The mixture was stirred at 75° C. overnight, and then adjusted to pH 6-7 with 5N NaOH. The solids were removed by filtration, and the filtrate concentrated and then purified on a silica column eluted with DCM:MeOH to give the title product (9-8) as a solid. $R_f$=0.35 (DCM:MeOH, 95:5). HRMS: measured 427.0340 theoretical 427.0359. $^1$H NMR (DMSO-d$_6$): δ 12.41 (s, 1H), 10.98 (s, 1H), 7.85 (s, 1H), 7.60 (m, 2H), 7.04 (m, 1H), 6.96 (m, 2H), 5.54 (s, 1H), 4.85 (s, 2H).

EXAMPLE 10

3-chloro-5-({3-chloro-2,5-difluoro-6-[(1H-pyrazolo[3,4-b]pyridin-3-ylmethyl)amino]pyridin-4-yl}oxy)benzonitrile (10-4)

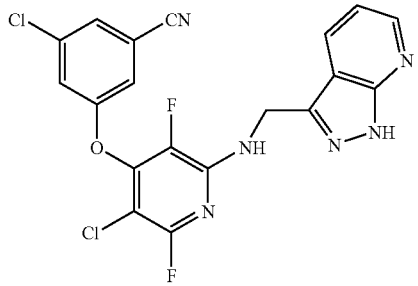

Step 1: 3-chloro-5-[(3-chloro-2,5,6-trifluoropyridin-4-yl)oxy]benzonitrile (10-2)

3-Chloro-2,4,5,6-tetrafluoropyridine (10-1; 1.0 g; 5.39 mmol) and Compound 1-4 (0.83 g; 5.39 mmol) were dissolved in DMF and the solution cooled to −50° C. under a nitrogen atmosphere, after which potassium carbonate (1.12 g; 8.09 mmol) was added and the mixture allowed to slowly warm to 25° C. The reaction mixture was quenched with water and extracted with ethyl acetate. The organic extract was concentrated and purified on a silica column eluted with ethyl acetate:hexane to give the title product 10-2 as a clear oil. $R_f$=0.6 (EtOAc:hx, 5:95). $^1$H NMR (CDCl$_3$): δ 7.50 (s, 1H), 7.24 (s, 1H), 7.17 (s, 1H).

Step 2: 3-{[2-(benzyloxy)-5-chloro-3,6-difluoropyridin-4-yl]oxy}-5-chlorobenzonitrile (10-3)

Benzyl alcohol (0.52 g; 4.76 mmol) was dissolved in dry THF and sodium hydride (0.18 g; 4.62 mmol) was added to the solution. The mixture was stirred at 25° C. for 15 minutes, after which a solution of 10-2 (1.55 g; 4.86 mmol) in THF (10 mL) was added. The reaction mixture was evaporated and purified on a silica column eluted with ethyl acetate:hexane to give the title product 10-3 as a clear oil. $R_f$=0.5 (EtOAc:hx, 5:95). $^1$H NMR (DMSO-d$_6$): δ 7.94 (t, 1H), 7.91 (t, 1H), 7.89 (m, 1H), 7.85 (m, 1H), 7.83 (m, 1H), 7.50 (d, 2H), 7.43 (t, 2H), 7.38 (m, 1H), 5.43 (s, 2H).

Step 4: 3-chloro-5-({3-chloro-2,5-difluoro-6-[(1H-pyrazolo[3,4-b]pyridin-3-ylmethyl)amino]pyridin-4-yl}oxy)benzonitrile (10-4)

10-3 (91 mg; 0.22 mmol) and 1-(1H-pyrazolo[3,4-b]pyridin-3-yl)methanamine (1-3; 43 mg; 0.29 mmol) were dissolved in dry NMP (4 mL) and the solution stirred at 80° C. overnight. The reaction mixture was then loaded onto a Gilson RP HPLC and purified to give the title product 10-4. HRMS: measured-447.0323; theoretical-447.0334. $^1$H NMR (DMSO-d$_6$): δ 13.43 (s, 1H), 8.50 (m, 1H), 8.31 (dd, 1H), 8.16 (t, 1H), 7.85 (m, 1H), 7.80 (m, 1H), 7.78 (m, 1H), 7.18 (m, 1H), 4.84 (s, 2H).

EXAMPLE 11

3-chloro-5-{[4-methyl-2-oxo-1-(1H-pyrazolo[3,4-b]pyridin-3-ylmethyl)-1,2-dihydropyridin-3-yl]oxy}benzonitrile (11-7)

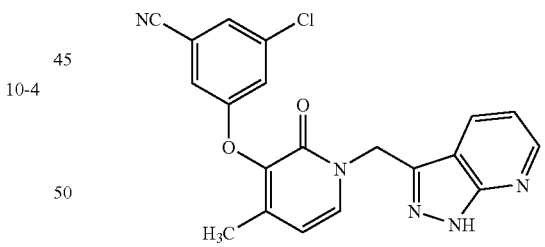

Step 1: 3-fluoro-4-methylpyridine-2-carbonitrile (11-1)

To a mixture of 2-bromo-3-fluoro-4-methylpyridine (4.89 g, 25.7 mmol) and zinc cyanide (3.02 g, 25.7 mmol) in DMF (45 mL) was added palladium tetra(triphenylphosphine) (2.97 g, 2.57 mmol). The mixture was degassed and then heated to 90° C. for 18 hours. After this time, the mixture was diluted with water (500 mL) and EtOAc (500 mL), filtered and the resulting layers were separated. The aqueous layer was further extracted with EtOAc (2×500 mL). The combined extracts were washed with water (300 mL), dried over MgSO4, filtered and the solvent removed in vacuo. The resulting residue was chromatographed using RediSep column (330 g) and eluting with a gradient of 0-100% EtOAc/CH$_2$Cl$_2$. The pure fractions were combined and the solvent removed in vacuo to give title compound.

$^1$H NMR (CDCl$_3$): δ 8.39 (d, 1H, J=4.7 Hz), 7.41 (m, 1H) and 2.41 (s, 3H) ppm.

Step 2: 3-(3-bromo-5-chlorophenoxy)-4-methylpyridine-2-carbonitrile (11-2)

A mixture of 3-fluoro-4-methylpyridine-2-carbonitrile (11-1; 2.1 g, 15.43 mmol), 3-bromo-5-chlorophenol (3.68 g, 17.74 mmol) and cesium carbonate (5.03 g, 15.43 mmol) in DMF (30 mL) was heated to 70° C. for 1 hour and then to 80° C. for 1 hour. After this time, the reaction mixture was partitioned between water (300 mL) and ethyl acetate (2×500 mL). The combined extracts were washed with water (100 mL) and then brine (100 mL), dried over MgSO$_4$, filtered and the solvent removed in vacuo. The residue was chromatographed using a RediSep column (330 g) and eluted with a gradient of 0-10% EtOAc/CH$_2$Cl$_2$ and the pure fractions combined and concentrated on the rotary evaporator to give the title compound. LRMS (M+1)=324.9.

Step 3: 3-(3-bromo-5-chlorophenoxy)-4-methylpyridine-2-carboxylic acid (11-3)

A suspension of 3-(3-bromo-5-chlorophenoxy)-4-methylpyridine-2-carbonitrile (11-2; 5 g, 15.45 mmol) in concentrated hydrochloric acid (30 mL) was heated to 100° C. for 3 hours and then to 120° C. for an additional 1.5 hours. This suspension was cooled to 50° C. and the resulting white solid was filtered, washed with water (10 mL) and dried under high vacuum to give the title compound. LRMS (M+1)=343.8.

Step 4: 3-(3-bromo-5-chlorophenoxy)-4-methylpyridin-2-amine (11-4)

To a suspension of 3-(3-bromo-5-chlorophenoxy)-4-methylpyridine-2-carboxylic acid (11-3; 2 g, 5.84 mmol) in THF (12 mL) was added triethylamine (1.627 mL, 11.68 mmol), pyridine (944 µL, 11.68 mmol), t-butanol (2.79 mL, 29.2 mmol) and diphenylphosphoryl azide (1.89 mL, 8.76 mmol) and the mixture heated to 65° C. for 35 minutes. After this time, the reaction mixture was diluted with CH$_2$Cl$_2$ (2×100 mL) and washed with water (100 mL). The combined organic extracts were concentrated to an oil on a rotary evaporator. This residue was dissolved in trifluoroacetic acid (20 mL) and allowed to stand for 15 minutes. After this time, the solvent was removed in vacuo and the residue was partitioned between CH$_2$Cl$_2$ (2×100 mL) and saturated aqueous NaHCO$_3$ (50 mL). The combined extracts were concentrated on the rotary evaporator and the residue was purified using a RediSep column (330 g) eluting with a gradient of 0-30% EtOAc/CH$_2$Cl$_2$ to give the title compound. LRMS (M+1)=314.9.

Step 5: 3-(3-bromo-5-chlorophenoxy)-4-methylpyridin-2-ol (11-5)

To an ice cooled suspension of 3-(3-bromo-5-chlorophenoxy)-4-methylpyridin-2-amine (11-4; 600 mg, 1.913 mmol) in 5% aqueous H$_2$SO$_4$ (10 mL) was added a solution of sodium nitrite (198 mg, 2.87 mmol) in water (1 mL) and stirred over ice bath for 30 minutes. After this time, this suspension was added to a solution of 5% aqueous H$_2$SO$_4$ (10 mL) heated to 100° C. and maintained at 100° C. for 1.5 hours. After this time, the mixture was cooled to 0° C. and treated with additional sodium nitrite (60 mg, 0.86 mmol) and then heated to 100° C. for 20 minutes. After this time, the mixture was cooled to 25° C., filtered the resulting solid and washed with water (10 mL) and dried under high vacuum to give the title compound.

HRMS (M+1)=313.9577.

Step 6: 3-(3-bromo-5-chlorophenoxy)-4-methyl-1-(1H-pyrazolo[3,4-b]pyridin-3-ylmethyl)pyridin-2 (1H)-one (11-6)

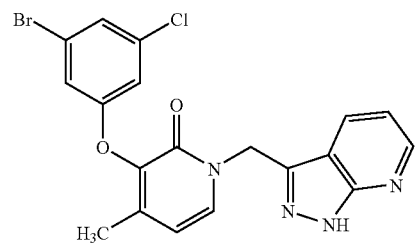

To a solution of 3-(3-bromo-5-chlorophenoxy)-4-methylpyridin-2-ol (11-5; 75 mg, 0.238 mmol) and tert-butyl 3-(bromomethyl)-1H-pyrazolo[3,4-b]pyridine-1-carboxylate (74.4 mg, 0.238 mmol) was added potassium carbonate (33 mg, 0.238 mmol) and the resulting mixture was stirred at 25° C. for 18 hours. After this time, the mixture was filtered and then purified on Gilson LC using a Luna column (10µ, C18, 250×21.2 cm) eluting with 5-95% ACN/water with 0.1% TFA). The desired fractions were concentrated to dryness and the resulting solid was dissolved in trifluoroacetic acid (2 mL) This solution was concentrated on the rotary evaporator to give the title compound. LRMS (M+1)=446.7

Step 7: 3-chloro-5-{[4-methyl-2-oxo-1-(1H-pyrazolo [3,4-b]pyridin-3-ylmethyl)-1,2-dihydropyridin-3-yl]oxy}benzonitrile (11-7)

To a suspension of 3-(3-bromo-5-chlorophenoxy)-4-methyl-1-(1H-pyrazolo[3,4-b]pyridin-3-ylmethyl)pyridin-2 (1H)-one (11-6; 100 mg, 0.224 mmol) and zinc cyanide (29 mg, 0.247 mmol) in DMF (1 mL) was added palladium tetrakis triphenylphosphine (51.9 mg, 0.045 mmol) and the mixture was degassed and heated to 90° C. for 20 minutes. After this time, additional zinc cyanide (29 mg, 0.247 mmol) and palladium tetrakis triphenylphosphine (51.9 mg, 0.045 mmol) were added and the mixture heated to 90° C. for 20 hours. The reaction mixture was then filtered through Gelman Acrodisc and purified on Gilson LC using a Luna column (10µ, C18, 250×21.2 cm) eluting with 5-95% ACN/water with 0.1% TFA). Fractions containing desired compound were combine and the solvent concentrated in vacuo on a rotary evaporator. The residue was further purified using RediSep (4 g) and eluting with a 0-65% EtOAc/CH$_2$Cl$_2$ gradient. The desired fractions were combined and the solvent removed on the rotary evaporator to provide the title compound. $^1$H NMR (CDCl$_3$): δ 11.48 (br s, 1H), 8.55 (d, 1H), 8.26 (d, 1H), 7.40 (m, 1H), 7.27 (dd, 1H), 7.14 (dd, 1H), 7.09 (dd, 1H), 6.96 (dd, 1H), 6.09 (dd, 1H), 5.48 (s, 2H) and 2.08 (s, 3H) ppm. LRMS (M+1)=392.

EXAMPLE 12

3-chloro-5-({4-methyl-2-oxo-1-[2-(1H-pyrazolo[3,4-b]pyridin-3-yl)ethyl]-1,2-dihydropyridin-3-yl}oxy)benzonitrile (12-7)

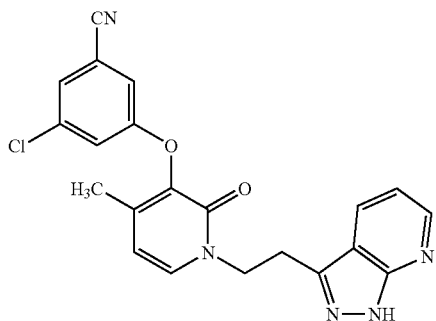 [SMILES: Cc1ccn(CCc2n[nH]c3ncccc23)c(=O)c1Oc1cc(Cl)cc(C#N)c1]

Step 1: tert-Butyl 3-(cyanomethyl)-1H-pyrazolo[3,4-b]pyridine-1-carboxylate (12-1)

To a solution of tert-butyl 3-(bromomethyl)-1H-pyrazolo[3,4-b]pyridine-1-carboxylate (5.18 g, 16.59 mmol) in DMF (30 mL) was added sodium cyanide (1.626 g, 33.2 mmol) and stirred at 25° C. for 4 hours. After this time, the mixture was diluted with water (300 mL) and extracted with ethyl acetate (3×300 mL). The extracts were combined and the resulting solid precipitate was filtered. The filtrate was dried over MgSO$_4$, filtered and the solvent removed in vacuo. This residue was purified by chromatography using 120 g RediSep column and eluting with 0-100% EtOAc/CH$_2$Cl$_2$ gradient. The desired fractions were combined and evaporated in vacuo to provide the title compound. LRMS (M+1): 259.1.

Step 2: 1H-pyrazolo[3,4-b]pyridin-3-ylacetic acid (12-2)

A solution of tert-butyl 3-(cyanomethyl)-1H-pyrazolo[3,4-b]pyridine-1-carboxylate (510 mg, 1.97 mmol) in conc. hydrochloric acid (10 mL) was heated to 100° C. for 30 minutes. After this time, the reaction was allowed to cool to room temperature and the solvent was evaporated in vacuo. This residue was further azeotroped with acetonitrile to give the title compound. LRMS (M+1):178.0.

Step 3: Methyl 1H-pyrazolo[3,4-b]pyridin-3-ylacetate (12-3)

To a solution of 1H-pyrazolo[3,4-b]pyridin-3-ylacetic acid (92 mg, 0.520 mmol) in methanol (4 mL) was bubbled in HCl gas for 2 minutes and the resulting solution was allowed to stand for a further 10 minutes. After this time, the solution was concentrated in vacuo and the resulting residue was partitioned between aqueous NaHCO$_3$ (10 mL) and ethyl acetate (2×10 mL). The combined organic extracts were washed with brine, dried over MgSO$_4$, filtered and the solvent evaporated in vacuo to provide the title compound. LRMS (M+1): 192.0.

Step 4: Methyl [1-(tetrahydro-2H-pyran-2-yl)-1H-pyrazolo[3,4-b]pyridin-3-yl]acetate (12-4)

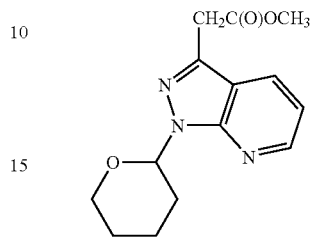

To a solution of methyl 1H-pyrazolo[3,4-b]pyridin-3-ylacetate (84 mg, 0.439 mmol) in acetonitrile (3 mL) was added DHP (37 mg, 0.439 mmol) and DDQ (10 mg, 0.044 mmol). This mixture was heated to 75° C. for 20 minutes. After this time, additional DHP (37 µL, 0.44 mmol) was added and the reaction mixture heated to 85° C. for 1.5 hours. The reaction mixture was partitioned between water (10 mL) and ethyl acetate (2×20 mL). The combined organic extracts were washed with brine, dried over MgSO$_4$, filtered and evaporated in vacuo. This residue was purified by chromatography using RediSep column (12 g) and eluting with gradient of 0-20% EtOAc/CH$_2$Cl$_2$. The desired fractions were combined and the solvent evaporated in vacuo to give the title compound. LRMS (M+1): 276.1.

Step 5: 2-[1-(tetrahydro-2H-pyran-2-yl)-1H-pyrazolo[3,4-b]pyridin-3-yl]ethanol (12-5)

To a solution methyl [1-(tetrahydro-2H-pyran-2-yl)-1H-pyrazolo[3,4-b]pyridin-3-yl]acetate (128 mg, 0.465 mmol) at 0° C. was added 2M LAH in THF (232 ul, 0.465 mmol) and stirred at 0° C. for 30 minutes. After this time, the reaction mixture was sequentially treated with water (18 ul) and 1.0N NaOH (54 ul) and stirred at 25° C. for 30 minutes. After this time, the mixture was filtered through celite and rinsing with THF. The filtrates were combined and the solvent evaporated in vacuo. The residue was purified by chromatography using RediSep column (12 g) and eluting with a gradient of 0-10% MeOH/CH$_2$Cl$_2$ to give the title compound. LRMS (M+1): 164.0.

Step 6: 3-chloro-5-[(4-methyl-2-oxo-1-{2-[1-(tetrahydro-2H-pyran-2-yl)-1H-pyrazolo[3,4-b]pyridin-3-yl]ethyl}-1,2-dihydropyridin-3-yl)oxy]benzonitrile (12-6)

To a solution of 2-[1-(tetrahydro-2H-pyran-2-yl)-1H-pyrazolo[3,4-b]pyridin-3-yl]ethanol (14.6 mg, 0.059 mmol) in CH$_2$Cl$_2$ (400 ul) was added 3-chloro-5-[(4-methyl-2-oxo-1,2-dihydropyridin-3-yl)oxy]benzonitrile (15.4 mg, 0.059 mmol), and the resulting mixture was stirred over an ice bath for 5 minutes. The mixture was then treated with triphenylphosphine (30.9 mg, 0.118 mmol) and then diisopropylazodicarboxylate (13 ul, 0.068 mmol) and stirred over an ice bath for 10 minutes and then at 25° C. for 30 minutes.

LC-MS showed the reaction was not complete, and so the mixture was re-cooled over an ice bath and treated with additional diisopropylazodicarboxylate (10 µL, 0.052 mmol). This mixture was stirred over an ice bath for 5 minutes and then stirred at 25° C. for 20 minutes to give a 3:2 mixture of 0 to N alkylation. After this time, the reaction was quenched with MeOH (1 mL) and purified on Gilson LC using a Luna reverse phase column (10µ, $C_{18}$, 250×21.2 mm) and eluting with a gradient of 5-95% ACN/water (0.5% TFA). The desired fractions were combined and evap in vacuo to give the title compound. LRMS (M+1): 489.9/405.9.

Step 7: 3-chloro-5-({4-methyl-2-oxo-1-[2-(1H-pyrazolo[3,4-b]pyridin-3-yl)ethyl]-1,2-dihydropyridin-3-yl}oxy)benzonitrile (12-7)

3-chloro-5-[(4-methyl-2-oxo-1-{2-[1-(tetrahydro-2H-pyran-2-yl)-1H-pyrazolo[3,4-b]pyridin-3-yl]ethyl}-1,2-dihydropyridin-3-yl)oxy]benzonitrile (11.7 mg, 0.023 mmol) was dissolved in TFA (2 mL) and allowed to stand at room temperature for 1 hour. After this time, MeOH (1 mL) was added and the solvent evaporated in vacuo. The residue was purified on Gilson LC using a Luna reverse phase column (10µ, $C_{18}$, 250×21.2 mm) and eluting with a gradient of 5-95% ACN/water (0.5% TFA). The desired fractions were combined and the solvent evaporated in vacuo to give the title compound. LRMS (M+1): 405.9.

NMR (DMSO-$d_6$): δ=13.34 (br s, 1H), 8.49 (d, 1H, J=4.5 Hz), 8.20 (d, 1H, J=8.0 Hz), 7.68 (s, 1H), 7.46 (d, 1H, J=7.0 Hz), 7.36 (s, 1H), 7.28 (s, 1H), 7.16 (dd, 1H, J=8.0 and 4.5 Hz), 6.15 (d, 1H, 7.0 Hz), 4.29 (t, 2H, J=7.0 Hz), 3.39 (t, 2H, J=7.0 Hz) and 2.06 (s, 3H) ppm.

EXAMPLE 13

3-chloro-5-{[2-oxo-1-(1H-pyrazolo[3,4-b]pyridin-3-ylmethyl)-4-(trifluoromethyl)-1,2-dihydropyridin-3-yl]oxy}benzonitrile (13-2)

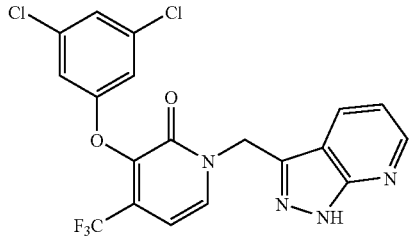 [SMILES: O=c1c(Oc2cc(Cl)cc(Cl)c2)c(C(F)(F)F)ccn1Cc1n[nH]c2ncccc12]

Step 1: tert-butyl 3-{[3-(3-chloro-5-cyanophenoxy)-2-oxo-4-(trifluoromethyl)pyridin-1(2H)-yl]methyl}-1H-pyrazolo[3,4-b]pyridine-1-carboxylate 13-1

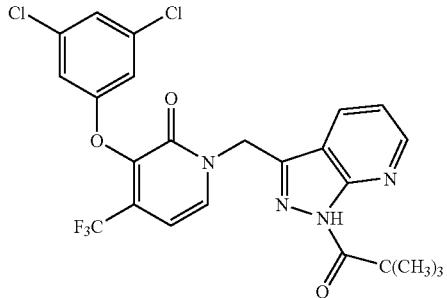 [SMILES: CC(C)(C)C(=O)n1nc(Cn2ccc(C(F)(F)F)c(Oc3cc(Cl)cc(Cl)c3)c2=O)c2cccnc21]

To a flask charged with 3-chloro-5-{[2-oxo-4-(trifluoromethyl)-1,2-dihydropyridin-3-yl]oxy}benzonitrile (3C, 2.03 g, 6.45 mmol) and potassium carbonate (0.891 g, 6.45 mmol) was added dimethylformamide (20 mL). To this under $N_2$ was added tert-butyl 3-(bromomethyl)-1H-pyrazolo[3,4-b]pyridine-1-carboxylate (2.01 g, 6.45 mmol) as a solution in dimethylformamide (10 mL). This was allowed to stir at room temperature for 16 hours. After this time the reaction mixture was diluted with water (50 mL) and the mixture was extracted with ethyl acetate (2×100 mL). The combined organic fractions were washed with brine (3×100 mL), dried (MgSO$_4$), filtered and the solvent was evaporated under reduced pressure. The resulting residue was purified by column chromatography on a pre-packed silica gel Redi Sep 120 gram column, eluting with 0-5% methanol in $CH_2Cl_2$ to give a solid. This was suspended in methanol (100 mL) and filtered to recover the title compound as a solid. $^1$H NMR (DMSO-$d_6$) δ 8.71 (d, J=4.4 Hz, 1H), 8.23 (d, J=8.0 Hz, 1H), 8.11 (d, J=7.1 Hz, 1H), 7.74-7.70 (m, 1H), 7.56-7.52 (m, 1H), 7.50-7.45 (m, 1H), 7.44-7.38 (m, 1H), 6.70 (d, J=7.1 Hz, 1H), 5.59 (s, 2H), 1.62 (s, 9H). LRMS (M+1)=545.8.

As an alternative to the chromatographic procedure above, the crude product can be purified by chromatography eluting with 0-100% EtOAc in heptane.

Step 2: 3-chloro-5-{[2-oxo-1-(1H-pyrazolo[3,4-b]pyridin-3-ylmethyl)-4-(trifluoromethyl)-1,2-dihydropyridin-3-yl]oxy}benzonitrile 13-2

To a round bottom flask charged with tert-butyl 3-{[3-(3-chloro-5-cyanophenoxy)-2-oxo-4-(trifluoromethyl)pyridin-1(2H)-yl]methyl}-1H-pyrazolo[3,4-b]pyridine-1-carboxylate (0.940 g, 1.72 mmol) was added TFA (50 mL). After 30 minutes, the reaction mixture was concentrated under reduced pressure. The residue was dissolved in hot acetonitrile (500 mL), hot filtered and allowed to cool to room temperature. After 1 day, the crystallized solids were filtered to yield the title compound as a white solid. $^1$H NMR (DMSO-$d_6$) δ 13.65 (s, 1H), 8.52 (d, J=4.5 Hz, 1H), 8.15 (d, J=8.1 Hz, 1H), 8.05 (d, J=7.2 Hz, 1H), 7.76-7.73 (m, 1H), 7.58-7.54 (m, 1H), 7.51-7.48 (m, 1H), 7.18 (dd, J=8.1 Hz, J=4.5 Hz, 1H), 6.63 (d, J=7.3 Hz, 1H), 5.53 (s, 2H). HRMS (M+1)= 446.0626.

As an alternative the residue from the concentrated reaction mixture can be isolated by dissolution in EtOAC and treatment with NaOH (1M) until pH 12. The organic extract can then be washed sequentially with saturated NaHCO$_3$ and brine and dried with MgSO$_4$. The solvent can then be evaporated in vacuo and the residue recrystallized from acetonitrile to afford the title compound.

EXAMPLE 14

N-(2-chlorobenzyl)-2-[3-(3-chloro-5-cyanophenoxy)-2-oxo-4-(trifluoromethyl)pyridin-1(2H)-yl]-N-methylacetamide (14)

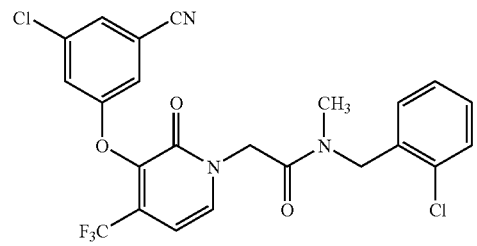 [SMILES: CN(Cc1ccccc1Cl)C(=O)Cn1ccc(C(F)(F)F)c(Oc2cc(Cl)cc(C#N)c2)c1=O]

To a flask charged with 3-chloro-5-{[2-oxo-4-(trifluoromethyl)-1,2-dihydropyridin-3-yl]oxy}benzonitrile (3C, 0.020 g, 0.064 mmol) and potassium carbonate (0.0088 g, 0.064 mmol) was added 2-chloro-N-(2-chlorobenzyl)-N-methylacetamide in dimethylformamide (0.75 mL). The reaction mixture was allowed to stir at room temperature. After 1.5 hours, the reaction mixture was filtered and the filtrate was purified by preparative HPLC Phenomenex Luna C18 100A 10μ, eluting with 30-95% MeCN/H₂O+0.1% TFA. and lyophilized to yield the title compound. ¹H NMR (DMSO-d₆) δ 7.90-7.84 (m, 1H), 7.76-7.74 (m, 1H), 7.54-7.43 (m, 3H), 7.42-7.32 (m, 1H), 7.31-7.26 (m, 2H), 7.23-7.19 (m, 1H), 6.68-6.62 (m, 1H), 5.09 (s, 1.35H), 4.80 (s, 0.65H), 4.72 (s, 0.65H), 4.59 (s, 1.35H), 3.06 (s, 2H), 2.82 (s, 1H). HRMS (M+1)=510.0591.

EXAMPLE 15

N-[4-(aminosulfonyl)-2-chlorophenyl]-2-[3-(3-chloro-5-cyanophenoxy)-2-oxo-4-(trifluoromethyl)pyridin-1(2H)-yl]acetamide (15)

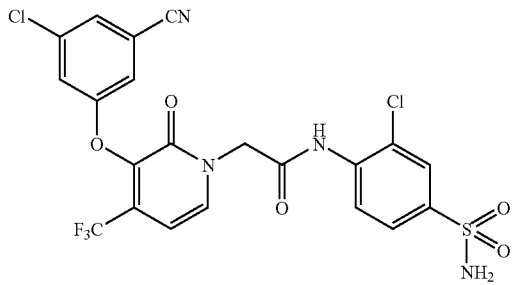 [SMILES: N#Cc1cc(Cl)cc(Oc2c(C(F)(F)F)ccn(CC(=O)Nc3ccc(S(N)(=O)=O)cc3Cl)c2=O)c1]

To 3-chloro-5-{[2-oxo-4-(trifluoromethyl)-1,2-dihydropyridin-3-yl]oxy}benzonitrile (3C, 0.050 g, 0.159 mmol) and potassium carbonate (0.022 g, 0.159 mmol) suspended in dimethylformamide (1 mL) was added N-[4-(aminosulfonyl)-2-chlorophenyl]-2-bromoacetamide (0.052 g, 0.149 mmol) as a solution in dimethylformamide (1 mL). The reaction mixture was allowed to stir at room temperature. After 16 hours, the reaction mixture was diluted with ethyl acetate (20 mL), washed with water (3×10 mL), dried (MgSO₄), filtered and the solvent was evaporated under reduced pressure. The resulting residue was purified by column chromatography on a pre-packed silica gel Redi Sep 12 gram column, eluting with 0-5% methanol in CH₂Cl₂ to yield the title compound. ¹H NMR (DMSO-d₆) δ 10.23 (s, 1H), 8.05-7.96 (m, 2H), 7.89 (d, J=2.1 Hz, 1H), 7.76-7.72 (m, 2H), 7.55-7.53 (m, 1H), 7.52-7.50 (m, 1H), 7.45 (s, 2H), 6.68 (d, 0.1=7.1 Hz, 1H), 5.02 (s, 2H). HRMS (M+1)=560.998.

EXAMPLE 16

N-[4-(aminosulfonyl)-2-chlorophenyl]-2-[3-(3-bromo-5-chlorophenoxy)-2-oxo-4-(trifluoromethyl)pyridin-1(2H)-yl]acetamide (16)

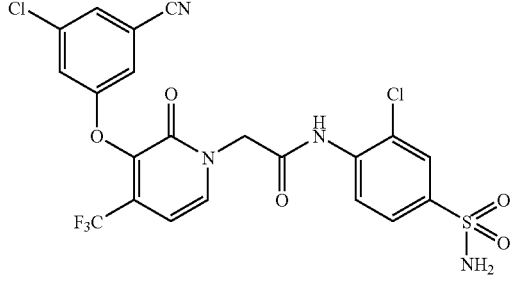 [SMILES: N#Cc1cc(Cl)cc(Oc2c(C(F)(F)F)ccn(CC(=O)Nc3ccc(S(N)(=O)=O)cc3Cl)c2=O)c1]

To 3-(3-bromo-5-chlorophenoxy)-4-(trifluoromethyl)pyridin-2(1H)-one (3B, 0.050 g, 0.136 mmol) and potassium carbonate (0.019 g, 0.136 mmol) suspended in dimethylformamide (1 mL) was added N-[4-(aminosulfonyl)-2-chlorophenyl]-2-bromoacetamide (0.046 g, 0.136 mmol) as a solution in dimethylformamide (1 mL). The reaction mixture was allowed to stir at room temperature. After 16 hours, the reaction mixture was diluted with ethyl acetate (20 mL), washed with water (3×10 mL), dried (MgSO₄), filtered and the solvent was evaporated under reduced pressure. The resulting residue was purified by column chromatography on a pre-packed silica gel Redi Sep 12 gram column, eluting with 0-5% methanol in CH₂Cl₂ to yield the title compound. ¹H NMR (DMSO-d₆) δ 10.23 (s, 1H), 8.0 (d, J=8.6 Hz, 1H), 7.96 (d, J=7.2 Hz, 1H), 7.90 (d, J=2.1 Hz, 1H), 7.75 (dd, J=8.6 Hz, J=2.1 Hz, 1H), 7.48-7.44 (m, 2H), 7.44-7.42 (m, 1H), 7.19-7.17 (m, 1H), 7.12-7.10 (m, 1H), 6.66 (d, J=7.2 Hz, 1H), 5.02 (s, 2H). HRMS (M+1)=613.913.

EXAMPLE 17

3-{[1-[(6-Amino-1H-pyrrolo[2,3-b]pyridin-3-yl)methyl]-2-oxo-4-(trifluoromethyl)-1,2-dihydropyridin-3-yl]oxy}-5-chlorobenzonitrile, trifluoroacetate salt (17-2)

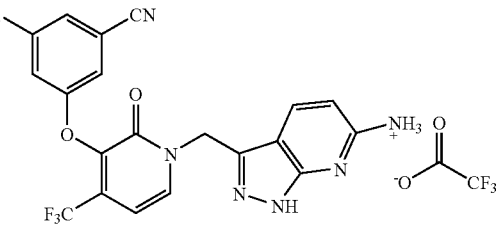

Step 1: 3-chloro-5-{[1-({1-(4-methoxybenzyl)-6-[(4-methoxybenzyl)amino]-1H-pyrazolo[3,4-b]pyridin-3-yl}methyl)-2-oxo-4-(trifluoromethyl)-1,2-dihydropyridin-3-yl]oxy}benzonitrile 17-1

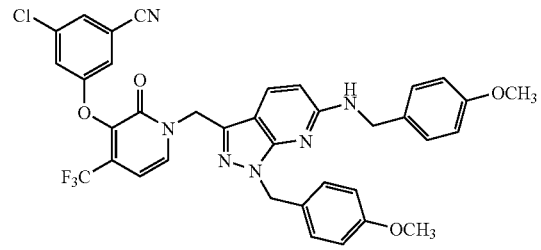 [SMILES: COc1ccc(CNc2ccc3c(Cn4ccc(C(F)(F)F)c(Oc5cc(Cl)cc(C#N)c5)c4=O)nn(Cc4ccc(OC)cc4)c3n2)cc1]

To 3-chloro-5-{[2-oxo-4-(trifluoromethyl)-1,2-dihydropyridin-3-yl]oxy}benzonitrile (3C, 0.150 g, 0.477 mmol) and potassium carbonate (0.066 g, 0.477 mmol) suspended in dimethylformamide (1 mL) was added 3-(chloromethyl)-N,1-bis(4-methoxybenzyl)-1H-pyrazolo[3,4-b]pyridin-6-amine (0.202 g, 0.477 mmol) as a solution in dimethyl formamide (1 mL). The reaction mixture was allowed to stir at room temperature. After 16 hours, the reaction mixture was diluted with ethyl acetate (50 mL), washed with brine (3×25 mL), dried (MgSO₄), filtered and the solvent was evaporated under reduced pressure. The resulting residue was adsorbed onto silica gel and purified by column chromatography on a pre-packed silica gel Redi Sep 40 gram column, eluting with 0-5% methanol in CH₂Cl₂ to afford the title compound. ¹H NMR (DMSO-d₆) δ 7.91 (d, J=7.0 Hz, 1H), 7.76-7.74 (m, 1H), 7.72-7.68 (m, 1H), 7.58-7.56 (m, 1H), 7.54 (d, J=8.6 Hz, 1H), 7.49-7.47 (m, 1H), 7.26 (d, J=8.6 Hz, 2H), 7.13 (d, J=8.6 Hz, 2H), 6.83 (d, J=8.6 Hz, 2H), 6.76 (d, J=8.6 Hz, 2H), 6.59 (d, J=7.2 Hz, 1H), 6.40 (d, J=8.9 Hz, 1H), 5.30 (s, 2H), 5.28 (s, 2H), 4.50-4.46 (m, 2H), 3.71 (s, 3H), 3.69 (s, 3H). LRMS (M+1)=700.6.

Step 2: 3-{[3-(3-chloro-5-cyanophenoxy)-2-oxo-4-(trifluoromethyl)pyridin-1(2H)-yl]methyl}-1H-pyrazolo[3,4-b]pyridin-6-aminium trifluoroacetate 17-2

3-chloro-5-{[1-({1-(4-methoxybenzyl)-6-[(4-methoxybenzyl)amino]-1H-pyrazolo[3,4-b]pyridin-3-yl}methyl)-2-oxo-4-(trifluoromethyl)-1,2-dihydropyridin-3-yl]oxy}benzonitrile (0.185 g, 0.264 mmol) was dissolved in TFA (5 mL) and placed in an oil bath at 75° C. After 2 hours, the reaction mixture was concentrated under reduced pressure and purified by preparative HPLC eluting with 30-95% MeCN/H$_2$O+0.1% TFA to afford the title compound as a solid. $^1$H NMR (DMSO-d$_6$, with NH$_4$OH) δ 7.94 (d, J=7.3 Hz, 1H), 7.77-7.74 (m, 1H), 7.62-7.56 (m, 2H), 7.50-7.46 (m, 1H), 6.60 (d, J=7.3 Hz, 1H), 6.38-6.33 (m, 2H), 6.30 (d, J=8.8 Hz, 1H), 5.32 (s, 2H). HRMS (M+1)=461.0729.

EXAMPLE 18

5-{[2-oxo-1-(1H-pyrazolo[3,4-b]pyridine-3-ylmethyl)-4-(trifluoromethyl)-1,2-dihydropyridin-3-yl]oxy}isophthalonitrile (18-4)

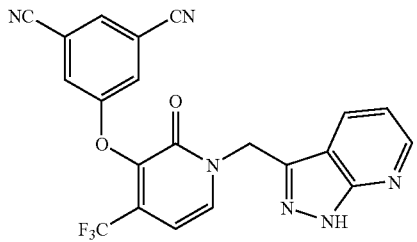

Step 1: 2-chloro-3-(3,5-dibromophenoxy)-4-(trifluoromethyl)pyridine 18-1

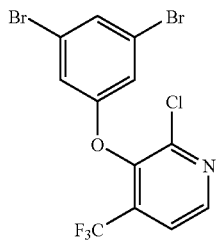 [SMILES: FC(F)(F)c1ccnc(Cl)c1Oc1cc(Br)cc(Br)c1]

To a round bottom flask charged with 3,5-dibromophenol (1.16 g, 4.61 mmol) and potassium carbonate (1.27 g, 9.22 mmol) was added N-methylpyrrolidinone (10 mL). To this suspension under N$_2$ was added 2-chloro-3-fluoro-4-(trifluoromethyl)pyridine (0.920 g, 4.61 mmol) and the reaction mixture was placed in an oil bath at 120° C. After 30 minutes, the reaction mixture was allowed to cool to room temperature. Water (50 mL) was added and the mixture was extracted with ethyl acetate (2×50 mL). The combined organic extracts were washed with brine (3×50 mL), dried (MgSO$_4$), filtered and the solvent was evaporated under reduced pressure. The resulting residue was purified by column chromatography on a pre-packed silica gel Redi Sep 120 gram column, eluting with 0-75% CH$_2$Cl$_2$ in hexanes to afford the title compound. $^1$H NMR (CDCl$_3$) δ 8.53 (d, J=5.0 Hz, 1H), 7.62 (d, J=5.0 Hz, 1H), 7.44-7.42 (m, 1H), 6.92-6.88 (m, 2H). LRMS (M+1)= 431.5.

Step 2: 3-(3,5-dibromophenoxy)-4-(trifluoromethyl)pyridin-2(1H)-one 18-2

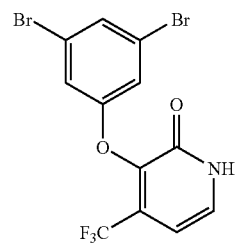 [SMILES: O=c1[nH]ccc(C(F)(F)F)c1Oc1cc(Br)cc(Br)c1]

2-chloro-3-(3,5-dibromophenoxy)-4-(trifluoromethyl)-1,2-dihydropyridine (1.64 g, 3.80 mmol) and potassium hydroxide (0.640 g, 11.4 mmol) were dissolved in tert-butanol in a round bottom flask and placed in an oil bath at 75° C. under N$_2$. After 16 hours, the reaction mixture was allowed to cool to room temperature and quenched with saturated aqueous ammonium chloride (25 mL). This mixture was diluted with water (25 mL) and extracted with ethyl acetate (2×50 mL). The combined organic extracts were washed with brine (2×50 mL), dried (MgSO$_4$), filtered and the solvent was evaporated under reduced pressure to give the title compound as a white solid. $^1$H NMR (DMSO-d$_6$) δ 12.68 (s, 1H), 7.58 (d, J=6.8 Hz, 1H), 7.54-7.52 (m, 1H), 7.24-7.22 (m, 2H), 6.47 (d, J=Hz, 1H). LRMS (M+1)=413.5.

Step 3: 5-{[2-oxo-4-(trifluoromethyl)-1,2-dihydropyridin-3-yl]oxy}isophthalonitrile 18-3

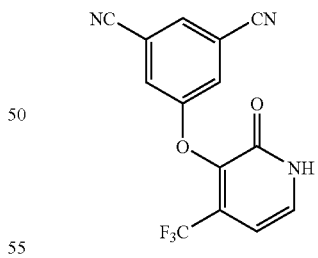

To a high pressure vessel charged with 3-(3,5-dibromophenoxy)-4-(trifluoromethyl)pyridin-2(1H)-one (0.200 g, 0.484 mmol) and copper(I) cyanide (0.434 g, 4.84 mmol) was added N-methylpyrrolidinone (2 mL). The vessel was sealed and placed in an oil bath heated to 175° C. After 90 minutes, the reaction mixture was allowed to cool to room temperature. Water (25 mL) and ethyl acetate (50 mL) were added to the reaction mixture. This mixture was filtered through diatomaceous earth and the filtrate layers were separated. The aqueous layer was extracted with ethyl acetate (50 mL). The combined organic extracts were washed with brine (2×50 mL), dried (MgSO₄), filtered and the solvent was evaporated under reduced pressure. The resulting residue was adsorbed onto silica gel and purified by column chromatography on a pre-packed silica gel Redi Sep 40 gram column, eluting with 0-5% methanol in CH$_2$Cl$_2$ to afford the title compound. $^1$H NMR (DMSO-d$_6$) δ 12.72 (s, 1H), 8.16-8.14 (m, 1H), 8.02-7.98 (m, 2H), 7.61 (d, J=7.0 Hz, 1H), 6.50 (d, J=6.9 Hz, 1H). LRMS (M+1)=305.9.

Step 4: 5-{[2-oxo-1-(1H-pyrazolo[3,4-b]pyridine-3-ylmethyl)-4-(trifluoromethyl)-1,2-dihydropyridin-3-yl]oxy}isophthalonitrile 18-4

5-{[2-oxo-4-(trifluoromethyl)-1,2-dihydropyridin-3-yl]oxy}isophthalonitrile (0.076 g, 0.249 mmol), tert-butyl 3-(bromomethyl)-1H-pyrazolo[3,4-b]pyridine-1-carboxylate (0.078 g, 0.249 mmol) and potassium carbonate (0.034 g, 0.249 mmol) were combined and diluted with dimethylformamide (1 mL) and stirred at room temperature. After 16 hours, water (10 mL) was added and the mixture was extracted with ethyl acetate (2×25 mL). The combined organic extracts were washed with brine (3×25 mL), dried (MgSO₄), filtered and the solvent was evaporated under reduced pressure. The resulting solid was dissolved in TFA. After 30 minutes, the solution was concentrated. The resulting solid was suspended in methanol and filtered to afford the title compound as a solid. $^1$H NMR (DMSO-d$_6$) δ 8.52 (d, J=4.6 Hz, 1H), 8.17-8.17 (m, 1H), 8.15 (d, J=8.2 Hz, 1H), 8.06 (d, J=7.1 Hz, 1H), 7.98 (m, 2H), 7.18 (dd, J=8.2 Hz, J=4.7 Hz, 1H), 6.65 (d, J=7.3 Hz, 1H), 5.52 (s, 2H). HRMS (M+1)=437.0981.

EXAMPLE 19

3-(3,5-dichlorophenoxy)-1-(1H-pyrazolo[3,4-b]pyridin-3-ylmethyl)-4-(trifluoromethyl)pyridin-2(1H)-one (19-4)

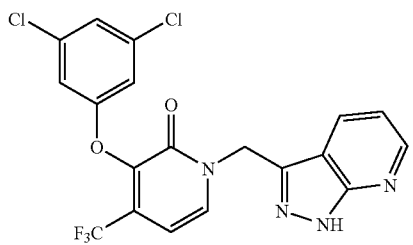 [SMILES: O=c1c(Oc2cc(Cl)cc(Cl)c2)c(C(F)(F)F)ccn1Cc1n[nH]c2ncccc12]

Step 1: 2-chloro-3-(3,5-dichlorophenoxy)-4-(trifluoromethyl)pyridine 19-1

To a round bottom flask charged with 3,5-dichlorophenol (1.23 g, 7.52 mmol) and potassium carbonate (1.04 g, 7.52 mmol) was added N-methylpyrrolidinone (5 mL). To this suspension under N2 was added 2-chloro-3-fluoro-4-(trifluoromethyl)pyridine (1.50 g, 7.52 mmol) and the reaction mixture was placed in an oil bath at 120° C. After 60 minutes, the reaction mixture was allowed to cool to room temperature, water (20 mL) was added and the mixture was extracted with ethyl acetate (2×25 mL). The combined organic extracts were washed with brine (3×25 mL), dried (MgSO₄), filtered and the solvent was evaporated under reduced pressure. The resulting residue was purified by column chromatography on a pre-packed silica gel Redi Sep 80 gram column, eluting with 0-75% CH$_2$Cl$_2$ in hexanes to afford the title compound. $^1$H NMR (DMSO-d$_6$) δ 8.52 (d, J=4.5 Hz, 1H), 7.60 (d, J=4.6 Hz, 1H), 7.14-7.10 (m, 1H), 6.72-6.68 (m, 2H). HRMS (M+1)= 341.9465.

Step 2: 3-(3,5-dichlorophenoxy)-4-(trifluoromethyl)pyridin-2(1H)-one 19-2

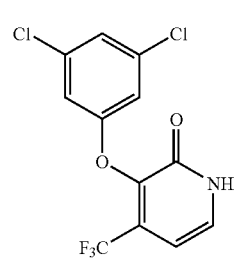

To 2-chloro-3-(3,5-dichlorophenoxy)-4-(trifluoromethyl)pyridine (2.10 g, 6.10 mmol) in tert-butanol (25 mL) was added potassium hydroxide (1.03 g, 18.4 mmol). The reaction mixture was placed in an oil bath and heated at 75° C. After 48 hours, the reaction mixture was allowed to cool to room temperature and was quenched with saturated aqueous ammonium chloride (25 mL) and diluted with water (25 mL). The mixture was extracted with ethyl acetate (2×50 mL). The combined organic extracts were washed with water (2×50 mL) and the solvent was evaporated under reduced pressure to yield a solid. This was adsorbed onto silica and purified by column chromatography on a pre-packed silica gel Redi Sep 40 gram column, eluting with 0-5% methanol in CH$_2$Cl$_2$ to afford the title compound. $^1$H NMR (DMSO-d$_6$) δ 12.69 (s, 1H), 7.58 (d, J=6.8 Hz, 1H), 7.32-7.30 (m, 1H), 7.10-7.08 (m, 2H), 6.48 (d, J=6.8 Hz, 1H). HRMS (M+1)=323.9800.

Step 3: tert-butyl 3-{[3-(3,5-dichlorophenoxy)-2-oxo-4-(trifluoromethyl)pyridin-1(2H)-yl]methyl}-1H-pyrazolo[3,4-b]pyridine-1-carboxylate 19-3

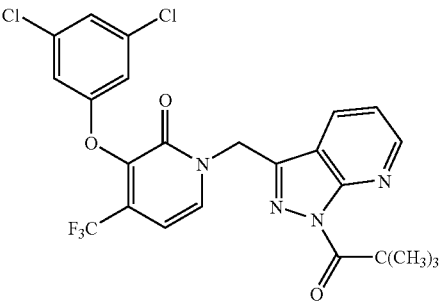 [SMILES: CC(C)(C)C(=O)n1nc(Cn2ccc(C(F)(F)F)c(Oc3cc(Cl)cc(Cl)c3)c2=O)c2cccnc21]

To a flask charged with 3-(3,5-dichlorophenoxy)-4-(trifluoromethyl)pyridin-2(1H)-one (0.500 g, 1.54 mmol) and potassium carbonate (0.213 g, 1.54 mmol) was added dimethylformamide (5 mL). To this under N$_2$ was added tert-butyl 3-(bromomethyl)-1H-pyrazolo[3,4-b]pyridine-1-carboxylate (0.482 g, 1.54 mmol) as a solution in dimethylformamide (2 mL). This was allowed to stir at room temperature. After 16 hours, the reaction mixture was diluted with ethyl acetate (100 mL), washed with brine (3×50 mL), dried (MgSO₄), filtered and the solvent was evaporated under reduced pressure. The residue was purified by column chromatography on a pre-packed silica gel Redi Sep 40 gram column, eluting with 0-50% ethyl acetate in hexanes to afford the title compound. ¹H NMR (DMSO-d₆) δ 8.72 (d, J=4.5 Hz, 1H), 8.26-8.22 (m, 1H), 8.11 (d, J=7.2 Hz, 1H), 7.43 (dd, J=8.0 Hz, J=4.6 Hz, 1H), 7.30-7.28 (m, 1H), 7.05-7.02 (m, 2H), 6.70 (d, J=7.2 Hz, 1H), 5.60 (s, 2H), 1.62 (s, 9H). HRMS (M+1)=555.0826.

Step 4: 3-(3,5-dichlorophenoxy)-1-(1H-pyrazolo[3,4-b]pyridin-3-ylmethyl)-4-(trifluoromethyl)pyridin-2(1H)-one 19-4

To tert-butyl 3-{[3-(3,5-dichlorophenoxy)-2-oxo-4-(trifluoromethyl)pyridin-1(2H)-yl]methyl}-1H-pyrazolo[3,4-b]pyridine-1-carboxylate (0.625 g, 1.13 mmol) in a flask was added TFA (10 mL). This solution under an atmosphere of N₂ was placed in an oil bath at 75° C. After 4 hours, the reaction mixture was concentrated under reduced pressure, diluted with ethyl acetate (100 mL) and washed with 50% aqueous sodium carbonate (50 mL). The aqueous layer was back extracted with ethyl acetate (100 mL) and the combined organic extracts were dried (MgSO₄), filtered and the solvent evaporated under reduced pressure. The resulting solid was adsorbed onto silica gel and purified by column chromatography on a pre-packed silica gel Redi Sep 40 gram column, eluting with 0-5% methanol in CH₂Cl₂ to afford the title compound. ¹H NMR (DMSO-d₆) δ 13.65 (s, 1H), 8.54-8.52 (m, 1H), 8.16 (d, J=8.0 Hz, 1H), 8.04 (d, J=7.3 Hz, 1H), 7.32-7.30 (m, 1H), 7.18 (dd, J=8.0 Hz, J=4.4 Hz, 1H), 7.06-7.04 (m, 2H), 6.63 (d, J=7.3 Hz, 1H), 5.54 (s, 2H). HRMS (M+1)=455.0289.

EXAMPLE 20

1-[(6-Amino-1H-pyrrolo[2,3-b]pyridin-3-yl)methyl]-3-(3,5-dichlorophenoxy)-4-(trifluoromethyl)pyridin-2(1H)-one, hydrochloride salt (20-3)

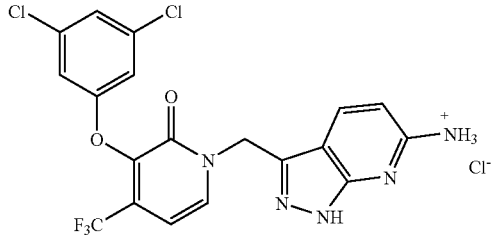 [SMILES: Nc1ccc2c(Cn3ccc(C(F)(F)F)c(Oc4cc(Cl)cc(Cl)c4)c3=O)n[nH]c2n1 ; [Cl-]]

Step 1: 3-(3,5-dichlorophenoxy)-1-({1-(4-methoxybenzyl)-6-[(4-methoxybenzyl)amino]-1H-pyrazolo[3,4-b]pyridine-3-yl}methyl)-4-(trifluoromethyl)pyridine-2(1H)-one 20-1

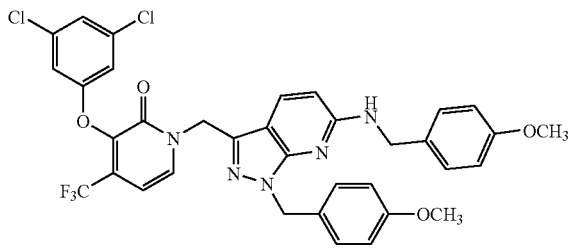 [SMILES: COc1ccc(CNc2ccc3c(Cn4ccc(C(F)(F)F)c(Oc5cc(Cl)cc(Cl)c5)c4=O)nn(Cc4ccc(OC)cc4)c3n2)cc1]

To 3-(3,5-dichlorophenoxy)-4-(trifluoromethyl)pyridine-2(1H)-one (0.400 g, 1.23 mmol) and potassium carbonate (0.171 g, 1.23 mmol) suspended in dimethylformamide (5 mL) was added 3-(chloromethyl)-N,1-bis(4-methoxybenzyl)-1H-pyrazolo[3,4-b]pyridine-6-amine (0.522 g, 1.23 mmol) as a solution in dimethylformamide (2 mL). The reaction mixture was allowed to stir at room temperature. After 16 hours, the reaction mixture was diluted with water (50 mL) and extracted with ethyl acetate (2×100 mL). The combined organic extracts were washed with brine (3×100 mL), dried (MgSO₄), filtered and the solvent was evaporated under reduced pressure to afford the title compound as a solid. ¹H NMR (DMSO-d₆) δ 7.90 (d, J=7.3 Hz, 1H), 7.75-7.67 (m, 1H), 7.52 (d, J=8.8 Hz, 1H), 7.34-7.30 (m, 1H), 7.27 (d, J=8.4 Hz, 2H), 7.13 (d, J=8.6 Hz, 2H), 7.07-7.03 (m, 2H), 6.83 (d, J=8.6 Hz, 2H), 6.77 (d, J=8.6 Hz, 2H), 6.59 (d, J=7.3 Hz, 1H), 6.40 (d, J=8.8 Hz, 1H), 5.31 (s, 2H), 5.29 (s, 2H), 4.48 (d, J=4.3 Hz, 2H), 3.71 (s, 3H), 3.69 (s, 3H). HRMS (M+1)=710.1557.

Step 2: 1-[(6-amino-1H-pyrazolo[3,4-b]pyridin-3-yl)methyl]-3-(3,5-dichlorophenoxy)-4-(trifluoromethyl)pyridin-2(1H)-one 20-2

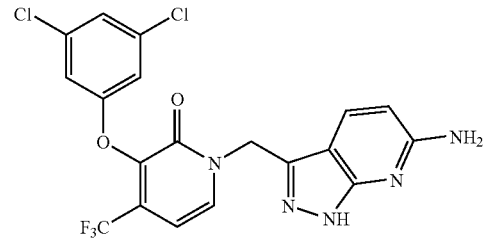 [SMILES: Nc1ccc2c(Cn3ccc(C(F)(F)F)c(Oc4cc(Cl)cc(Cl)c4)c3=O)n[nH]c2n1]

3-(3,5-dichlorophenoxy)-1-({1-(4-methoxybenzyl)-6-[(4-methoxybenzyl)amino]-1H-pyrazolo[3,4-b]pyridine-3-yl}methyl)-4-(trifluoromethyl)pyridine-2(1H)-one (0.900 g, 12.7 mmol) dissolved in TFA (10 mL) was placed in an oil bath at 75° C. After 4 hours, the reaction mixture was diluted with ethyl acetate (100 mL), washed with 50% aqueous sodium carbonate (50 mL). The aqueous was back extracted with ethyl acetate (100 mL) and the combined organic extracts were dried (MgSO₄), filtered and the solvent was evaporated under reduced pressure. The resulting solid was adsorbed onto silica gel and purified by column chromatography on a pre-packed silica gel Redi Sep 40 gram column, eluting with 0-5% methanol in CH₂Cl₂ to afford the title compound. ¹H NMR (DMSO-d₆) δ 12.60 (s, 1H), 8.00-7.90 (m, 1H), 7.65-7.50 (m, 1H), 7.40-7.30 (m, 1H), 7.12-7.00 (m, 2H), 6.65-6.55 (m, 1H), 6.42-6.25 (m, 3H), 5.40-5.30 (s, 2H). LRMS (M+1)=469.77.

Step 3: 3-{[3-(3,5-dichlorophenoxy)-2-oxo-4-(trifluoromethyl)pyridin-1(2H)-yl]methyl}-1H-pyrazolo[3,4-b]pyridin-6-aminium chloride 20-3

1-[(6-amino-1H-pyrazolo[3,4-b]pyridin-3-yl)methyl]-3-(3,5-dichlorophenoxy)-4-(trifluoromethyl)pyridin-2(1H)-one (0.495 g, 1.05 mmol) was dissolved in a mixture of 20% methanol in CH₂Cl₂ (25 mL) and 4M HCl in dioxane (0.077 g, 2.10 mmol) was added. After 15 minutes, the reaction mixture was concentrated under reduced pressure and placed under vacuum for 4 hours to afford the title compound as a solid. ¹H NMR (DMSO-d₆ with NH₄OH) δ 7.93 (d, J=7.1 Hz, 1H), 7.58 (d, J=8.7 Hz, 1H), 7.13-7.11 (m, 1H), 7.06-7.04 (m, 2H), 6.59 (d, J=7.2 Hz, 1H), 6.37-6.34 (m, 2H), 6.31 (d, J=8.7 Hz, 1H), 5.34 (s, 2H). HRMS (M+1)=470.0392.

EXAMPLE 21

3-chloro-5-{[4-chloro-2-oxo-1-(1H-pyrazolo[3,4-b]pyridin-3-ylmethyl)-1,2-dihydropyridin-3-yl]oxy}benzonitrile (21-8)

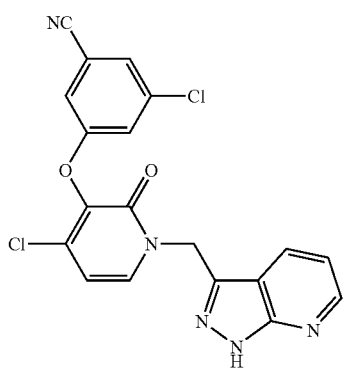

Step 1: 2-bromo-4-chloro-3-fluoropyridine 21-1

To a solution of 2,2,6,6-tetramethylpiperidine (25 g, 190 mmol) in hexanes (100 mL) cooled over dry ice acetone bath for 5 minutes was added 1.6M n-butyl lithium in hexanes (121 mL, 194 mmol) over 5 minutes. After the addition was complete, the reaction mixture was placed in an ice bath and the mixture was allowed to stir at 0° C. for 20 minutes as a white solid formed. The suspension was re-cooled over dry ice/acetone bath for 5 minutes and then treated with a solution of 4-chloro-3-fluoropyridine (25 g, 190 mmol) in hexanes (50 mL) over 5 minutes and this mixture was stirred over dry ice/acetone bath for additional 10 minutes. After this time, this mixture was treated with bromine (30.4 mL, 190 mmol) and stirred over dry ice/acetone bath for 15 minutes. After this time, the reaction mixture was stirred for 30 minutes at 0° C. and then allowed to warm to room temperature. The reaction mixture was re-cooled over wet ice bath and quenched with water (200 mL) and extracted with ether (3×300 mL). The combined organic extracts were washed with water, dried (MgSO$_4$), and the solvent removed in vacuo. The residue was purified by chromatography using 330 g silica gel cartridge and eluting with a gradient of 20-100% CH$_2$Cl$_2$ in hexanes to provide the title compound. $^1$H NMR (CDCl$_3$) δ=8.13 (d, 1H, J=5.1 Hz) and 7.35 (dd, 1H, J=5 Hz) ppm.

Step 2: 4-chloro-3-fluoropyridine-2-carbonitrile 21-2

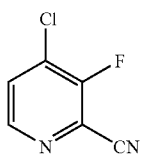

To a degassed solution of 2-bromo-4-chloro-3-fluoropyridine (7.3 g, 34.7 mmol) in DMF (50 mL) was added palladium tetrakistriphenylphosphine (4.01 g, 3.47 mmol) and zinc cyanide (4.07 g, 34.7 mmol) and heated to 100° C. for 20 minutes. After this time, more palladium tetrakis triphenylphosphine (4.01 g, 3.47 mmol) was added and heated to 100° C. for 90 minutes. The mixture was allowed to cool to room temperature and treated with water (200 mL) and ether (400 mL). The resulting mixture was filtered to remove insoluble solids, the filtrate was partitioned, and the aqueous layer was extracted with ether (400 mL). The combined ether extracts were washed with water (200 mL), dried (MgSO$_4$), filtered, and the solvent removed in vacuo. This residue was purified by chromatography using silica gel column (330 g) eluting with a gradient of 10-100% CH$_2$Cl$_2$ in hexanes to provide the title compound. $^1$H NMR (CDCl$_3$) δ=8.45 (d, 1H, J=5 Hz) and 7.65 (dd, 1H, J=5 Hz) ppm.

Step 3: 3-(3-bromo-5-chlorophenoxy)-4-chloropyridine-2-carbonitrile 21-3

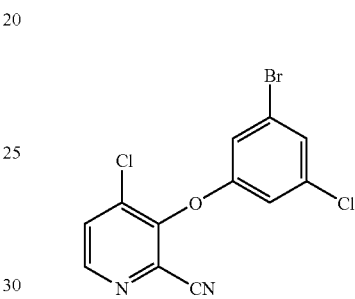

To a solution of 4-chloro-3-fluoropyridine-2-carbonitrile (2.18 g, 9.03 mmol) in DMF (10 mL) was added 3-bromo-5-chlorophenol (1.96 g, 9.48 mmol) and potassium carbonate (1.25 g, 9.03 mmol) and the mixture was heated to 55° C. for 10 minutes. The mixture was cooled to room temperature and partitioned between water (200 mL) and ethyl acetate (2×100 mL). The combined organic extracts were dried over MgSO$_4$, filtered, and the solvent evaporated in vacuo to provide the title compound. LRMS (M+1): 344.8

Step 4: 3-(3-bromo-5-chlorophenoxy)-4-chloropyridine-2-carboxylic acid 21-4

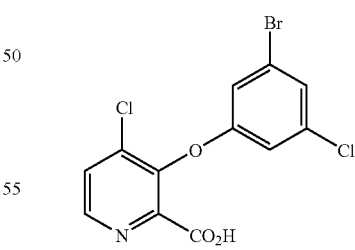

A suspension of 3-(3-bromo-5-chlorophenoxy)-4-chloropyridine-2-carbonitrile (3.20 g, 9.30 mmol) in concentrated aqueous hydrochloric acid (50 mL) in a pressure bottle was heated to 100° C. for 2 hours. After this time, the mixture was allowed to cool to room temperature. The resulting white solid was filtered and washed with water (20 mL) and then dried under high vacuum to provide the title compound. LRMS (M+1): 362.7.

Step 5: tert-butyl [3-(3-bromo-5-chlorophenoxy)-4-chloropyridin-2-yl]carbamate 21-5

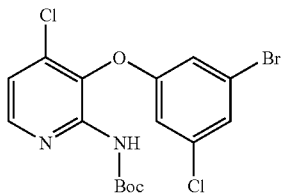 [SMILES: CC(C)(C)OC(=O)Nc1nccc(Cl)c1Oc1cc(Cl)cc(Br)c1]

3-(3-bromo-5-chlorophenoxy)-4-chloropyridine-2-carboxylic acid (1.29 g, 3.55 mmol) was suspended in toluene (10 mL) and the solvent evaporated in vacuo to azeotrope any residual water. This dried solid was dissolved in THF (10 mL) and cooled over an ice bath for 5 minutes. This solution was sequentially treated with triethylamine (719 ul, 7.11 mmol), pyridine (575 ul, 7.11 mmol), t-butanol (1.699 mL, 17.77 mmol) and lastly DPPA (1.151 mL, 5.33 mmol). This solution was allowed to stir at room temperature for 20 minutes and then heated to 65° C. for 60 minutes. This reaction mixture was allowed to cool to room temperature and then partitioned between ethyl acetate (2×100 mL) and saturated aqueous NaHCO$_3$ (100 mL). The combined extracts were dried over MgSO$_4$, filtered and the solvent removed in vacuo. The residue was purified by chromatography using silica gel (330 g) eluting with a gradient of 0-100% EtOAc in CH$_2$Cl$_2$ to give the title compound. LRMS (M+1): 334.6.

Step 6: 3-[(2-amino-4-chloropyridin-3-yl)oxy]-5-chlorobenzonitrile 21-6

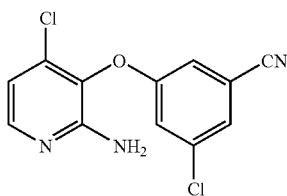 [SMILES: N#Cc1cc(Cl)cc(Oc2c(Cl)ccnc2N)c1]

To a degassed solution of tert-butyl [3-(3-bromo-5-chlorophenoxy)-4-chloropyridin-2-yl]carbamate (651 mg, 1.50 mmol) in NMP (7 mL) was added palladium tetrakistriphenylphosphine (260 mg, 0.225 mmol) and zinc cyanide (176 mg, 1.50 mmol) and heated to 100° C. for 20 minutes. After this time, the mixture was allowed to cool to room temperature and partitioned between water (20 mL) and ethyl acetate (2×50 mL). The combined organic extracts were washed with water (20 mL), dried over MgSO$_4$, filtered and the solvent removed in vacuo. This residue was dissolved in TFA for 10 minutes and then the solvent was removed in vacuo. This residue was partitioned between NaHCO$_3$ (50 mL) and ethyl acetate (2×50 mL). The combined extracts were dried over MgSO$_4$, filtered and the solvent removed in vacuo. This residue was purified by chromatography using silica gel column (120 g) and eluting with a gradient of 0-50% EtOAc in CH$_2$Cl$_2$ to provide the title compound. LRMS (M+1): 279.8.

Step 7: 3-chloro-5-[(4-chloro-2-hydroxypyridin-3-yl)oxy]benzonitrile 21-7

To a suspension of 3-[(2-amino-4-chloropyridin-3-yl)oxy]-5-chlorobenzonitrile (590 mg, 2.106 mmol) in 5% aqueous H$_2$SO$_4$ (20 mL) cooled over an ice bath for 5 minutes was added sodium nitrite (247 mg, 3.58 mmol) and stirred 5 minutes. This mixture was then heated to 100° C. for 5 minutes. The mixture was re-cooled over an ice bath and treated with additional sodium nitrite (124 mg, 1.79 mmol), stirred cold for another 5 minutes and then heated to 100° C. for 5 minutes. The reaction mixture was again cooled over an ice bath and the resulting white solid was filtered and washed with water (4×5 mL). This solid was dried under high vacuum to provide the title compound. LRMS (M+1): 280.7.

Step 8: 3-chloro-5-{[4-chloro-2-oxo-1-(1H-pyrazolo[3,4-b]pyridin-3-ylmethyl)-1,2-dihydropyridin-3-yl]oxy}benzonitrile 21-8

To a solution of 3-chloro-5-[(4-chloro-2-hydroxypyridin-3-yl)oxy]benzonitrile (150 mg, 0.534 mmol) in DMF (3 mL) was added tert-butyl 3-(bromomethyl)-1H-pyrazolo[3,4-b]pyridine-1-carboxylate (167 mg, 0.534 mmol) and potassium carbonate (73.8 mg, 0.534 mmol) and the mixture warmed to 55° C. for 60 minutes. After this time, the reaction mixture was purified by preparative HPLC using a Luna reverse phase column (10μ, C$_{18}$, 250×21.2 mm) and eluting with a gradient of 5-95% ACN/water (0.5% TFA). The desired fractions were combined and the solvent evaporated in vacuo. The residue was dissolved in TFA (10 mL) and allowed to stand at room temperature for 15 minutes and then the solvent was evaporated in vacuo to give a white solid. This solid was suspended in ACN (10 mL) and the solvent evaporated in vacuo to give the title compound. $^1$H NMR (DMSO-d$_6$) δ=13.64 (s, 1H), 8.52 (dd, 1H, J=1.6 and 4.5 Hz), 8.15 (dd, 1H, J=1.4 and 8.06 Hz), 7.90 (d, 1H, J=7.5 Hz), 7.73 (dd, 1H, J=1.7 and 1.4 Hz), 7.50 (dd, 1H, J=2.5 and 1.2 Hz), 7.41 (dd, 1H, J=3.2 and 1.9 Hz), 7.18 (dd, 1H, J=4.5 and 8.06 Hz), 6.61 (d, 1H, J=7.5 Hz) and 5.48 (s, 2H) ppm. HRMS (M+1): 412.0372.

EXAMPLE 22

3-({1-[(6-amino-1H-pyrazolo[3,4-b]pyridin-3-yl)methyl]-4-chloro-2-oxo-1,2-dihydropyridin-3-yl}oxy)-5-chlorobenzonitrile trifluoroacetate (22)

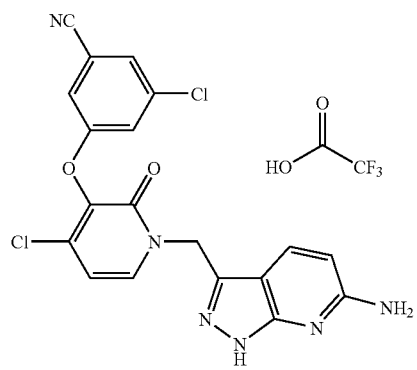

To a solution of 3-chloro-5-[(4-chloro-2-hydroxypyridin-3-yl)oxy]benzonitrile (100 mg, 0.356 mmol) in DMF (3 mL) was added 3-(chloromethyl)-N,1-bis(4-methoxybenzyl)-1H-pyrazolo[3,4-b]pyridin-6-amine (150 mg, 0.356 mmol) and potassium carbonate (49.2 mg, 0.356 mmol) and heated the mixture to 55° C. for 140 minutes. After this time, the reaction mixture was diluted with water (40 mL) and ethyl acetate (40 mL) and the resulting solid was filtered and washed with ethyl acetate. This residue was dissolved in TFA (20 mL) and heated to 75° C. for 20 minutes and then the solvent was evaporated in vacuo. The residue was suspended in ACN (7 mL) and the resulting white solid was filtered and washed with ACN (3 mL). This solid was dried under high vacuum to provide the title compound. $^1$H NMR (DMSO-$d_6$ with NH$_4$OH) δ=7.78 (d, 1H, J=7.5 Hz), 7.74 (dd, 1H, J=1.5 Hz), 7.59 (d, 1H, J=8.7 Hz), 7.52 (dd, 1H, J=1.3 and 2.4 Hz), 7.39 (dd, 1H, 1.0 and 2.2 Hz), 6.56 (d, 1H, J=7.4 Hz), 6.33 (br s, 2H), 6.30 (d, 1H, 8.7 Hz) and 5.28 (s, 2H) ppm. HRMS (M+1): 427.0486.

EXAMPLE 23

3-chloro-5-{[4,5-dichloro-2-oxo-1-(1H-pyrazolo[3,4-b]pyridin-3-ylmethyl)-1,2-dihydropyridin-3-yl]oxy}benzonitrile (23-2)

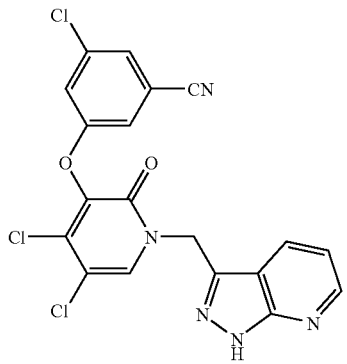 [SMILES: N#Cc1cc(Cl)cc(Oc2c(Cl)c(Cl)cn(Cc3n[nH]c4ncccc34)c2=O)c1]

Step 1: 3-chloro-5-[(4,5-dichloro-2-oxo-1,2-dihydropyridin-3-yl)oxy]benzonitrile 23-1

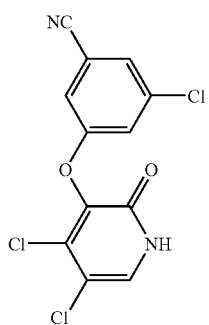

To a suspension of 3-chloro-5-[(4-chloro-2-hydroxypyridin-3-yl)oxy]benzonitrile (50 mg, 0.178 mmol) in acetic acid (1 mL) was added N-chlorosuccinimide (35.6 mg, 0.267 mmol) and the resulting mixture heated to 70° C. for 2 hours. This mixture was allowed to cool to room temperature and the resulting white solid was filtered and washed with methanol (1 mL) to provide the title compound. LRMS (M+1): 314.6.

Step 2: 3-chloro-5-{[4,5-dichloro-2-oxo-1-(1H-pyrazolo[3,4-b]pyridin-3-ylmethyl)-1,2-dihydropyridin-3-yl]oxy}benzonitrile 23-2

To a solution of 3-chloro-5-[(4,5-dichloro-2-oxo-1,2-dihydropyridin-3-yl)oxy]benzonitrile (49 mg, 0.155 mmol) in DMF (1 mL) was added tert-butyl 3-(bromomethyl)-1H-pyrazolo[3,4-b]pyridine-1-carboxylate (48.5 mg, 0.155 mmol) and potassium carbonate (21.46 mg, 0.155 mmol) and the mixture heated at 55° C. for 30 minutes. After this time, the reaction mixture was allowed to cool to room temperature and the mixture was filtered through a Gelma Acrodisc. The filtrate was purified on Gilson LC using a Luna reverse phase column (10µ, $C_{18}$, 250×21.2 mm) eluting with a gradient of 20-95% ACN/water (0.5% TFA). The desired fractions were combined and evaporated in vacuo. This residue was dissolved in TFA (3 mL) and allowed to stand at room temperature for 15 minutes and then the solvent was evaporated in vacuo to give a white solid. This solid was suspended in ACN (10 mL) and the solvent removed in vacuo to give the title compound. $^1$H NMR (DMSO-$d_6$) δ=8.52 (d, 1H, J=3.8 Hz), 8.41 (s, 1H), 8.19 (d, 1H, J=7.9 Hz), 7.74 (s, 1H), 7.60 (s, 1H), 7.55 (s, 1H), 7.19 (dd, 1H, J=4 and 8.9 Hz) and 5.49 (s, 2H) ppm. HRMS (M+1): 445.9991.

EXAMPLE 24

3-Chloro-5-{[3-chloro-2-oxo-6-(1H-pyrazolo[3,4-1)]pyridin-3-ylmethyl)-1,2-dihydropyridin-4-yl]oxy}benzonitrile (24-7)

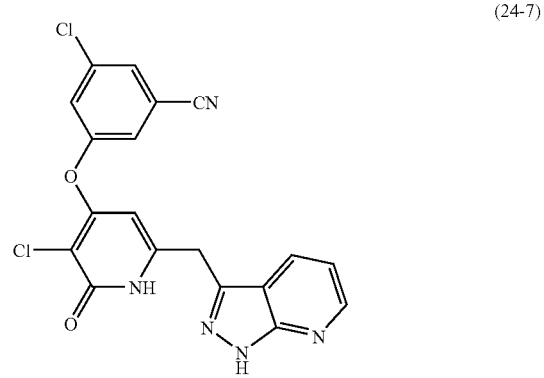 [SMILES: N#Cc1cc(Cl)cc(Oc2cc(Cc3n[nH]c4ncccc34)[nH]c(=O)c2Cl)c1]

Step: 1 4-(3-bromo-5-chlorophenoxy)-3-chloro-6-(dibromomethyl)-2-methoxypyridine

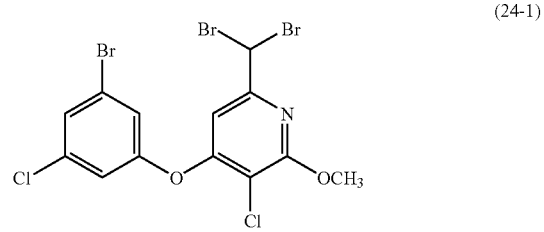 [SMILES: COc1nc(C(Br)Br)cc(Oc2cc(Cl)cc(Br)c2)c1Cl]

To a solution of 9-3 (5.0 g, 13.77 mmol) in carbon tetrachloride was added NBS (6.13 g; 34.4 mmol) and benzoyl peroxide (0.667 g; 2.75 mmol). The reaction mixture was heated at reflux overnight, cooled to room temperature, and concentrated to a solid. The crude mixture was purified via column chromatography (0-10% EtOAc in hexane) to yield the title compound. MS M+1=521.4. ¹H NMR (CDCl₃): 4.08 (s, 3H), 6.41 (s, 1H), 6.83 (s, 1H), 6.99 (m, 1H), 7.10 (m, 1H), 7.37 (m, 1H).

Step: 2 4-(3-bromo-5-chlorophenoxy)-5-chloro-6-methoxypyridine-2-carbaldehyde

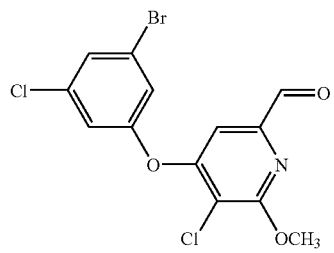

(24-2)

To a solution of 24-1 (5.6 g; 10.75 mmol) in DMF was added dimethyl amine (40% wt solution in water) (4.0 mL, 32.3 mmol). The reaction mixture stirred at room temperature overnight, diluted with water and EtOAc, and the resulting aqueous layer was extracted with EtOAc (3×). The combined organic extracts washed with water (4×), brine (1×), dried over magnesium sulfate, and evaporated to dryness. The crude product was purified via silica gel chromatography (0-20% EtOAc in hex) to yield the title compound as a white solid. MS M+1=377.9. ¹H NMR (CDCl₃): 4.10 (s, 3H), 7.00 (s, 1H), 7.05 (m, 1H), 7.10 (m, 1H), 7.40 (m, 1H), 9.82 (s, 1H).

Step: 3 [4-(3-bromo-5-chlorophenoxy)-5-chloro-6-methoxypyridin-2-yl](1H-pyrazolo[3,4-b]pyridin-3-yl)methanol (24-3)

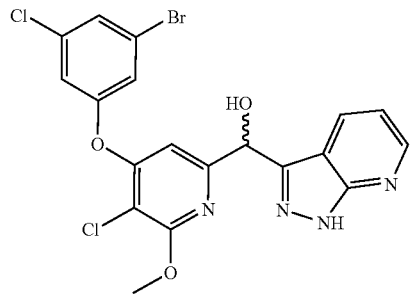

(24-3)

To a solution of 3-bromo-1H-pyrazolo[3,4-b]pyridine (315 mg, 1.59 mmol) in THF at −78° C. was added BuLi (1044 μl, 1.670 mmol) and t-BuLi (1918 μl, 3.26 mmol). The reaction mixture was stirred at −78C for 15 minutes before 24-2 (660 mg, 1.750 mmol) was added in one portion and the reaction mixture warmed to room temperature. The reaction was then quenched with 1 N HCl, adjusted to a pH of 6, and extracted with EtOAc (3×). The combined organic layers were then washed with brine and concentrated to dryness. The crude residue was purified via column chromatography (0-100% EtOAc in hexane) to yield the title compound as a white solid. MS M+1=496.5. ¹H NMR (CDCl₃): 4.10 (s, 3H), 4.50 (d, 1H), 6.08 (d, 1H), 6.62 (s, 1H), 6.90 (m, 1H), 7.00 (s, 1H), 7.10 (dd, 1H), 7.30 (m, 1H), 8.12 (d, 1H), 8.54 (d, 1H), 11.05 (bs, 1H).

Step: 4 (1-acetyl-1H-pyrazolo[3,4-b]pyridin-3-yl)[4-(3-bromo-5-chlorophenoxy)-5-chloro-6-methoxypyridin-2-yl]methyl acetate (24-4)

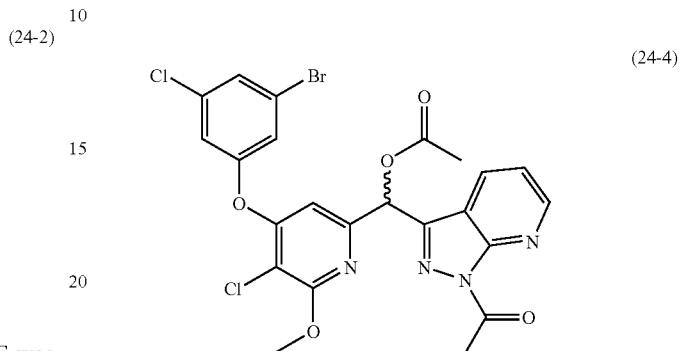

(24-4)

To a solution of 24-3 (110 mg, 0.22 mmol) in dichloromethane (4434 μl) was added acetic anhydride (62.8 μl, 0.665 mmol), pyridine (44.8 μl, 0.554 mmol), and DMAP (27.1 mg, 0.222 mmol). The reaction was stirred at room temperature for 30 minutes and concentrated to an oil. The crude residue was dissolved in EtOAc, washed with water (2×), brine (2×), and concentrated to dryness. The crude product was purified via silica gel chromatography (10-100% EtOAc in hex) to yield the title product as an oil. MS M+1=580.5. ¹H NMR (CDCl₃): 2.16 (s, 3H), 2.80 (s, 3H), 3.85 (s, 3H), 6.74 (s, 1H), 6.95 (m, 1H), 7.00 (s, 1H), 7.06 (m, 1H), 7.30 (dd, 1H), 7.36 (m, 1H), 8.26 (dd, 1H), 8.74 (dd, 1H).

Step: 5 3-{[4-(3-bromo-5-chlorophenoxy)-5-chloro-6-methoxypyridin-2-yl]methyl}-1H-pyrazolo[3,4-b]pyridine

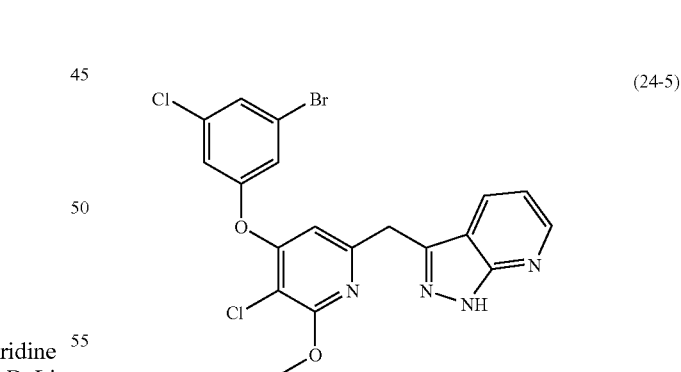

(24-5)

To a solution of 24-4 in THF (1982 μl) was added t-BuOH (26.5 μl, 0.277 mmol) and samarium (II) iodide (5748 μl, 0.575 mmol, 0.1M solution in THF). The reaction mixture was stirred for 3 hours and then diluted with water and EtOAc. The title product was obtained by an aqueous work up and silica column purification (10-100% EtOAc in hex). MS M+1=480.5. ¹H NMR (CDCl₃): 3.95 (s, 3H), 4.60 (s, 2H), 6.40 (s, 1H), 6.80 (m, 1H), 7.06 (m, 1H), 7.10 (dd, 1H), 7.30 (m, 1H), 8.05 (d, 1H), 8.50 (dd, 1H), 10.60 (bs, 1H).

Step: 6 3-chloro-5-{[3-chloro-2-methoxy-6-(1H-pyrazolo[3,4-b]pyridin-3-ylmethyl)pyridin-4-yl]oxy}benzonitrile

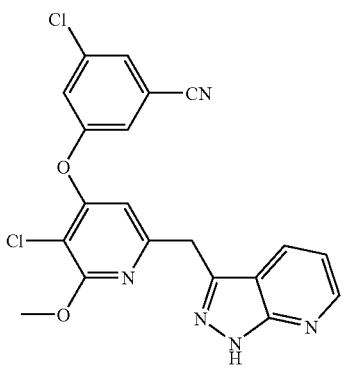

(24-6)

A solution of 24-5 (66 mg; 0.137 mmol) in dry DMF was treated with (Ph$_3$P)$_4$Pd (32 mg; 0.027 mmol) and zinc cyanide (19 mg; 0.165 mmol). The reaction mixture was heated at 100° C. with stirring under nitrogen for 2 hours. The reaction mixture was then cooled and the solids removed by filtration. The filtrate was evaporated and the residue was purified on a silica column eluted with EtOAc:hexane to give the title product as a white solid. LCMS: M+1=425.8. $^1$H NMR (CDCl$_3$): δ 4.00 (s, 3H), 4.35 (s, 2H), 6.45 (s, 1H), 7.08 (m, 1H), 7.10 (dd, 1H), 7.16 (m, 1H), 7.38 (m, 1H), 8.08 (dd, 1H), 8.54 (dd, 1H), 11.10 (bs, 1H).

Step: 7 3-Chloro-5-{[3-chloro-2-oxo-6-(1H-pyrazolo[3,4-b]pyridin-3-ylmethyl)-1,2-dihydropyridin-4-yl]oxy}benzonitrile (24-7)

A solution of 24-6 in hydrobromic acid (48% in water) was heated with stirring at 50° C. for 3 hours. The reaction mixture was cooled to room temperature and diluted with water and EtOAc. The pH of the aqueous layer was adjusted to 6, and the aqueous layer extracted with EtOAc/MeOH (4:1) (2×). The combined organic layers were washed with water (4×), brine (2×), dried over MgSO$_4$, and concentrated. The crude material was purified by reverse phase preparative HPLC on a Gilson apparatus to give the title compound as a white solid. MS M+1=411.8. $^1$H NMR (DMSO-d$_6$): 4.10 (s, 2H), 5.75 (s, 1H), 7.10 (dd, 1H), 7.60 (s, 1H), 7.65 (s, 1H), 7.85 (s, 1H), 8.05 (d, 1H), 8.42 (d, 1H), 12.32 (bs, 1H), 13.40 (bs, 1H).

EXAMPLE 25

3-Chloro-5-({3-chloro-6-[hydroxy(1H-pyrazolo[3,4-b]pyridin-3-yl)methyl]-2-methoxypyridin-4-yl}oxy)benzonitrile (25-2)

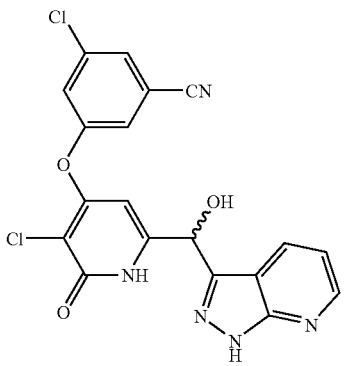

(25-2)

Step: 1 3-Chloro-5-({3-chloro-6-[hydroxy(1H-pyrazolo[3,4-b]pyridin-3-yl)methyl]-2-oxo-1,2-dihydropyridin-4-yl}oxy)benzonitrile

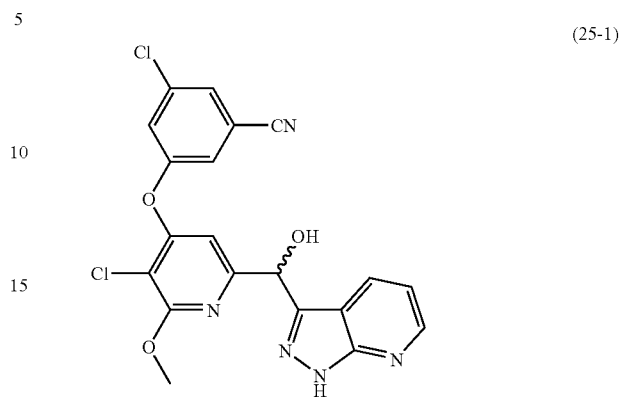

(25-1)

Compound 25-1 was prepared from Compound 24-3 using the procedure described in Example 24 for the preparation of 24-6. MS M+=441.8. $^1$H NMR (CDCl$_3$): δ 4.06 (s, 3H), 4.57 (d, 1H), 6.10 (s, 1H), 6.70 (s, 1H), 7.10-7.16 (m, 2H), 7.18 (m, 1H), 7.38 (m, 1H), 8.14 (d, 1H), 8.52 (d, 1H), 11.40 (bs, 1H).

Step: 2 3-Chloro-5-({3-chloro-6-[hydroxy(1H-pyrazolo[3,4-b]pyridin-3-yl)methyl]-2-methoxypyridin-4-yl}oxy)benzonitrile (25-2)

Compound 25-2 was prepared from 25-1 using the procedure described in Example 24 for the preparation of Compound 24-7 from 24-6. MS M+=427.8. $^1$H NMR (DMSO): δ 5.72 (d, 1H), 6.10 (s, 1H), 6.46 (d, 1H), 7.12 (m, 1H), 7.68 (s, 1H), 7.74 (s, 1H), 7.92 (s, 1H), 8.08 (d, 1H), 8.46 (d, 1H).

EXAMPLE 26

Encapsulated Oral Compositions

A capsule formulation suitable for use in the present invention can be prepared by filling standard two-piece gelatin capsules each with 100 mg of the title compound of Example 1, 150 mg of lactose, 50 mg of cellulose, and 3 mg of stearic acid. Encapsulated oral compositions containing any one of the title compounds of Examples 2 to 27 can be similarly prepared.

EXAMPLE 27

ECL Assay for Inhibition of HIV Reverse Transcriptase

An assay to determine the in vitro inhibition of HIV reverse transcriptase by compounds of the present invention was conducted as follows: HIV-1 RT enzyme (0.1 nM) was combined with inhibitor or DMSO (10%) in assay buffer (50 mM Tris-HCl, pH 7.8, 1 mM dithiothreitol, 6 mM MgCl$_2$, 80 mM KCl, 0.025% CHAPS, 0.1 mM EGTA), and the mixture pre-incubated for 30 minutes at room temperature in microtiter plates (Costar #3359). 100 μL reaction mixtures were initiated with a combination of primer-template substrate (10 nM final concentration) and dNTPs (0.6 μM dNTPs, 1.25 μM BrdUTP). The heterodimeric nucleic acid substrate was generated by annealing the DNA primer pD500 (described in Shaw-Reid et al., *J. Biol. Chem.*, 278: 2777-2780; obtained from Integrated DNA Technologies) to t500, a 500 nucleotide RNA template created by in vitro transcription (see Shaw-Reid et al., *J. Biol. Chem.*, 278: 2777-2780). After 1 hour incubation at 37° C., reactions were quenched by 10 μL of 1 N NaOH. Microtiter plates were incubated for an additional 30 minutes at room temperature and then neutralized with 10 μL of 1 N HCl. A mixture of detection buffer containing ruthenylated anti-BrdU antibody and streptavidin coated magnetic beads were added to the plate and incubated at room temperature for 1.5 hours prior to quantification via electrochemiluminescence instrument. Representative compounds of the present invention exhibit inhibition of the reverse transcriptase enzyme in this assay. For example, the title compounds set forth above in Examples 1-25 were tested in the assay and were found to have $IC_{50}$ values as set forth in Table B below.

Analogous assays were conducted substituting mutant HIV strains to determine the in vivo inhibition of compounds of the present invention against mutant HIV reverse transcriptase. In one strain the reverse transcriptase has the Y181C mutation and in the other strain the reverse transcriptase has the K103N mutation. The mutations were generated with the QUIKCHANGE site-directed mutagenesis kit (Stratagene). Representative compounds of the present invention exhibit inhibition of the reverse transcriptase enzyme in these assays. For example, the title compounds set forth above in Examples 1-25 were tested in the assays and were found to have $IC_{50}$ values as set forth in Table B:

TABLE B

| Example No. | ECL Assay (WT) $IC_{50}$ (μM) | ECL Assay (K103N) $IC_{50}$ (μM) | ECL Assay (Y181C) $IC_{50}$ (μM) |
| --- | --- | --- | --- |
| 1-7 | 0.0003 | 0.0015 | 0.0004 |
| 2-7 | 0.0005 | 0.0006 | 0.0010 |
| 3-8 | 0.0019 | 0.0047 | 0.0030 |
| 3-9 | 0.0038 | 0.0320 | 0.0110 |
| 4-4 | 0.0016 | 0.0140 | 0.0079 |
| 5-6 | 0.0012 | 0.0018 | 0.0016 |
| 5-7 | 0.0035 | 0.0520 | 0.0490 |
| 6-5 | 0.0250 | 0.0870 | 0.2700 |
| 7-1 | 0.0013 | 0.0270 | 0.0035 |
| 8-5 | 0.0009 | 0.0110 | 0.0057 |
| 9-8 | 0.0048 | 0.0130 | 0.0063 |
| 10-4 | 0.0005 | 0.0032 | 0.0006 |
| 11-7 | 0.0025 | 0.0037 | 0.0032 |
| 12-7 | 0.0250 | 0.0580 | 0.0510 |
| 13-2 | 0.0016 | 0.0026 | 0.0020 |
| 14 | 0.300 | 0.440 | 0.290 |
| 15 | 0.0033 | 0.0048 | 0.0039 |
| 16 | 0.0019 | 0.0028 | 0.0026 |
| 17-2 | 0.0019 | 0.0031 | 0.0024 |
| 18-4 | 0.0034 | 0.0051 | 0.0041 |
| 19-4 | 0.0011 | 0.0021 | 0.0015 |
| 20-3 | 0.0016 | 0.0059 | 0.0016 |
| 21-8 | 0.0008 | 0.0014 | 0.0010 |
| 22 | 0.0013 | 0.0021 | 0.0018 |
| 23-2 | 0.00096 | 0.0016 | 0.0013 |
| 24-7 | 0.0009 | 0.0017 | 0.0010 |
| 25-2 | 0.0032 | 0.013 | 0.0047 |

WT = wild-type

EXAMPLE 28

Assay for Inhibition of HIV Replication

Assays for the inhibition of acute HIV-1 infection of T-lymphoid cells (alternatively referred to herein as the "spread assay") were conducted in accordance with Vacca, J. P. et al., Proc. Natl. Acad. Sci. USA 1994, 91: 4096. The assays tested for inhibition of wild type HIV-1 and of HIV strains containing the Y181C or K103N mutation. Representative compounds of the present invention exhibit inhibition of HIV replication in the assay employing wild-type HIV-1 and the mutant strains. For example, the compounds set forth in Examples 1 to 25 were found to have $CIC_{95}$ values as set forth in Table C below in the assay employing the wild type strain. Table C also reports the $CIC_{95}$ values of certain of the title compounds of Examples 1-25 obtained in the assays employing the Y181C mutant strain and the K103N mutant strain.

TABLE C

| Example No. | Spread (WT) $CIC_{95}$ (μM) (10% FBS) | Spread (K103N) $CIC_{95}$ μM) (10% FBS) | Spread (Y181C) $CIC_{95}$ (μM) (10% FBS) |
| --- | --- | --- | --- |
| 1-7 | 0.003 | 0.094 | 0.013 |
| 2-7 | 0.003 | 0.028 | 0.014 |
| 3-8 | 0.007 | 0.031 | 0.019 |
| 3-9 | 0.055 | 0.32 | 0.36 |
| 4-4 | 0.039 | 0.207 | 0.438 |
| 5-6 | 0.042 | 0.367 | nd |
| 5-7 | 1.22 | nd | nd |
| 6-5 | 0.103 | 0.361 | nd |
| 7-1 | 0.100 | 1.704 | nd |
| 8-5 | 0.034 | 0.833 | nd |
| 9-8 | 0.638 | nd | nd |
| 10-4 | 0.028 | 0.062 | 0.046 |
| 11-7 | 0.007 | 0.014 | nd |
| 12-7 | 0.248 | 0.447 | nd |
| 13-2 | 0.004 | 0.006 | 0.008 |
| 14 | 0.330 | 0.284 | nd |
| 15 | 0.010 | 0.006 | nd |
| 16 | 0.008 | 0.021 | 0.030 |
| 17-2 | 0.006 | 0.011 | 0.042 |
| 18-4 | 0.007 | 0.006 | 0.008 |
| 19-4 | 0.009 | 0.021 | 0.048 |
| 20-3 | 0.020 | 0.087 | 0.169 |
| 21-8 | 0.003 | 0.003 | 0.008 |
| 22 | 0.002 | 0.007 | 0.063 |
| 23-2 | 0.005 | 0.011 | 0.015 |
| 24-7 | 0.0024 | 0.013 | 0.0066 |
| 25-2 | 0.028 | 0.180 | nd |

WT = wild type; FBS = fetal bovine serum; nd = not determined

EXAMPLE 29

Cytotoxicity

Cytotoxicity was determined by microscopic examination of the cells in each well in the spread assay, wherein a trained analyst observed each culture for any of the following morphological changes as compared to the control cultures: pH imbalance, cell abnormality, cytostatic, cytopathic, or crystallization (i.e., the compound is not soluble or forms crystals in the well). The toxicity value assigned to a given compound is the lowest concentration of the compound at which one of the above changes is observed. Representative compounds of the present invention exhibit no cytotoxicity at concentrations up to their $CIC_{95}$ value in the spread assay of Example 28. In particular, Compounds 5-6, 5-7, 6-5, 7-1, 8-5 and 9-8 exhibited no cytotoxicity at concentrations of up to 8.5 micromolar; Compounds 1-7, 2-7, 3-8, 3-9, 4-4, 10-4, 11-7, 12-7, 13-2, 14, 15, 16, 17-2, 18-4, 19-4, 20-3, 21-8, 22, 23-2, 24-7 and 25 exhibited no cytotoxicity at concentrations up to 833 nM; and Compound 12-7 was not tested.

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entireties into the disclosure.

What is claimed is:

1. A compound, or a pharmaceutically acceptable salt or prodrug thereof, wherein the compound is a compound of Formula III:

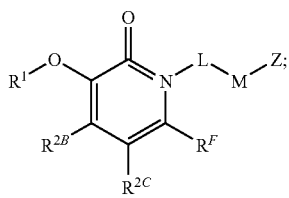

(III)

R¹ is AryA which is phenyl or naphthyl, wherein the phenyl or naphthyl is optionally substituted with from 1 to 3 substituents each of which is independently halogen, CN, NO₂, C$_{1-4}$ alkyl, C$_{1-4}$ haloalkyl, C$_{2-4}$ alkenyl, C$_{2-4}$ alkenyl substituted with CN, OH, O—C$_{1-4}$ alkyl, O—C$_{1-4}$ haloalkyl, N(R$^A$)R$^B$, C(O)N(R$^A$)R$^B$, C(O)R$^A$, CO₂R$^A$, SR$^A$, S(O)R$^A$, SO₂R$^A$, SO₂N(R$^A$)R$^B$, or SO₂N(R$^A$)C(O)R$^B$;

R$^{2B}$ and R$^{2C}$ are each independently:
(1) H,
(2) C$_{1-4}$ alkyl,
(3) CF₃,
(4) CH₂CF₃,
(5) CH₂OH,
(6) CH₂O—C$_{1-4}$ alkyl,
(7) CH₂CN,
(8) CH₂N(R$^A$)R$^B$,
(9) CH₂C(O)N(R$^A$)R$^B$,
(10) CH₂C(O)R$^A$,
(11) CH₂CO₂R$^A$,
(12) CH₂S(O)₂R$^A$,
(13) O—C$_{1-4}$ alkyl,
(14) OCF₃,
(15) Cl,
(16) Br,
(17) F,
(18) CN,
(19) NO₂,
(20) N(R$^A$)R$^B$,
(21) C(O)N(R$^A$)R$^B$,
(22) C(O)R$^A$,
(23) C(O)—C$_{1-4}$ fluoroalkyl,
(24) C(O)OR$^A$,
(25) S(O)₂R$^A$,

 (26)

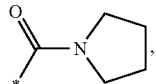 (27)

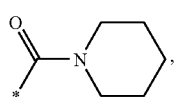 (28)

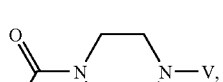 (29)

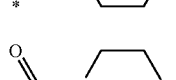 (30)

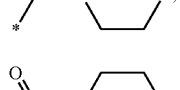 (31)

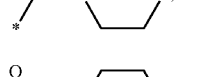 (32)

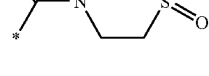 (33)

(34)

(35)

(36)

(37)

(38) cyclopropyl, or
(39) O-cyclopropyl;

V is H, CH₃, C(O)CH₃, C(O)OCH₃, or S(O)₂CH₃;

R$^F$ is H, C$_{1-4}$ alkyl, Br, Cl, F, or CN;

L is a single bond that attaches the ring nitrogen directly to M, CH₂, or CH(CH₃);

M is CH₂ or CH(CH₃);

Z is G¹ or G²;

G¹ is:

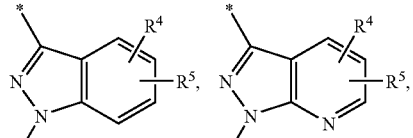

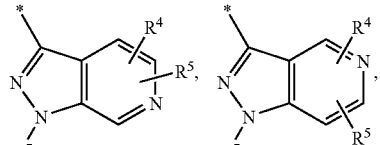

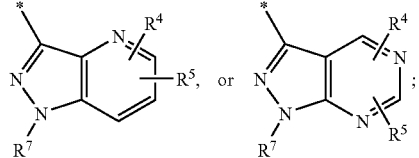

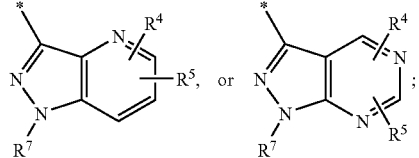

$G^2$ is:

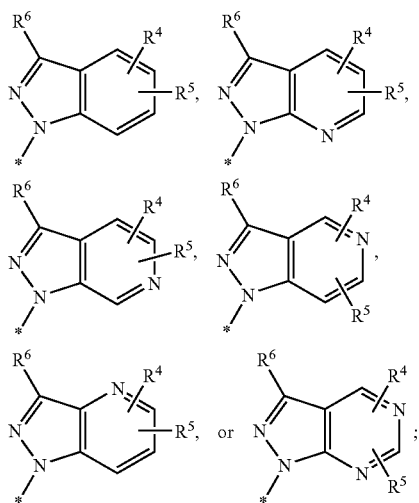

and provided that when Z is $G^2$, then L is $CH_2$ or $CH(CH_3)$, and M is $CH_2$ or $CH(CH_3)$;

$R^4$ and $R^5$ are each independently:
(1) H,
(2) $C_{1-4}$ alkyl,
(3) $CF_3$,
(4) $CH_2CF_3$,
(5) $CH_2OH$,
(6) $CH_2O-C_{1-4}$ alkyl,
(7) $CH_2CN$,
(8) $CH_2N(R^A)R^B$,
(9) $CH_2C(O)N(R^A)R^B$,
(10) $CH_2C(O)R^A$,
(11) $CH_2CO_2R^A$,
(12) $CH_2S(O)_2R^A$,
(13) $O-C_{1-4}$ alkyl,
(14) $OCF_3$,
(15) Cl,
(16) Br,
(17) F,
(18) CN,
(19) $NO_2$,
(20) $N(R^A)R^B$,
(21) $C(O)N(R^A)R^B$,
(22) $C(O)R^A$,
(23) $C(O)-C_{1-4}$ fluoroalkyl,
(24) $C(O)OR^A$,
(25) $S(O)_2R^A$,

(26) 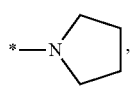

(27) 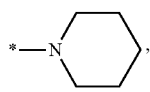

(28) 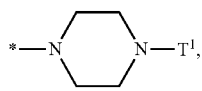

(29) 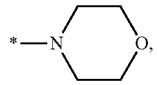

(30) 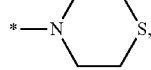

(31) 

(32) 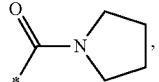

(33) 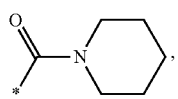

(34) 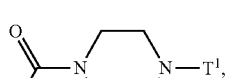

(35) 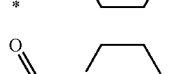

(36) 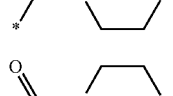

(37) 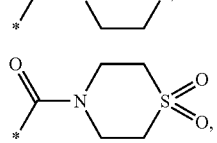

(38) cyclopropyl,
(39) O-cyclopropyl,
(40) OH, or
(41) imidazolyl;

each $T^1$ is independently H, $C_{1-4}$ alkyl, $C(O)R^A$, $C(O)OR^A$, $C(O)N(R^A)R^B$, or $S(O)_2R^A$;

R6 is:
(1) H,
(2) $C_{1-4}$ alkyl,
(3) OH,
(4) $O-C_{1-4}$ alkyl,
(5) $NH_2$,
(6) $N(H)-C_{1-4}$ alkyl,
(7) $N(-C_{1-4}$ alkyl$)_2$, or
(8) a saturated heterocyclic ring selected from the group consisting of 1-azetidinyl, 1-pyrrolidinyl, 1-piperidinyl, 1-piperazinyl, 1-azepanyl, 4-morpholinyl, and 4-thiomorpholinyl wherein the S in the ring is optionally S(O) or $S(O)_2$, wherein the heterocyclic ring is optionally substituted with 1 or 2 substituents each of which is independently $C_{1-4}$ alkyl, $C(O)-C_{1-4}$ alkyl, $C(O)O-C_{1-4}$ alkyl $C(O)NH_2$, $C(O)NH(-C_{1-4}$ alkyl), $C(O)N(-C_{1-4}$ alkyl$)_2$, or $S(O)_2-C_{1-4}$ alkyl;

$R^7$ is H or $C_{1-4}$ alkyl;
each $R^A$ is independently H or $C_{1-4}$ alkyl; and
each $R^B$ is independently H or $C_{1-4}$ alkyl.

2. The compound of Formula III according to claim 1, or a pharmaceutically acceptable salt or prodrug thereof, wherein:
R$^1$ is AryA which is:

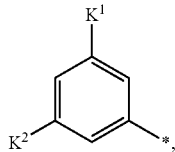

wherein K$^1$ and K$^2$ are each independently Br, Cl, or CN;
R$^{2B}$ is H, CH$_3$, CF$_3$, Cl, Br, F, or CN;
R$^{2C}$ is H, CH$_3$, CF$_3$, Cl, Br, F, or CN;
R$^F$ is H;
L is a bond or CH$_2$;
M is CH$_2$;
Z is

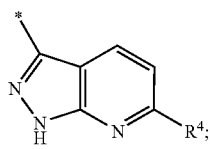

and
R$^4$ is H or NH$_2$.

3. The compound of Formula III according to claim 2, or a pharmaceutically acceptable salt or prodrug thereof, wherein:
R$^1$ is AryA which is selected from the group consisting of 3-chloro-5-cyanophenyl, 3-bromo-5-chlorophenyl, 3,5-dicyanophenyl, and 3,5-dichlorophenyl;
R$^{2B}$ is H, CH$_3$, CF$_3$, or Cl;
R$^{2C}$ is H, CH$_3$, or Cl; and
L is a bond.

4. A compound of Formula III according to claim 2, or a pharmaceutically acceptable salt or prodrug thereof, wherein R$^1$ is 3-chloro-5-cyanophenyl.

5. A compound selected from the group consisting of:
3-chloro-5-({5-chloro-3-fluoro-6-[(1H-pyrazolo[3,4-b]pyridin-3-ylmethyl)amino]pyridin-2-yl}oxy)benzonitrile (1-7);
3-[(6-{[(6-amino-1H-pyrazolo[3,4-b]pyridin-3-yl)methyl]amino}-5-chloro-3-fluoropyridin-2-yl)oxy]-5-chlorobenzonitrile(2-7);
3-chloro-5-({3-chloro-2-oxo-6-[2-(1H-pyrazolo[3,4-b]pyridin-3-yl)ethyl]-1,2-dihydropyridin-4-yl}oxy)benzonitrile (3-8);
3-chloro-5-({2-oxo-6-[2-(1H-pyrazolo[3,4-b]pyridin-3-yl)ethyl]-1,2-dihydropyridin-4-yl}oxy)benzonitrile (3-9);
3-({6-[2-(6-amino-1H-pyrazolo[3,4-b]pyridin-3-yl)ethyl]-3-chloro-2-oxo-1,2-dihydropyridin-4-yl}oxy)-5-chlorobenzonitrile (4-4);
3-chloro-5-({3,5-dichloro-2-oxo-6-[2-(1H-pyrazolo[3,4-b]pyridin-3-yl)ethyl]-1,2-dihydropyridin-4-yl}oxy) benzonitrile (5-6);
ethyl 3-chloro-5-({3,5-dichloro-2-oxo-6-[2-(1H-pyrazolo[3,4-b]pyridin-3-yl)ethyl]-1,2-dihydropyridin-4-yl}oxy)benzoate (5-7);
3-chloro-5-({5-chloro-2-[2-(1H-pyrazolo[3,4-b]pyridin-3-yl)ethyl]pyridin-4-yl}oxy)benzonitrile (6-5);
3-chloro-5-{[3,5-dichloro-2-methyl-6-(1H-pyrazolo[3,4-b]pyridin-3-ylmethoxy)pyridin-4-yl]oxy}benzonitrile (7-1);
3-chloro-5-({3-chloro-2-oxo-6-[(1H-pyrazolo[3,4-b]pyridin-3-ylmethyl)amino]-1,2-dihydropyridin-4-yl} oxy) benzonitrile (8-5);
3-chloro-5-({3-chloro-2-oxo-6-[(2-oxo-2,3-dihydro-1H-benzimidazol-1-yl)methyl]-1,2-dihydropyridin-4-yl}oxy)benzonitrile(9-8);
3-chloro-5-({3-chloro-2,5-difluoro-6-[(1H-pyrazolo[3,4-b]pyridin-3-ylmethyl)amino]pyridin-4-yl}oxy)benzonitrile (10-4);
3-chloro-5-{[4-methyl-2-oxo-1-(1H-pyrazolo[3,4-b]pyridin-3-ylmethyl)-1,2-dihydropyridin-3-yl]oxy}benzonitrile (11-7);
3-chloro-5-({4-methyl-2-oxo-1-[2-(1H-pyrazolo[3,4-b]pyridin-3-yl)ethyl]-1,2-dihydropyridin-3-yl}oxy)benzonitrile (12-7);
3-chloro-5-{[2-oxo-1-(1H-pyrazolo[3,4-b]pyridin-3-ylmethyl)-4-(trifluoromethyl)-1,2-dihydropyridin-3-yl]oxy}benzonitrile (13-2);
N-(2-chlorobenzyl)-2-[3-(3-chloro-5-cyanophenoxy)-2-oxo-4-(trifluoromethyl)pyridin-1(2H)-yl]-N-methylacetamide (14);
N-[4-(aminosulfonyl)-2-chlorophenyl]-2-[3-(3-chloro-5-cyanophenoxy)-2-oxo-4-(trifluoromethyl)pyridin-1(2H)-yl]acetamide (15);
N-[4-(aminosulfonyl)-2-chlorophenyl]-2-[3-(3-bromo-5-chlorophenoxy)-2-oxo-4-(trifluoromethyl)pyridin-1(2H)-yl]acetamide (16);
3-{[1-[(6-amino-1H-pyrrolo[2,3-b]pyridin-3-yl)methyl]-2-oxo-4-(trifluoromethyl)-1,2-dihydropyridin-3-yl]oxy}-5-chlorobenzonitrile (17-2);
5-{ [2-oxo-1-(1H-pyrazolo[3,4-b]pyridine-3-ylmethyl)-4-(trifluoromethyl)-1,2-dihydropyridin-3-yl]oxy}isophthalonitrile (18-4);
3-(3,5-dichlorophenoxy)-1-(1H-pyrazolo[3,4-b]pyridin-3-ylmethyl)-4-(trifluoromethyppyridin-2(1H)-one (19-4);
1-[(6-amino-1H-pyrrolo[2,3-b]pyridin-3-yl)methyl]-3-(3, 5-dichlorophenoxy)-4-(trifluoromethyl)pyridin-2(1H)-one (20-3);
3-chloro-5-{[4-chloro-2-oxo-1-(1H-pyrazolo[3,4-b]pyridin-3-ylmethyl)-1,2-dihydropyridin-3-yl]oxy}benzonitrile (21-8);
3-({1-[(6-amino-1H-pyrazolo[3,4-b]pyridin-3-yl)methyl]-4-(trifluoromethyl)-2-oxo-1,2-dihydropyridin-3-yl}oxy)-5-chlorobenzonitrile trifluoroacetate (22);
3-chloro-5-{[4,5-dichloro-2-oxo-1-(1H-pyrazolo[3,4-b]pyridin-3-ylmethyl)-1,2-dihydropyridin-3-yl] oxy}benzonitrile (23-2);
3-chloro-5-{[3-chloro-2-oxo-6-(1H-pyrazolo[3,4-b]pyridin-3-ylmethyl)-1,2-dihydropyridin-4-yl] oxy}benzonitrile (24-7);
3-chloro-5-({3-chloro-6-[hydroxy(1H-pyrazolo[3,4-b]pyridin-3-yl)methyl]-2-oxo-1,2-dihydropyridin-4-yl}oxy)benzonitrile (25);
and pharmaceutically acceptable salts thereof.

6. A compound according to claim 5 selected from the group consisting of:
3-chloro-5-{[4-methyl-2-oxo-1-(1H-pyrazolo[3,4-b]pyridin-3-ylmethyl)-1,2-dihydropyridin-3-yl] oxy}benzonitrile (11-7);
3-chloro-5-({4-methyl-2-oxo-1-[2-(1H-pyrazolo[3,4-b]pyridin-3-yl)ethyl]-1,2-dihydropyridin-3-yl}oxy)benzonitrile (12-7);
3-chloro-5-{[2-oxo-1-(1H-pyrazolo[3,4-b]pyridin-3-ylmethyl)-4-(trifluoromethyl)-1,2-dihydropyridin-3-yl] oxy}benzonitrile (13-2);

3-{1-[(6-amino-1H-pyrrolo[2,3-b]pyridin-3-yl)methyl]-2-oxo-4-(trifluoromethyl)-1,2-dihydropyridin-3-yl]oxy}-5-chlorobenzonitrile (17-2);

5-{[2-oxo-1-(1H-pyrazolo[3,4-b]pyridine-3-ylmethyl)-4-(trifluoromethyl)-1,2-dihydropyridin-3-yl]oxy}isophthalonitrile (18-4);

3-(3,5-dichlorophenoxy)-1-(1H-pyrazolo[3,4-b]pyridin-3-ylmethyl)-4-(trifluoromethyppyridin-2(1H)-one (19-4);

1-[(6-amino-1H-pyrrolo[2,3-b]pyridin-3-yl)methyl]-3-(3,5-dichlorophenoxy)-4-(trifluoromethyl)pyridin-2(1H)-one (20-3);

3-chloro-5-{[4-chloro-2-oxo-1-(1H-pyrazolo[3,4-b]pyridin-3-ylmethyl)-1,2-dihydropyridin-3-yl]oxy}benzonitrile (21-8);

3-({1-[(6-amino-1H-pyrazolo[3,4-b]pyridin-3-yl)methyl]-4-chloro-2-oxo-1,2-dihydropyridin-3-yl}oxy)-5-chlorobenzonitrile trifluoroacetate (22);

3-chloro-5-{[4,5-dichloro-2-oxo-1-(1H-pyrazolo[3,4-b]pyridin-3-ylmethyl)-1,2-dihydropyridin-3-yl]oxy}benzonitrile (23-2);

and pharmaceutically acceptable salts thereof.

* * * * *